US010329357B2

(12) United States Patent
Peters et al.

(10) Patent No.: US 10,329,357 B2
(45) Date of Patent: *Jun. 25, 2019

(54) TREATMENT OF OCULAR DISEASE

(71) Applicant: Aerpio Therapeutics, Inc., Cincinnati, OH (US)

(72) Inventors: Kevin Peters, Cincinnati, OH (US); Robert Shalwitz, Bexley, OH (US)

(73) Assignee: AERPIO THERAPEUTICS, INC., Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/463,340

(22) Filed: Mar. 20, 2017

(65) Prior Publication Data

US 2018/0044432 A1  Feb. 15, 2018

Related U.S. Application Data

(63) Continuation of application No. 14/627,463, filed on Feb. 20, 2015, now abandoned, which is a continuation of application No. 13/652,154, filed on Oct. 15, 2012, now Pat. No. 8,999,325.

(60) Provisional application No. 61/546,708, filed on Oct. 13, 2011.

(51) Int. Cl.
| C07K 16/40 | (2006.01) |
| A61K 39/395 | (2006.01) |
| A61K 39/00 | (2006.01) |
| A61P 27/02 | (2006.01) |

(52) U.S. Cl.
CPC ........ *C07K 16/40* (2013.01); *A61K 2039/505* (2013.01); *A61K 2039/54* (2013.01); *A61P 27/02* (2018.01); *C07K 2317/75* (2013.01); *C07K 2317/76* (2013.01)

(58) Field of Classification Search
CPC ................ C07K 16/40; C07K 2317/75; C07K 2317/76; C07K 2317/24; A61K 2039/505; A61K 2039/54
See application file for complete search history.

(56) References Cited

U.S. PATENT DOCUMENTS

| 4,179,337 | A | 12/1979 | Davis et al. |
| 4,301,144 | A | 11/1981 | Iwashita et al. |
| 4,399,216 | A | 8/1983 | Axel et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,740,461 | A | 4/1988 | Kaufman |
| 4,791,192 | A | 12/1988 | Nakagawa et al. |
| 4,816,567 | A | 3/1989 | Cabilly et al. |
| 4,912,040 | A | 3/1990 | Kaufman et al. |
| 4,959,455 | A | 9/1990 | Clark et al. |
| 5,225,539 | A | 7/1993 | Winter |
| 5,545,806 | A | 8/1996 | Lonberg et al. |
| 5,545,807 | A | 8/1996 | Surani et al. |
| 6,075,181 | A | 6/2000 | Kucherlapati et al. |
| 6,114,598 | A | 9/2000 | Kucherlapati et al. |
| 6,133,426 | A | 10/2000 | Gonzalez et al. |
| 6,150,584 | A | 11/2000 | Kucherlapati et al. |
| 6,162,963 | A | 12/2000 | Kucherlapati et al. |
| 7,226,755 | B1 | 6/2007 | Peters et al. |
| 7,507,568 | B2 | 3/2009 | Evdokimov et al. |
| 7,589,212 | B2 | 9/2009 | Gray et al. |
| 7,622,593 | B2 | 11/2009 | Gray et al. |
| 7,632,862 | B2 | 12/2009 | Peters et al. |
| 7,769,575 | B2 | 8/2010 | Evdokimov et al. |
| 7,795,444 | B2 | 9/2010 | Gray et al. |
| 7,973,142 | B2 | 7/2011 | Rotello et al. |
| 8,106,078 | B2 | 1/2012 | Gray et al. |
| 8,188,125 | B2 | 5/2012 | Gray et al. |
| 8,258,311 | B2 | 9/2012 | Gray et al. |
| 8,329,916 | B2 | 12/2012 | Gray et al. |
| 8,338,615 | B2 | 12/2012 | Gray et al. |
| 8,524,235 | B2 | 9/2013 | Rotello et al. |
| 8,569,348 | B2 | 10/2013 | Shalwitz et al. |
| 8,846,685 | B2 | 9/2014 | Gray et al. |
| 8,883,832 | B2 | 11/2014 | Shalwitz et al. |
| 8,895,563 | B2 | 11/2014 | Gray et al. |
| 8,946,232 | B2 | 2/2015 | Gray et al. |
| 8,999,325 | B2 | 4/2015 | Peters et al. |
| 9,096,555 | B2 | 8/2015 | Shalwitz et al. |
| 9,126,958 | B2 | 9/2015 | Gray et al. |
| 9,174,950 | B2 | 11/2015 | Shalwitz et al. |
| 9,284,285 | B2 | 3/2016 | Gray et al. |

(Continued)

FOREIGN PATENT DOCUMENTS

| EP | 1165115 B1 | 5/2003 |
| EP | 1292335 B1 | 5/2007 |

(Continued)

OTHER PUBLICATIONS

Rudikoff et al., PNAS 79: 1979-1983 (Year: 1982).*
Wu et al., J. Mol. Biol. 294: 151-162 (Year: 1999).*
Adamsky, et al. Glial tumor cell adhesion is mediated by binding of the FNIII domain of receptor protein tyrosine phosphatase beta (RPTPbeta) to tenascin C. Oncogene. Feb. 1, 2001;20(5):609-18.
Ardelt, et al. Estradiol regulates angiopoietin-1 mRNA expression through estrogen receptor-alpha in a rodent experimental stroke model. Stroke. Feb. 2005;36(2):337-41. Epub Jan. 6, 2005.
Bosse, et al. Only simultaneous blocking of the L- and P-selectin completely inhibits neutrophil migration into mouse peritoneum. Eur J Immunol. Dec. 1994;24(12):3019-24.

(Continued)

*Primary Examiner* — Phuong Huynh
(74) *Attorney, Agent, or Firm* — Wilson Sonsini Goodrich & Rosati

(57) ABSTRACT

Disclosed are methods for treating eye diseases or conditions characterized by vascular instability, vascular leakage and neovacularization such as diabetic macular edema, age-related macular edema, choroidal neovascularization, diabetic retinopathy, trauma, ocular ischemia, retinal angiomatous proliferation, macular telangiectasia and uveitis.

11 Claims, 7 Drawing Sheets

Specification includes a Sequence Listing.

(56) References Cited

U.S. PATENT DOCUMENTS

| | | | |
|---|---|---|---|
| RE46,592 | E | 10/2017 | Gray et al. |
| 9,795,594 | B2 | 10/2017 | Gray et al. |
| 9,926,367 | B2 | 3/2018 | Rotello et al. |
| 9,949,956 | B2 | 4/2018 | Shalwitz et al. |
| 2003/0158083 | A1 | 8/2003 | Peters |
| 2004/0077065 | A1 | 4/2004 | Evdokimov et al. |
| 2004/0254197 | A1 | 12/2004 | Tasaka et al. |
| 2005/0059639 | A1 | 3/2005 | Wei |
| 2007/0059762 | A1 | 3/2007 | Araki et al. |
| 2007/0299116 | A1 | 12/2007 | Gray et al. |
| 2008/0004267 | A1 | 1/2008 | Gray et al. |
| 2008/0076764 | A1 | 3/2008 | Peters et al. |
| 2008/0108631 | A1 | 5/2008 | Gray et al. |
| 2009/0022715 | A1 | 1/2009 | Rotello et al. |
| 2009/0227639 | A1 | 9/2009 | Gray et al. |
| 2010/0016336 | A1 | 1/2010 | Gray et al. |
| 2010/0030487 | A1 | 2/2010 | Evdokimov et al. |
| 2010/0056610 | A1 | 3/2010 | Peters et al. |
| 2010/0069448 | A1 | 3/2010 | Gray et al. |
| 2010/0111894 | A1 | 5/2010 | Benny-Ratsaby et al. |
| 2010/0256147 | A1 | 10/2010 | Hangauer, Jr. |
| 2011/0212951 | A1 | 9/2011 | Gray et al. |
| 2011/0268694 | A1 | 11/2011 | Shalwitz et al. |
| 2011/0274699 | A1 | 11/2011 | Rotello et al. |
| 2012/0077853 | A1 | 3/2012 | Gray et al. |
| 2012/0077975 | A1 | 3/2012 | Gray et al. |
| 2012/0128625 | A1 | 5/2012 | Shalwitz et al. |
| 2012/0129847 | A1 | 5/2012 | Peters et al. |
| 2013/0023542 | A1 | 1/2013 | Gray et al. |
| 2013/0023543 | A1 | 1/2013 | Gray et al. |
| 2013/0095065 | A1 | 4/2013 | Peters et al. |
| 2013/0095105 | A1 | 4/2013 | Peters et al. |
| 2013/0096140 | A1 | 4/2013 | Gray et al. |
| 2013/0324558 | A1 | 12/2013 | Gray et al. |
| 2013/0331386 | A1 | 12/2013 | Shalwitz et al. |
| 2014/0044707 | A1 | 2/2014 | Rotello et al. |
| 2014/0066458 | A1 | 3/2014 | Shalwitz et al. |
| 2014/0179693 | A1 | 6/2014 | Shalwitz et al. |
| 2014/0221666 | A1 | 8/2014 | Gray et al. |
| 2014/0242026 | A1 | 8/2014 | Shalwitz et al. |
| 2014/0249100 | A1 | 9/2014 | Shalwitz et al. |
| 2014/0275103 | A1 | 9/2014 | Peters et al. |
| 2014/0288134 | A1 | 9/2014 | Peters et al. |
| 2015/0210656 | A1 | 7/2015 | Gray et al. |
| 2015/0232575 | A1 | 8/2015 | Peters et al. |
| 2016/0008327 | A1 | 1/2016 | Shalwitz et al. |
| 2016/0220540 | A1 | 8/2016 | Peters et al. |
| 2016/0220541 | A1 | 8/2016 | Peters et al. |
| 2016/0374996 | A1 | 12/2016 | Gray et al. |
| 2018/0009890 | A1 | 1/2018 | Peters et al. |
| 2018/0037579 | A1 | 2/2018 | Peters et al. |
| 2018/0092883 | A1 | 4/2018 | Peters et al. |

FOREIGN PATENT DOCUMENTS

| | | | |
|---|---|---|---|
| EP | 2142189 | B1 | 2/2013 |
| EP | 3168234 | A1 | 5/2017 |
| EP | 2371865 | B1 | 7/2017 |
| EP | 2592073 | B1 | 8/2017 |
| WO | WO-9312227 | A1 | 6/1993 |
| WO | WO-9845331 | A2 | 10/1998 |
| WO | WO-0057901 | A1 | 10/2000 |
| WO | WO-0065085 | A1 | 11/2000 |
| WO | WO-2006068953 | A2 | 6/2006 |
| WO | WO-2006116713 | A1 | 11/2006 |
| WO | WO-2007033216 | A2 | 3/2007 |
| WO | WO-2007116360 | A2 | 10/2007 |
| WO | WO-2008002569 | A2 | 1/2008 |
| WO | WO-2008002570 | B1 | 4/2008 |
| WO | WO-2008002571 | B1 | 4/2008 |
| WO | WO-2009006112 | A1 | 1/2009 |
| WO | WO-2009055343 | A2 | 4/2009 |
| WO | WO-2009136352 | A1 | 11/2009 |
| WO | WO-2010081172 | A1 | 7/2010 |
| WO | WO-2011005330 | A1 | 1/2011 |
| WO | WO-2012047966 | A2 | 4/2012 |
| WO | WO-2013056233 | A1 | 4/2013 |
| WO | WO-2013056240 | A1 | 4/2013 |

OTHER PUBLICATIONS

Bussolino, et al. Molecular mechanisms of blood vessel formation. Trends Biochem Sci. Jul. 1997;22(7):251-6.

Clackson, et al. Making antibody fragments using phage display libraries. Nature. Aug. 15, 1991;352(6336):624-8.

Co-pending U.S. Appl. No. 14/938,526, filed Nov. 11, 2015.

Co-pending U.S. Appl. No. 15/438,218, filed Feb. 21, 2017.

Co-pending U.S. Appl. No. 15/443,353, filed Feb. 27, 2017.

Doukas, et al. Topical administration of a multi-targeted kinase inhibitor suppresses choroidal neovascularization and retinal edema. J Cell Physiol. Jul. 2008;216(1):29-37. doi: 10.1002/jcp.21426.

European search report with written opinion dated May 12, 2015 for EP12840725.

Fachinger, et al. Functional interaction of vascular endothelial-protein-tyrosine phosphatase with the angiopoietin receptor Tie-2. Oncogene. Oct. 21, 1999;18(43):5948-53.

Foehr, et al. Targeting of the receptor protein tyrosine phosphatase beta with a monoclonal antibody delays tumor growth in a glioblastoma model. Cancer Res. Feb. 15, 2006;66(4):2271-8.

Folkman. Tumor angiogenesis. The Molecular Basis of Cancer (eds. Mendelsohn, J., Howley, P. M., Israel, M. A. & Liotta, L. A.) Ch. 10. 206-232 (1995).

Gaits, et al. Increase in receptor-like protein tyrosine phosphatase activity and expression level on density-dependent growth arrest of endothelial cells. Biochem J. Oct. 1, 1995;311 ( Pt 1):97-103.

Gotsch, et al. VE-cadherin antibody accelerates neutrophil recruitment in vivo. J Cell Sci. Mar. 1997;110 ( Pt 5):583-8.

Harder, et al. Characterization and kinetic analysis of the intracellular domain of human protein tyrosine phosphatase 13 (HPTP(3) using synthetic phosphopeptides. Biochem J. 1994; 296:395-401.

International search report and written opinion dated Dec. 6, 2012 for PCT/US2012/060263.

Itoh, et al. Purification and characterization of the catalytic domains of the human receptor-linked protein tyrosine phosphatases HPTP beta, leukocyte common antigen (LCA), and leukocyte common antigen-related molecule (LAR). J Biol Chem. Jun. 15, 1992;267(17):12356-63.

Krueger, et al. Structural diversity and evolution of human receptor-like protein tyrosine phosphatases. EMBO J. Oct. 1990;9(10):3241-52.

Kugathasan, et al. Role of angiopoietin-1 in experimental and human pulmonary arterial hypertension. Chest. Dec. 2005;128(6 Suppl):633S-642S.

Lin, et al. Inhibition of tumor angiogenesis using a soluble receptor establishes a role for Tie2 in pathologic vascular growth. J Clin Invest. Oct. 15, 1997;100(8):2072-8.

Lorente, et al. Functional comparison of long and short splice forms of RPTPbeta: implications for glioblastoma treatment. Neuro Oncol. Apr. 2005;7(2):154-63.

Morrison, et al. Chimeric human antibody molecules: mouse antigen-binding domains with human constant region domains. Proc Natl Acad Sci U S A. Nov. 1984;81(21):6851-5.

Muller, et al. A role for receptor tyrosine phosphatase zeta in glioma cell migration. Oncogene. Oct. 2, 2003;22(43):6661-8.

Muller, et al. Receptor protein tyrosine phosphatase zeta as a therapeutic target for glioblastoma therapy. Expert Opin Ther Targets. Jun. 2004;8(3):211-20.

Muyldermans. Single domain camel antibodies: current status. J Biotechnol. Jun. 2001;74(4):277-302.

Nawroth, et al. VE-PTP and VE-cadherin ectodomains interact to facilitate regulation of phosphorylation and cell contacts. EMBO J. Sep. 16, 2002;21(18):4885-95.

Nguyen, et al. Cellular interactions in vascular growth and differentiation. Int Rev Cytol. 2001;204:1-48.

Nguyen, et al. Vascular endothelial growth factor is a critical stimulus for diabetic macular edema. Am J Ophthalmol. Dec. 2006;142(6):961-9. Epub Aug. 2, 2006.

(56) References Cited

OTHER PUBLICATIONS

Notice of allowance dated Jan. 30, 2015 for U.S. Appl. No. 13/652,154.
Office action dated Apr. 7, 2014 for U.S. Appl. No. 13/652,154.
Office action dated Sep. 5, 2013 for U.S. Appl. No. 13/652,154.
Office action dated Sep. 2, 2016 for U.S. Appl. No. 14/627,463.
O'Reilly, et al. Angiostatin: a novel angiogenesis inhibitor that mediates the suppression of metastases by a Lewis lung carcinoma. Cell. Oct. 21, 1994;79(2):315-28.
O'Reilly, et al. Endostatin: an endogenous inhibitor of angiogenesis and tumor growth. Cell. Jan. 24, 1997;88(2):277-85.
Praidou, et al. Angiogenic growth factors and their inhibitors in diabetic retinopathy. Curr Diabetes Rev. Sep. 2010;6(5):304-12.
Riemer, et al. Matching of trastuzumab (Herceptin) epitope mimics onto the surface of Her-2/neu—a new method of epitope definition. Mol Immunol. May 2005;42(9):1121-4. Epub Jan. 8, 2005.
Schindelholz, et al. Regulation of CNS and motor axon guidance in *Drosophila* by the receptor tyrosine phosphatase DPTP52F. Development. Nov. 2001;128(21):4371-82.
Shen, et al. In vivo immunostaining demonstrates macrophages associate with growing and regressing vessels. Invest Ophthalmol Vis Sci. Sep. 2007;48(9):4335-41.
Shintei, et al., Newly Revised Disease and Drugs, Yakuji Nippo Limited, 1986 (Third print), p. 504-510. (English Translation).
Stancovski, et al. Mechanistic aspects of the opposing effects of monoclonal antibodies to the ERBB2 receptor on tumor growth. Proc Natl Acad Sci U S A. Oct. 1, 1991;88(19):8691-5.
Suri, et al. Increased vascularization in mice overexpressing angiopoietin-1. Science. Oct. 16, 1998;282(5388):468-71.
Thurston. Complementary actions of VEGF and angiopoietin-1 on blood vessel growth and leakage. J Anat. Jun. 2002;200(6):575-80.
Thurston, et al. Angiopoietin-1 protects the adult vasculature against plasma leakage. Nat Med. Apr. 2000;6(4):460-3.
Tobe, et al. Targeted disruption of the FGF2 gene does not prevent choroidal neovascularization in a murine model. Am J Pathol. Nov. 1998;153(5):1641-6.
Ulbricht, et al. Expression and function of the receptor protein tyrosine phosphatase zeta and its ligand pleiotrophin in human astrocytomas. J Neuropathol Exp Neurol. Dec. 2003;62(12):1265-75.
Van Der Flier, et al. Antibody neutralization of vascular endothelial growth factor (VEGF) fails to attenuate vascular permeability and brain edema in experimental pneumococcal meningitis. J Neuroimmunol. Mar. 2005;160(1-2):170-7.
Winderlich, et al. VE-PTP controls blood vessel development by balancing Tie-2 activity. J Cell Biol. May 18, 2009;185(4):657-71. doi: 10.1083/jcb.200811159.
Witte, et al. Monoclonal antibodies targeting the VEGF receptor-2 (Flk1/KDR) as an anti-angiogenic therapeutic strategy. Cancer Metastasis Rev. Jun. 1998;17(2):155-61.
Wright, et al. Protein-tyrosine phosphatases in the vessel wall: differential expression after acute arterial injury. Arterioscler Thromb Vasc Biol. May 2000;20(5):1189-98.
Wu, et al. Humanization of a murine monoclonal antibody by simultaneous optimization of framework and CDR residues. J Mol Biol. Nov. 19, 1999;294(1):151-62.
Yancopoulos, et al. Vascular-specific growth factors and blood vessel formation. Nature. Sep. 14, 2000;407(6801):242-8.
Yu, et al. Interaction between bevacizumab and murine VEGF-A: a reassessment. Invest Ophthalmol Vis Sci. Feb. 2008;49(2):522-7. doi: 10.1167/iovs.07-1175.
Journal of the Showa Medical Association, 2010, vol. 70, No. 1, pp. 45-51.
Baumer, et al. Vascular endothelial cell-specific phosphotyrosine phosphatase (VE-PTP) activity is required for blood vessel development. Blood. Jun. 15, 2006;107(12):4754-62. Epub Mar. 2, 2006.
Broerman, et al. Dissociation of VE-PTP from VE-cadherin is required for leukocyte extravasation and for VEGF-induced vascular permeability in vivo. J Exp Med. Nov. 21, 2011;208(12):2393-401. doi: 10.1084/jem.20110525. Epub Oct. 24, 2011.
Co-pending U.S. Appl. No. 15/705,639, filed Sep. 15, 2017.
Co-pending U.S. Appl. No. 15/894,442, filed Feb. 12, 2018.
Co-pending U.S. Appl. No. 15/913,392, filed Mar. 6, 2018.
European search report and search opinion dated May 11, 2015 for EP Application No. 12840220.3.
Fukuhara, et al. Vascular endothelial cells and adjoining cells for their mutual adhesion/interaction for stabilization and angiogenesis. Seikagaku. Apr. 2010;82(4):290-301.
International search report and written opinion dated Dec. 24, 2012 for PCT/US2012/060273.
Lip, et al. Plasma vascular endothelial growth factor, angiopoietin-2, and soluble angiopoietin receptor tie-2 in diabetic retinopathy: effects of laser photocoagulation and angiotensin receptor blockade. Br J Ophthalmol. Dec. 2004;88(12):1543-6.
LO. Antibody humanization by CDR grafting. Methods Mol Biol. 2004;248:135-59.
Marneros, et al. Endogenous endostatin inhibits choroidal neovascularization. FASEB J. Dec. 2007;21(14):3809-18. Epub May 25, 2007.
Office action dated Jan. 4, 2016 for U.S. Appl. No. 13/652,203.
Office action dated Mar. 1, 2018 for U.S. Appl. No. 15/438,218.
Office action dated Apr. 17, 2015 for U.S. Appl. No. 13/652,203.
Office action dated May 15, 2014 for U.S. Appl. No. 13/652,203.
Office action dated Aug. 22, 2016 for U.S. Appl. No. 13/652,203.
Office action dated Sep. 11, 2013 for U.S. Appl. No. 13/652,203.
Smith, et al. Oxygen-induced retinopathy in the mouse. Invest Ophthalmol Vis Sci. Jan. 1994;35(1):101-11.
Thomson, et al., A lymphatic defect causes ocular hypertension and glaucoma in mice, The Journal of Clinical Investigation, Oct. 2014, 124(10):4320-4.
U.S. Appl. No. 15/438,218 Office Action dated Aug. 3, 2018.
U.S. Appl. No. 15/438,218 Notice of Allowance dated Sep. 26, 2018.
Yacyshyn, et al. Tyrosine phosphatase beta regulates angiopoietin-Tie2 signaling in human endothelial cells. Angiogenesis. 2009;12(1):25-33. doi: 10.1007/s10456-008-9126-0. Epub Jan. 1, 2009.

* cited by examiner

SEQUENCE LISTING

```
<160> NUMBER OF SEQ ID NOS: 7

<210> SEQ ID NO 1
<211> LENGTH: 6045
<212> TYPE: DNA
<213> ORGANISM: Homo sapiens

<400> SEQUENCE: 1
atgctgagcc atggagccgg gttggccttg tggatcacac tgagcctgct gcagactgga      60
ctggcggagc cagagagatg taacttcacc ctggcggagt ccaaggcctc cagccattct     120
gtgtctatcc agtggagaat tttgggctca ccctgtaact ttagcctcat ctatagcagt     180
gacaccctgg gggccgcgtt gtgccctacc tttcggatag acaacaccac atacggatgt     240
aaccttcaag atttacaagc aggaaccatc tataacttca agattatttc tctggatgaa     300
gagagaactg tggtcttgca aacagatcct ttacctcctg ctaggtttgg agtcagtaaa     360
gagaagacga cttcaaccgg cttgcatgtt tggtggactc cttcttccgg aaaagtcacc     420
tcatatgagg tgcaattatt tgatgaaaat aaccaaaaga tacagggggt tcaaattcaa     480
gaaagtactt catggaatga atacactttt tcaatctca ctgctggtag taaatacaat     540
```

```
attgccatca cagctgtttc tggaggaaaa cgttcttttt cagtttatac caatggatca      600
acagtgccat ctccagtgaa agatattggt atttccacaa aagccaattc tctcctgatt      660
tcctggtccc atggttctgg aatgtggaa cgataccggc tgatgctaat ggataaaggg       720
atcctagttc atggcggtgt tgtggacaaa catgctactt cctatgcttt tcacgggctg      780
tcccctggct acctctacaa cctcactgtt atgactgagg ctgcagggct gcaaaactac      840
aggtggaaac tagtcaggac agcccccatg gaagtctcaa atctgaaggt gacaaatgat      900
ggcagtttga cctctctaaa agtcaaatgg caaagacctc ctggaaatgt ggattcttac      960
aatatcaccc tgtctcacaa agggaccatc aaggaatcca gagtattagc accttggatt     1020
actgaaactc actttaaaga gttagtcccc ggtcgacttt atcaagttac tgtcagctgt     1080
gtctctggtg aactgtctgc tcagaagatg gcagtgggca gaacatttcc agacaaagtt     1140
gcaaacctgg aggcaaacaa taatggcagg atgaggtctc ttgtagtgag ctggtcgccc     1200
cctgctggag actgggagca gtatcggatc ctactcttca atgattctgt ggtgctgctc     1260
aacatcactg tgggaaagga agaaacacag tatgtcatgg atgacacggg gctcgtaccg     1320
ggaagacagt atgaggtgga agtcattgtt gagagtggaa atttgaagaa ttctgagcgt     1380
tgccaaggca ggacagtccc cctggctgtc ctccagcttc gtgtcaaaca tgccaatgaa     1440
acctcactga gtatcatgtg gcagaccccct gtagcagaat gggagaaata catcatttcc     1500
ctagctgaca gagacctctt actgatccac aagtcactct ccaaagatgc caagaattc      1560 acttttactg acctggtgcc tggacgaaaa tacatggcta cagtcaccag tattagtgga     1620
gacttaaaaa attcctcttc agtaaaagga agaacagtgc ctgcccaagt gactgacttg     1680
catgtggcca accaaggaat gaccagtagt ctgtttacta actggaccca ggcacaagga     1740
gacgtagaat tttaccaagt cttactgatc catgaaaatg tggtcattaa aaatgaaagc     1800
atctccagtg agaccagcag atacagcttc cactctctca gtccggcag cctgtactcc      1860 gtggtggtaa caacagtgag tggagggatc tcttcccgac aagtggttgt ggagggaaga     1920
acagtccctt ccagtgtgag tggagtaacg gtgaacaatt ccggtcgtaa tgactacctc     1980 agcgttcct ggctcgtggc gcccggagat gtggataact atgaggtaac attgtctcat      2040
gacggcaagg tggttcagtc ccttgtcatt gccaagtctg tcagagaatg ttccttcagc     2100
tccctcaccc caggccgcct ctacaccgtg accataacta caaggagtgg caagtatgaa     2160
aatcactcct tcagccaaga gcggacagtg cctgacaaag tccagggagt cagtgttagc     2220
aactcagcca ggagtgacta tttaagggta tcctgggtgc atgccactgg agactttgat     2280
cactatgaag tcaccattaa aaacaaaaac aacttcattc aaactaaaag cattcccaag     2340
tcagaaaacg aatgtgtatt tgttcagcta gtccctggac ggttgtacag tgtcactgtt     2400
actacaaaaa gtgggacaata tgaagccaat gaacaaggga tgggagaac aattccagag     2460 cctgttaagg atctaacatt gcgcaacagg agcactgagg acttgcatgt gacttggtca     2520
ggagctaatg gggatgtcga ccaatatgag atccagctgc tcttcaatga catgaaagta     2580
tttcctcctt ttcaccttgt aaataccgca accgagtatc gatttacttc cctaacacca     2640
ggccgccaat acaaaattct tgtcttgacg attagcgggg atgtacagca gtcagccttc     2700
attgagggct tcacagttcc tagtgctgtc aaaaatattc acatttctcc caatggagca     2760
acagatagcc tgacggtgaa ctggactcct ggtggggag cgttgattc ctacacggtg       2820 tcggcattca ggcacagtca aaaggttgac tctcagacta ttccaagca cgtctttgag      2880 cacacgttcc acagactgga ggccggggag cagtaccaga tcatgattgc ctcagtcagc     2940
```

```
gggtccctga agaatcagat aaatgtggtt gggcggacag ttccagcatc tgtccaagga      3000
gtaattgcag acaatgcata cagcagttat tccttaatag taagttggca aaaagctgct      3060
ggtgtggcag aaagatatga tatcctgctt ctaactgaaa atggaatcct tctgcgcaac      3120
acatcagagc cagccaccac taagcaacac aaatttgaag atctaacacc aggcaagaaa      3180
tacaagatac agatcctaac tgtcagtgga ggcctcttta gcaaggaagc ccagactgaa      3240
ggccgaacag tcccagcagc tgtcaccgac ctgaggatca cagagaactc caccaggcac      3300
ctgtccttcc gctggaccgc ctcagagggg gagctcagct ggtacaacat cttttttgtac     3360 aacccagatg ggaatctcca ggagagagct caagttgacc cactagtcca gagcttctct      3420
ttccagaact tgctacaagg cagaatgtac aagatggtga ttgtaactca cagtggggag      3480
ctgtctaatg agtctttcat atttggtaga acagtcccag cctctgtgag tcatctcagg      3540
gggtccaatc ggaacacgac agacagcctt tggttcaact ggagtccagc ctctggggac      3600
tttgactttt atgagctgat tctctataat cccaatggca aaagaagga aaactggaaa       3660 gacaaggacc tgacggagtg gcggtttcaa ggccttgttc ctggaaggaa gtacgtgctg      3720
tgggtggtaa ctcacagtgg agatctcagc aataaagtca cagcggagag cagaacagct      3780
ccaagtcctc ccagtcttat gtcatttgct gacattgcaa acacatcctt ggccatcacg      3840
tggaaagggc ccccagactg gacagactac aacgactttg agctgcagtg gttgcccaga      3900
gatgcactta ctgtcttcaa cccctacaac aacagaaaat cagaaggacg cattgtgtat      3960
ggtcttcgtc cagggagatc ctatcaattc aacgtcaaga ctgtcagtgg tgattcctgg      4020
aaaacttaca gcaaaccaat tttggatct gtgaggacaa agcctgacaa gatacaaaac       4080
ctgcattgcc ggcctcagaa ctccacggcc attgcctgtt cttggatccc tcctgattct      4140
gactttgatg gttatagtat tgaatgccgg aaaatggaca cccaagaagt tgagttttcc      4200
agaaagctgg agaagaaaa atctctgctc aacatcatga tgctagtgcc cataagagg       4260 tacctggtgt ccatcaaagt gcagtcggcc ggcatgacca gcgaggtggt tgaagacagc      4320
actatcacaa tgatagaccg cccccctcct ccaccccac acattcgtgt gaatgaaaag      4380
gatgtgctaa ttagcaagtc ttccatcaac tttactgtca actgcagctg gttcagcgac      4440
accaatggag ctgtgaaata cttcacagtg gtggtgagag aggctgatgg cagtgatgag      4500
ctgaagccag aacagcagca ccctctccct tcctacctgg agtacaggca caatgcctcc      4560
attcgggtgt atcagactaa ttattttgcc agcaaatgtg ccgaaaatcc taacagcaac      4620
tccaagagtt ttaacattaa gcttggagca gagatggaga gcttaggtgg aaaacgcgat      4680
cccactcagc aaaaattctg tgatggacca ctgaagccac acactgccta cagaatcagc      4740
attcgagctt ttacacagct ctttgatgag gacctgaagg aattcacaaa gccactctat      4800
tcagacacat ttttttcttt acccatcact actgaatcag agcccttgtt tggagctatt      4860
gaaggtgtga gtgctggtct gttttttaatt ggcatgctag tggctgttgt tgccttattg      4920
atctgcagac agaaagtgag ccatggtcga gaaagaccct ctgcccgtct gagcattcgt      4980
agggatcgac cattatctgt ccacttaaac ctgggccaga aagtaaccg gaaaacttct       5040 tgtccaataa aaataaatca gtttgaaggg catttcatga agctacaggc tgactccaac      5100
taccttctat ccaaggaata cgaggagtta aaagacgtgg gccgaaacca gtcatgtgac      5160
attgcactct tgccggagaa tagagggaaa aatcgataca caatatatt gccctatgat      5220 gccacgcgag tgaagctctc caatgtagat gatgatcctt gctctgacta catcaatgcc      5280
```

-continued

```
agctacatcc ctggcaacaa cttcagaaga gaatacattg tcactcaggg accgcttcct    5340
ggcaccaagg atgacttctg gaaaatggtg tgggaacaaa acgttcacaa catcgtcatg    5400
gtgacccagt gtgttgagaa ggccgagta  aagtgtgacc attactggcc agcggaccag    5460
gattccctct actatgggga cctcatcctg cagatgctct cagagtccgt cctgcctgag    5520
tggaccatcc gggagtttaa gatatgcggt gaggaacagc ttgatgcaca cagactcatc    5580
cgccactttc actatacggt gtggccagac catggagtcc cagaaaccac ccagtctctg    5640
atccagtttg tgagaactgt cagggactac atcaacagaa gcccgggtgc tgggcccact    5700
gtggtgcact gcagtgctgg tgtgggtagg actggaacct ttattgcatt ggaccgaatc    5760
ctccagcagt tagactccaa agactctgtg acatttatg  gagcagtgca cgacctaaga    5820
cttcacaggg ttcacatggt ccagactgag tgtcagtatg tctacctaca tcagtgtgta    5880
agagatgtcc tcagagcaag aaagctacgg agtgaacaag aaaacccctt gtttccaatc    5940
tatgaaaatg tgaatccaga gtatcacaga gatccagtct attcaaggca ttgagaatgt    6000
acctgaagag ctcctggata aaaattattc actgtgtgat ttgtt               6045
```

<210> SEQ ID NO 2
<211> LENGTH: 1997
<212> TYPE: PRT
<213> ORGANISM: Homo sapiens

<400> SEQUENCE: 2

```
Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
                20                  25                  30

Glu Ser Lys Ala Ser Ser His Ser Val Ser Ile Gln Trp Arg Ile Leu
            35                  40                  45

Gly Ser Pro Cys Asn Phe Ser Leu Ile Tyr Ser Ser Asp Thr Leu Gly
        50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Arg Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Ser Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
    210                 215                 220

Gly Ser Gly Asn Val Glu Arg Tyr Arg Leu Met Leu Met Asp Lys Gly
225                 230                 235                 240
```

```
Ile Leu Val His Gly Val Val Asp Lys His Ala Thr Ser Tyr Ala
            245                 250                 255

Phe His Gly Leu Thr Pro Gly Tyr Leu Tyr Asn Leu Val Met Thr
            260                 265                 270

Glu Ala Ala Gly Leu Gln Asn Tyr Arg Trp Lys Leu Val Arg Thr Ala
            275                 280                 285

Pro Met Glu Val Ser Asn Leu Lys Val Thr Asn Asp Gly Ser Leu Thr
290                 295                 300

Ser Leu Lys Val Lys Trp Gln Arg Pro Gly Asn Val Asp Ser Tyr
305                 310                 315                 320

Asn Ile Thr Leu Ser His Lys Gly Thr Ile Lys Glu Ser Arg Val Leu
            325                 330                 335

Ala Pro Trp Ile Thr Glu Thr His Phe Lys Glu Leu Val Pro Gly Arg
            340                 345                 350

Leu Tyr Gln Val Thr Val Ser Cys Val Ser Gly Glu Leu Ser Ala Gln
            355                 360                 365

Lys Met Ala Val Gly Arg Thr Phe Pro Asp Lys Val Ala Asn Leu Glu
370                 375                 380

Ala Asn Asn Asn Gly Arg Met Arg Ser Leu Val Val Ser Trp Ser Pro
385                 390                 395                 400

Pro Ala Gly Asp Trp Glu Gln Tyr Arg Ile Leu Leu Phe Asn Asp Ser
            405                 410                 415

Val Val Leu Leu Asn Ile Thr Val Gly Lys Glu Thr Gln Tyr Val
            420                 425                 430

Met Asp Asp Thr Gly Leu Val Pro Gly Arg Gln Tyr Glu Val Glu Val
            435                 440                 445

Ile Val Glu Ser Gly Asn Leu Lys Asn Ser Glu Arg Cys Gln Gly Arg
450                 455                 460

Thr Val Pro Leu Ala Val Leu Gln Leu Arg Val Lys His Ala Asn Glu
465                 470                 475                 480

Thr Ser Leu Ser Ile Met Trp Gln Thr Pro Val Ala Glu Trp Glu Lys
            485                 490                 495

Tyr Ile Ile Ser Leu Ala Asp Arg Asp Leu Leu Leu Ile His Lys Ser
            500                 505                 510

Leu Ser Lys Asp Ala Lys Glu Phe Thr Phe Thr Asp Leu Val Pro Gly
            515                 520                 525

Arg Lys Tyr Met Ala Thr Val Thr Ser Ile Ser Gly Asp Leu Lys Asn
            530                 535                 540

Ser Ser Ser Val Lys Gly Arg Thr Val Pro Ala Gln Val Thr Asp Leu
545                 550                 555                 560

His Val Ala Asn Gln Gly Met Thr Ser Ser Leu Phe Thr Asn Trp Thr
            565                 570                 575

Gln Ala Gln Gly Asp Val Glu Phe Tyr Gln Val Leu Leu Ile His Glu
            580                 585                 590

Asn Val Val Ile Lys Asn Glu Ser Ile Ser Ser Glu Thr Ser Arg Tyr
            595                 600                 605

Ser Phe His Ser Leu Lys Ser Gly Ser Leu Tyr Ser Val Val Val Thr
            610                 615                 620

Thr Val Ser Gly Gly Ile Ser Ser Arg Gln Val Val Glu Gly Arg
625                 630                 635                 640

Thr Val Pro Ser Ser Val Ser Gly Val Thr Val Asn Asn Ser Gly Arg
            645                 650                 655

Asn Asp Tyr Leu Ser Val Ser Trp Leu Leu Ala Pro Gly Asp Val Asp
```

-continued

```
                660                 665                 670
Asn Tyr Glu Val Thr Leu Ser His Asp Gly Lys Val Val Gln Ser Leu
                675                 680                 685
Val Ile Ala Lys Ser Val Arg Glu Cys Ser Phe Ser Ser Leu Thr Pro
                690                 695                 700
Gly Arg Leu Tyr Thr Val Thr Ile Thr Thr Arg Ser Gly Lys Tyr Glu
705                 710                 715                 720
Asn His Ser Phe Ser Gln Glu Arg Thr Val Pro Asp Lys Val Gln Gly
                725                 730                 735
Val Ser Val Ser Asn Ser Ala Arg Ser Asp Tyr Leu Arg Val Ser Trp
                740                 745                 750
Val His Ala Thr Gly Asp Phe Asp His Tyr Glu Val Thr Ile Lys Asn
                755                 760                 765
Lys Asn Asn Phe Ile Gln Thr Lys Ser Ile Pro Lys Ser Glu Asn Glu
                770                 775                 780
Cys Val Phe Val Gln Leu Val Pro Gly Arg Leu Tyr Ser Val Thr Val
785                 790                 795                 800
Thr Thr Lys Ser Gly Gln Tyr Glu Ala Asn Glu Gln Gly Asn Gly Arg
                805                 810                 815
Thr Ile Pro Glu Pro Val Lys Asp Leu Thr Leu Arg Asn Arg Ser Thr
                820                 825                 830
Glu Asp Leu His Val Thr Trp Ser Gly Ala Asn Gly Asp Val Asp Gln
                835                 840                 845
Tyr Glu Ile Gln Leu Leu Phe Asn Asp Met Lys Val Phe Pro Pro Phe
                850                 855                 860
His Leu Val Asn Thr Ala Thr Glu Tyr Arg Phe Thr Ser Leu Thr Pro
865                 870                 875                 880
Gly Arg Gln Tyr Lys Ile Leu Val Leu Thr Ile Ser Gly Asp Val Gln
                885                 890                 895
Gln Ser Ala Phe Ile Glu Gly Phe Thr Val Pro Ser Ala Val Lys Asn
                900                 905                 910
Ile His Ile Ser Pro Asn Gly Ala Thr Asp Ser Leu Thr Val Asn Trp
                915                 920                 925
Thr Pro Gly Gly Gly Asp Val Asp Ser Tyr Thr Val Ser Ala Phe Arg
                930                 935                 940
His Ser Gln Lys Val Asp Ser Gln Thr Ile Pro Lys His Val Phe Glu
945                 950                 955                 960
His Thr Phe His Arg Leu Glu Ala Gly Glu Gln Tyr Gln Ile Met Ile
                965                 970                 975
Ala Ser Val Ser Gly Ser Leu Lys Asn Gln Ile Asn Val Val Gly Arg
                980                 985                 990
Thr Val Pro Ala Ser Val Gln Gly Val Ile Ala Asp Asn Ala Tyr Ser
                995                 1000                1005
Ser Tyr Ser Leu Ile Val Ser Trp Gln Lys Ala Ala Gly Val Ala
                1010                1015                1020
Glu Arg Tyr Asp Ile Leu Leu Leu Thr Glu Asn Gly Ile Leu Leu
                1025                1030                1035
Arg Asn Thr Ser Glu Pro Ala Thr Thr Lys Gln His Lys Phe Glu
                1040                1045                1050
Asp Leu Thr Pro Gly Lys Lys Tyr Lys Ile Gln Ile Leu Thr Val
                1055                1060                1065
Ser Gly Gly Leu Phe Ser Lys Glu Ala Gln Thr Glu Gly Arg Thr
                1070                1075                1080
```

```
Val Pro Ala Ala Val Thr Asp Leu Arg Ile Thr Glu Asn Ser Thr
    1085            1090                1095

Arg His Leu Ser Phe Arg Trp Thr Ala Ser Glu Gly Glu Leu Ser
    1100            1105                1110

Trp Tyr Asn Ile Phe Leu Tyr Asn Pro Asp Gly Asn Leu Gln Glu
    1115            1120                1125

Arg Ala Gln Val Asp Pro Leu Val Gln Ser Phe Ser Phe Gln Asn
    1130            1135                1140

Leu Leu Gln Gly Arg Met Tyr Lys Met Val Ile Val Thr His Ser
    1145            1150                1155

Gly Glu Leu Ser Asn Glu Ser Phe Ile Phe Gly Arg Thr Val Pro
    1160            1165                1170

Ala Ser Val Ser His Leu Arg Gly Ser Asn Arg Asn Thr Thr Asp
    1175            1180                1185

Ser Leu Trp Phe Asn Trp Ser Pro Ala Ser Gly Asp Phe Asp Phe
    1190            1195                1200

Tyr Glu Leu Ile Leu Tyr Asn Pro Asn Gly Thr Lys Lys Glu Asn
    1205            1210                1215

Trp Lys Asp Lys Asp Leu Thr Glu Trp Arg Phe Gln Gly Leu Val
    1220            1225                1230

Pro Gly Arg Lys Tyr Val Leu Trp Val Val Thr His Ser Gly Asp
    1235            1240                1245

Leu Ser Asn Lys Val Thr Ala Glu Ser Arg Thr Ala Pro Ser Pro
    1250            1255                1260

Pro Ser Leu Met Ser Phe Ala Asp Ile Ala Asn Thr Ser Leu Ala
    1265            1270                1275

Ile Thr Trp Lys Gly Pro Pro Asp Trp Thr Asp Tyr Asn Asp Phe
    1280            1285                1290

Glu Leu Gln Trp Leu Pro Arg Asp Ala Leu Thr Val Phe Asn Pro
    1295            1300                1305

Tyr Asn Asn Arg Lys Ser Glu Gly Arg Ile Val Tyr Gly Leu Arg
    1310            1315                1320

Pro Gly Arg Ser Tyr Gln Phe Asn Val Lys Thr Val Ser Gly Asp
    1325            1330                1335

Ser Trp Lys Thr Tyr Ser Lys Pro Ile Phe Gly Ser Val Arg Thr
    1340            1345                1350

Lys Pro Asp Lys Ile Gln Asn Leu His Cys Arg Pro Gln Asn Ser
    1355            1360                1365

Thr Ala Ile Ala Cys Ser Trp Ile Pro Pro Asp Ser Asp Phe Asp
    1370            1375                1380

Gly Tyr Ser Ile Glu Cys Arg Lys Met Asp Thr Gln Glu Val Glu
    1385            1390                1395

Phe Ser Arg Lys Leu Glu Lys Glu Lys Ser Leu Leu Asn Ile Met
    1400            1405                1410

Met Leu Val Pro His Lys Arg Tyr Leu Val Ser Ile Lys Val Gln
    1415            1420                1425

Ser Ala Gly Met Thr Ser Glu Val Val Glu Asp Ser Thr Ile Thr
    1430            1435                1440

Met Ile Asp Arg Pro Pro Pro Pro Pro His Ile Arg Val Asn
    1445            1450                1455

Glu Lys Asp Val Leu Ile Ser Lys Ser Ser Ile Asn Phe Thr Val
    1460            1465                1470
```

```
Asn Cys Ser Trp Phe Ser Asp Thr Asn Gly Ala Val Lys Tyr Phe
1475                1480                1485

Thr Val Val Val Arg Glu Ala Asp Gly Asn Asp Glu Leu Lys Pro
1490                1495                1500

Glu Gln Gln His Pro Leu Pro Ser Tyr Leu Glu Tyr Arg His Asn
1505                1510                1515

Ala Ser Ile Arg Val Tyr Gln Thr Asn Tyr Phe Ala Ser Lys Cys
1520                1525                1530

Ala Glu Asn Pro Asn Ser Asn Ser Lys Ser Phe Asn Ile Lys Leu
1535                1540                1545

Gly Ala Glu Met Glu Ser Leu Gly Gly Lys Cys Asp Pro Thr Gln
1550                1555                1560

Gln Lys Phe Cys Asp Gly Pro Leu Lys Pro His Thr Ala Tyr Arg
1565                1570                1575

Ile Ser Ile Arg Ala Phe Thr Gln Leu Phe Asp Glu Asp Leu Lys
1580                1585                1590

Glu Phe Thr Lys Pro Leu Tyr Ser Asp Thr Phe Phe Ser Leu Pro
1595                1600                1605

Ile Thr Thr Glu Ser Glu Pro Leu Phe Gly Ala Ile Glu Gly Val
1610                1615                1620

Ser Ala Gly Leu Phe Leu Ile Gly Met Leu Val Ala Val Val Ala
1625                1630                1635

Leu Leu Ile Cys Arg Gln Lys Val Ser His Gly Arg Glu Arg Pro
1640                1645                1650

Ser Ala Arg Leu Ser Ile Arg Arg Asp Arg Pro Leu Ser Val His
1655                1660                1665

Leu Asn Leu Gly Gln Lys Gly Asn Arg Lys Thr Ser Cys Pro Ile
1670                1675                1680

Lys Ile Asn Gln Phe Glu Gly His Phe Met Lys Leu Gln Ala Asp
1685                1690                1695

Ser Asn Tyr Leu Leu Ser Lys Glu Tyr Glu Glu Leu Lys Asp Val
1700                1705                1710

Gly Arg Asn Gln Ser Cys Asp Ile Ala Leu Leu Pro Glu Asn Arg
1715                1720                1725

Gly Lys Asn Arg Tyr Asn Asn Ile Leu Pro Tyr Asp Ala Thr Arg
1730                1735                1740

Val Lys Leu Ser Asn Val Asp Asp Pro Cys Ser Asp Tyr Ile
1745                1750                1755

Asn Ala Ser Tyr Ile Pro Gly Asn Asn Phe Arg Arg Glu Tyr Ile
1760                1765                1770

Val Thr Gln Gly Pro Leu Pro Gly Thr Lys Asp Asp Phe Trp Lys
1775                1780                1785

Met Val Trp Glu Gln Asn Val His Asn Ile Val Met Val Thr Gln
1790                1795                1800

Cys Val Glu Lys Gly Arg Val Lys Cys Asp His Tyr Trp Pro Ala
1805                1810                1815

Asp Gln Asp Ser Leu Tyr Tyr Gly Asp Leu Ile Leu Gln Met Leu
1820                1825                1830

Ser Glu Ser Val Leu Pro Glu Trp Thr Ile Arg Glu Phe Lys Ile
1835                1840                1845

Cys Gly Glu Glu Gln Leu Asp Ala His Arg Leu Ile Arg His Phe
1850                1855                1860

His Tyr Thr Val Trp Pro Asp His Gly Val Pro Glu Thr Thr Gln
```

```
                    1865                1870                1875

Ser Leu Ile Gln Phe Val Arg Thr Val Arg Asp Tyr Ile Asn Arg
         1880                1885                1890

Ser Pro Gly Ala Gly Pro Thr Val Val His Cys Ser Ala Gly Val
         1895                1900                1905

Gly Arg Thr Gly Thr Phe Ile Ala Leu Asp Arg Ile Leu Gln Gln
         1910                1915                1920

Leu Asp Ser Lys Asp Ser Val Asp Ile Tyr Gly Ala Val His Asp
         1925                1930                1935

Leu Arg Leu His Arg Val His Met Val Gln Thr Glu Cys Gln Tyr
         1940                1945                1950

Val Tyr Leu His Gln Cys Val Arg Asp Val Leu Arg Ala Arg Lys
         1955                1960                1965

Leu Arg Ser Glu Gln Glu Asn Pro Leu Phe Pro Ile Tyr Glu Asn
         1970                1975                1980

Val Asn Pro Glu Tyr His Arg Asp Pro Val Tyr Ser Arg His
         1985                1990                1995

<210> SEQ ID NO 3
<211> LENGTH: 1631
<212> TYPE: PRT
<213> ORGANISM: Homo sapiens

<400> SEQUENCE: 3

Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
                20                  25                  30

Glu Ser Lys Ala Ser Ser His Ser Val Ser Ile Gln Trp Arg Ile Leu
            35                  40                  45

Gly Ser Pro Cys Asn Phe Ser Leu Ile Tyr Ser Ser Asp Thr Leu Gly
        50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Arg Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Ser Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
    210                 215                 220

Gly Ser Gly Asn Val Glu Arg Tyr Arg Leu Met Leu Met Asp Lys Gly
225                 230                 235                 240
```

```
Ile Leu Val His Gly Val Val Asp Lys His Ala Thr Ser Tyr Ala
            245                 250                 255

Phe His Gly Leu Thr Pro Gly Tyr Leu Tyr Asn Leu Val Met Thr
        260                 265                 270

Glu Ala Ala Gly Leu Gln Asn Tyr Arg Trp Lys Leu Val Arg Thr Ala
    275                 280                 285

Pro Met Glu Val Ser Asn Leu Lys Val Thr Asn Asp Gly Ser Leu Thr
290                 295                 300

Ser Leu Lys Val Lys Trp Gln Arg Pro Gly Asn Val Asp Ser Tyr
305                 310                 315                 320

Asn Ile Thr Leu Ser His Lys Gly Thr Ile Lys Glu Ser Arg Val Leu
            325                 330                 335

Ala Pro Trp Ile Thr Glu Thr His Phe Lys Glu Leu Val Pro Gly Arg
        340                 345                 350

Leu Tyr Gln Val Thr Val Ser Cys Val Ser Gly Glu Leu Ser Ala Gln
    355                 360                 365

Lys Met Ala Val Gly Arg Thr Phe Pro Asp Lys Val Ala Asn Leu Glu
370                 375                 380

Ala Asn Asn Asn Gly Arg Met Arg Ser Leu Val Val Ser Trp Ser Pro
385                 390                 395                 400

Pro Ala Gly Asp Trp Glu Gln Tyr Arg Ile Leu Leu Phe Asn Asp Ser
            405                 410                 415

Val Val Leu Leu Asn Ile Thr Val Gly Lys Glu Thr Gln Tyr Val
        420                 425                 430

Met Asp Asp Thr Gly Leu Val Pro Gly Arg Gln Tyr Glu Val Glu Val
    435                 440                 445

Ile Val Glu Ser Gly Asn Leu Lys Asn Ser Glu Arg Cys Gln Gly Arg
450                 455                 460

Thr Val Pro Leu Ala Val Leu Gln Leu Arg Val Lys His Ala Asn Glu
465                 470                 475                 480

Thr Ser Leu Ser Ile Met Trp Gln Thr Pro Val Ala Glu Trp Glu Lys
            485                 490                 495

Tyr Ile Ile Ser Leu Ala Asp Arg Asp Leu Leu Leu Ile His Lys Ser
        500                 505                 510

Leu Ser Lys Asp Ala Lys Glu Phe Thr Phe Thr Asp Leu Val Pro Gly
    515                 520                 525

Arg Lys Tyr Met Ala Thr Val Thr Ser Ile Ser Gly Asp Leu Lys Asn
530                 535                 540

Ser Ser Ser Val Lys Gly Arg Thr Val Pro Ala Gln Val Thr Asp Leu
545                 550                 555                 560

His Val Ala Asn Gln Gly Met Thr Ser Ser Leu Phe Thr Asn Trp Thr
            565                 570                 575

Gln Ala Gln Gly Asp Val Glu Phe Tyr Gln Val Leu Leu Ile His Glu
        580                 585                 590

Asn Val Val Ile Lys Asn Glu Ser Ile Ser Ser Glu Thr Ser Arg Tyr
    595                 600                 605

Ser Phe His Ser Leu Lys Ser Gly Ser Leu Tyr Ser Val Val Val Thr
610                 615                 620

Thr Val Ser Gly Gly Ile Ser Ser Arg Gln Val Val Glu Gly Arg
625                 630                 635                 640

Thr Val Pro Ser Ser Val Ser Gly Val Thr Val Asn Asn Ser Gly Arg
            645                 650                 655

Asn Asp Tyr Leu Ser Val Ser Trp Leu Leu Ala Pro Gly Asp Val Asp
```

-continued

```
            660             665             670
Asn Tyr Glu Val Thr Leu Ser His Asp Gly Lys Val Val Gln Ser Leu
            675             680             685
Val Ile Ala Lys Ser Val Arg Glu Cys Ser Phe Ser Ser Leu Thr Pro
            690             695             700
Gly Arg Leu Tyr Thr Val Thr Ile Thr Thr Arg Ser Gly Lys Tyr Glu
705             710             715             720
Asn His Ser Phe Ser Gln Glu Arg Thr Val Pro Asp Lys Val Gln Gly
                725             730             735
Val Ser Val Ser Asn Ser Ala Arg Ser Asp Tyr Leu Arg Val Ser Trp
            740             745             750
Val His Ala Thr Gly Asp Phe Asp His Tyr Glu Val Thr Ile Lys Asn
            755             760             765
Lys Asn Asn Phe Ile Gln Thr Lys Ser Ile Pro Lys Ser Glu Asn Glu
            770             775             780
Cys Val Phe Val Gln Leu Val Pro Gly Arg Leu Tyr Ser Val Thr Val
785             790             795             800
Thr Thr Lys Ser Gly Gln Tyr Glu Ala Asn Glu Gln Gly Asn Gly Arg
                805             810             815
Thr Ile Pro Glu Pro Val Lys Asp Leu Thr Leu Arg Asn Arg Ser Thr
            820             825             830
Glu Asp Leu His Val Thr Trp Ser Gly Ala Asn Gly Asp Val Asp Gln
            835             840             845
Tyr Glu Ile Gln Leu Leu Phe Asn Asp Met Lys Val Phe Pro Pro Phe
            850             855             860
His Leu Val Asn Thr Ala Thr Glu Tyr Arg Phe Thr Ser Leu Thr Pro
865             870             875             880
Gly Arg Gln Tyr Lys Ile Leu Val Leu Thr Ile Ser Gly Asp Val Gln
                885             890             895
Gln Ser Ala Phe Ile Glu Gly Phe Thr Val Pro Ser Ala Val Lys Asn
            900             905             910
Ile His Ile Ser Pro Asn Gly Ala Thr Asp Ser Leu Thr Val Asn Trp
            915             920             925
Thr Pro Gly Gly Gly Asp Val Asp Ser Tyr Thr Val Ser Ala Phe Arg
            930             935             940
His Ser Gln Lys Val Asp Ser Gln Thr Ile Pro Lys His Val Phe Glu
945             950             955             960
His Thr Phe His Arg Leu Glu Ala Gly Glu Gln Tyr Gln Ile Met Ile
                965             970             975
Ala Ser Val Ser Gly Ser Leu Lys Asn Gln Ile Asn Val Val Gly Arg
            980             985             990
Thr Val Pro Ala Ser Val Gln Gly Val Ile Ala Asp Asn Ala Tyr Ser
            995             1000             1005
Ser Tyr Ser Leu Ile Val Ser Trp Gln Lys Ala Ala Gly Val Ala
            1010             1015             1020
Glu Arg Tyr Asp Ile Leu Leu Leu Thr Glu Asn Gly Ile Leu Leu
            1025             1030             1035
Arg Asn Thr Ser Glu Pro Ala Thr Thr Lys Gln His Lys Phe Glu
            1040             1045             1050
Asp Leu Thr Pro Gly Lys Lys Tyr Lys Ile Gln Ile Leu Thr Val
            1055             1060             1065
Ser Gly Gly Leu Phe Ser Lys Glu Ala Gln Thr Glu Gly Arg Thr
            1070             1075             1080
```

```
Val Pro Ala Ala Val Thr Asp Leu Arg Ile Thr Glu Asn Ser Thr
    1085            1090                1095

Arg His Leu Ser Phe Arg Trp Thr Ala Ser Glu Gly Glu Leu Ser
    1100            1105                1110

Trp Tyr Asn Ile Phe Leu Tyr Asn Pro Asp Gly Asn Leu Gln Glu
    1115            1120                1125

Arg Ala Gln Val Asp Pro Leu Val Gln Ser Phe Ser Phe Gln Asn
    1130            1135                1140

Leu Leu Gln Gly Arg Met Tyr Lys Met Val Ile Val Thr His Ser
    1145            1150                1155

Gly Glu Leu Ser Asn Glu Ser Phe Ile Phe Gly Arg Thr Val Pro
    1160            1165                1170

Ala Ser Val Ser His Leu Arg Gly Ser Asn Arg Asn Thr Thr Asp
    1175            1180                1185

Ser Leu Trp Phe Asn Trp Ser Pro Ala Ser Gly Asp Phe Asp Phe
    1190            1195                1200

Tyr Glu Leu Ile Leu Tyr Asn Pro Asn Gly Thr Lys Lys Glu Asn
    1205            1210                1215

Trp Lys Asp Lys Asp Leu Thr Glu Trp Arg Phe Gln Gly Leu Val
    1220            1225                1230

Pro Gly Arg Lys Tyr Val Leu Trp Val Val Thr His Ser Gly Asp
    1235            1240                1245

Leu Ser Asn Lys Val Thr Ala Glu Ser Arg Thr Ala Pro Ser Pro
    1250            1255                1260

Pro Ser Leu Met Ser Phe Ala Asp Ile Ala Asn Thr Ser Leu Ala
    1265            1270                1275

Ile Thr Trp Lys Gly Pro Pro Asp Trp Thr Asp Tyr Asn Asp Phe
    1280            1285                1290

Glu Leu Gln Trp Leu Pro Arg Asp Ala Leu Thr Val Phe Asn Pro
    1295            1300                1305

Tyr Asn Asn Arg Lys Ser Glu Gly Arg Ile Val Tyr Gly Leu Arg
    1310            1315                1320

Pro Gly Arg Ser Tyr Gln Phe Asn Val Lys Thr Val Ser Gly Asp
    1325            1330                1335

Ser Trp Lys Thr Tyr Ser Lys Pro Ile Phe Gly Ser Val Arg Thr
    1340            1345                1350

Lys Pro Asp Lys Ile Gln Asn Leu His Cys Arg Pro Gln Asn Ser
    1355            1360                1365

Thr Ala Ile Ala Cys Ser Trp Ile Pro Pro Asp Ser Asp Phe Asp
    1370            1375                1380

Gly Tyr Ser Ile Glu Cys Arg Lys Met Asp Thr Gln Glu Val Glu
    1385            1390                1395

Phe Ser Arg Lys Leu Glu Lys Glu Lys Ser Leu Leu Asn Ile Met
    1400            1405                1410

Met Leu Val Pro His Lys Arg Tyr Leu Val Ser Ile Lys Val Gln
    1415            1420                1425

Ser Ala Gly Met Thr Ser Glu Val Val Glu Asp Ser Thr Ile Thr
    1430            1435                1440

Met Ile Asp Arg Pro Pro Pro Pro Pro His Ile Arg Val Asn
    1445            1450                1455

Glu Lys Asp Val Leu Ile Ser Lys Ser Ser Ile Asn Phe Thr Val
    1460            1465                1470
```

```
Asn Cys Ser Trp Phe Ser Asp Thr Asn Gly Ala Val Lys Tyr Phe
    1475                1480                1485

Thr Val Val Val Arg Glu Ala Asp Gly Asn Asp Glu Leu Lys Pro
    1490                1495                1500

Glu Gln Gln His Pro Leu Pro Ser Tyr Leu Glu Tyr Arg His Asn
    1505                1510                1515

Ala Ser Ile Arg Val Tyr Gln Thr Asn Tyr Phe Ala Ser Lys Cys
    1520                1525                1530

Ala Glu Asn Pro Asn Ser Asn Ser Lys Ser Phe Asn Ile Lys Leu
    1535                1540                1545

Gly Ala Glu Met Glu Ser Leu Gly Gly Lys Cys Asp Pro Thr Gln
    1550                1555                1560

Gln Lys Phe Cys Asp Gly Pro Leu Lys Pro His Thr Ala Tyr Arg
    1565                1570                1575

Ile Ser Ile Arg Ala Phe Thr Gln Leu Phe Asp Glu Asp Leu Lys
    1580                1585                1590

Glu Phe Thr Lys Pro Leu Tyr Ser Asp Thr Phe Phe Ser Leu Pro
    1595                1600                1605

Ile Thr Thr Glu Ser Glu Pro Leu Phe Gly Ala Ile Glu Arg Gly
    1610                1615                1620

Arg His His His His His Gly
    1625                1630

<210> SEQ ID NO 4
<211> LENGTH: 1621
<212> TYPE: PRT
<213> ORGANISM: Homo sapiens

<400> SEQUENCE: 4

Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
                20                  25                  30

Glu Ser Lys Ala Ser Ser His Ser Val Ser Ile Gln Trp Arg Ile Leu
            35                  40                  45

Gly Ser Pro Cys Asn Phe Ser Leu Ile Tyr Ser Ser Asp Thr Leu Gly
        50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Arg Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Ser Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205
```

-continued

```
Ile Gly Ile Ser Thr Lys Ala Asn Ser Leu Leu Ile Ser Trp Ser His
    210                 215                 220
Gly Ser Gly Asn Val Glu Arg Tyr Arg Leu Met Leu Met Asp Lys Gly
225                 230                 235                 240
Ile Leu Val His Gly Val Val Asp Lys His Ala Thr Ser Tyr Ala
                245                 250                 255
Phe His Gly Leu Thr Pro Gly Tyr Leu Tyr Asn Leu Thr Val Met Thr
            260                 265                 270
Glu Ala Ala Gly Leu Gln Asn Tyr Arg Trp Lys Leu Val Arg Thr Ala
        275                 280                 285
Pro Met Glu Val Ser Asn Leu Lys Val Thr Asn Asp Gly Ser Leu Thr
290                 295                 300
Ser Leu Lys Val Lys Trp Gln Arg Pro Pro Gly Asn Val Asp Ser Tyr
305                 310                 315                 320
Asn Ile Thr Leu Ser His Lys Gly Thr Ile Lys Glu Ser Arg Val Leu
                325                 330                 335
Ala Pro Trp Ile Thr Glu Thr His Phe Lys Glu Leu Val Pro Gly Arg
            340                 345                 350
Leu Tyr Gln Val Thr Val Ser Cys Val Ser Gly Glu Leu Ser Ala Gln
        355                 360                 365
Lys Met Ala Val Gly Arg Thr Phe Pro Asp Lys Val Ala Asn Leu Glu
370                 375                 380
Ala Asn Asn Asn Gly Arg Met Arg Ser Leu Val Val Ser Trp Ser Pro
385                 390                 395                 400
Pro Ala Gly Asp Trp Glu Gln Tyr Arg Ile Leu Leu Phe Asn Asp Ser
                405                 410                 415
Val Val Leu Leu Asn Ile Thr Val Gly Lys Glu Glu Thr Gln Tyr Val
            420                 425                 430
Met Asp Asp Thr Gly Leu Val Pro Gly Arg Gln Tyr Glu Val Glu Val
        435                 440                 445
Ile Val Glu Ser Gly Asn Leu Lys Asn Ser Glu Arg Cys Gln Gly Arg
450                 455                 460
Thr Val Pro Leu Ala Val Leu Gln Leu Arg Val Lys His Ala Asn Glu
465                 470                 475                 480
Thr Ser Leu Ser Ile Met Trp Gln Thr Pro Val Ala Glu Trp Glu Lys
                485                 490                 495
Tyr Ile Ile Ser Leu Ala Asp Arg Asp Leu Leu Ile His Lys Ser
            500                 505                 510
Leu Ser Lys Asp Ala Lys Glu Phe Thr Phe Thr Asp Leu Val Pro Gly
        515                 520                 525
Arg Lys Tyr Met Ala Thr Val Thr Ser Ile Ser Gly Asp Leu Lys Asn
530                 535                 540
Ser Ser Ser Val Lys Gly Arg Thr Val Pro Ala Gln Val Thr Asp Leu
545                 550                 555                 560
His Val Ala Asn Gln Gly Met Thr Ser Ser Leu Phe Thr Asn Trp Thr
                565                 570                 575
Gln Ala Gln Gly Asp Val Glu Phe Tyr Gln Val Leu Leu Ile His Glu
            580                 585                 590
Asn Val Val Ile Lys Asn Glu Ser Ile Ser Ser Glu Thr Ser Arg Tyr
        595                 600                 605
Ser Phe His Ser Leu Lys Ser Gly Ser Leu Tyr Ser Val Val Val Thr
610                 615                 620
```

-continued

Thr Val Ser Gly Gly Ile Ser Ser Arg Gln Val Val Glu Gly Arg
625                 630                 635                 640

Thr Val Pro Ser Val Ser Gly Val Thr Val Asn Asn Ser Gly Arg
        645                 650                 655

Asn Asp Tyr Leu Ser Val Ser Trp Leu Leu Ala Pro Gly Asp Val Asp
            660                 665                 670

Asn Tyr Glu Val Thr Leu Ser His Asp Gly Lys Val Val Gln Ser Leu
            675                 680                 685

Val Ile Ala Lys Ser Val Arg Glu Cys Ser Phe Ser Ser Leu Thr Pro
690                 695                 700

Gly Arg Leu Tyr Thr Val Thr Ile Thr Thr Arg Ser Gly Lys Tyr Glu
705                 710                 715                 720

Asn His Ser Phe Ser Gln Glu Arg Thr Val Pro Asp Lys Val Gln Gly
                725                 730                 735

Val Ser Val Ser Asn Ser Ala Arg Ser Asp Tyr Leu Arg Val Ser Trp
                740                 745                 750

Val His Ala Thr Gly Asp Phe Asp His Tyr Glu Val Thr Ile Lys Asn
        755                 760                 765

Lys Asn Asn Phe Ile Gln Thr Lys Ser Ile Pro Lys Ser Glu Asn Glu
770                 775                 780

Cys Val Phe Val Gln Leu Val Pro Gly Arg Leu Tyr Ser Val Thr Val
785                 790                 795                 800

Thr Thr Lys Ser Gly Gln Tyr Glu Ala Asn Glu Gln Gly Asn Gly Arg
                805                 810                 815

Thr Ile Pro Glu Pro Val Lys Asp Leu Thr Leu Arg Asn Arg Ser Thr
        820                 825                 830

Glu Asp Leu His Val Thr Trp Ser Gly Ala Asn Gly Asp Val Asp Gln
835                 840                 845

Tyr Glu Ile Gln Leu Leu Phe Asn Asp Met Lys Val Phe Pro Pro Phe
850                 855                 860

His Leu Val Asn Thr Ala Thr Glu Tyr Arg Phe Thr Ser Leu Thr Pro
865                 870                 875                 880

Gly Arg Gln Tyr Lys Ile Leu Val Leu Thr Ile Ser Gly Asp Val Gln
                885                 890                 895

Gln Ser Ala Phe Ile Glu Gly Phe Thr Val Pro Ser Ala Val Lys Asn
        900                 905                 910

Ile His Ile Ser Pro Asn Gly Ala Thr Asp Ser Leu Thr Val Asn Trp
        915                 920                 925

Thr Pro Gly Gly Gly Asp Val Asp Ser Tyr Thr Val Ser Ala Phe Arg
        930                 935                 940

His Ser Gln Lys Val Asp Ser Gln Thr Ile Pro Lys His Val Phe Glu
945                 950                 955                 960

His Thr Phe His Arg Leu Glu Ala Gly Glu Gln Tyr Gln Ile Met Ile
                965                 970                 975

Ala Ser Val Ser Gly Ser Leu Lys Asn Gln Ile Asn Val Gly Arg
            980                 985                 990

Thr Val Pro Ala Ser Val Gln Gly  Val Ile Ala Asp Asn  Ala Tyr Ser
            995                 1000                1005

Ser Tyr  Ser Leu Ile Val Ser  Trp Gln Lys Ala Ala  Gly Val Ala
        1010                1015                1020

Glu Arg  Tyr Asp Ile Leu Leu  Leu Thr Glu Asn Gly  Ile Leu Leu
        1025                1030                1035

Arg Asn  Thr Ser Glu Pro Ala  Thr Thr Lys Gln His  Lys Phe Glu

```
            1040              1045              1050
Asp Leu Thr Pro Gly Lys Lys Tyr Lys Ile Gln Ile Leu Thr Val
        1055              1060              1065

Ser Gly Gly Leu Phe Ser Lys Glu Ala Gln Thr Glu Gly Arg Thr
    1070              1075              1080

Val Pro Ala Ala Val Thr Asp Leu Arg Ile Thr Glu Asn Ser Thr
        1085              1090              1095

Arg His Leu Ser Phe Arg Trp Thr Ala Ser Glu Gly Glu Leu Ser
    1100              1105              1110

Trp Tyr Asn Ile Phe Leu Tyr Asn Pro Asp Gly Asn Leu Gln Glu
        1115              1120              1125

Arg Ala Gln Val Asp Pro Leu Val Gln Ser Phe Ser Phe Gln Asn
    1130              1135              1140

Leu Leu Gln Gly Arg Met Tyr Lys Met Val Ile Val Thr His Ser
        1145              1150              1155

Gly Glu Leu Ser Asn Glu Ser Phe Ile Phe Gly Arg Thr Val Pro
    1160              1165              1170

Ala Ser Val Ser His Leu Arg Gly Ser Asn Arg Asn Thr Thr Asp
        1175              1180              1185

Ser Leu Trp Phe Asn Trp Ser Pro Ala Ser Gly Asp Phe Asp Phe
    1190              1195              1200

Tyr Glu Leu Ile Leu Tyr Asn Pro Asn Gly Thr Lys Lys Glu Asn
        1205              1210              1215

Trp Lys Asp Lys Asp Leu Thr Glu Trp Arg Phe Gln Gly Leu Val
    1220              1225              1230

Pro Gly Arg Lys Tyr Val Leu Trp Val Val Thr His Ser Gly Asp
        1235              1240              1245

Leu Ser Asn Lys Val Thr Ala Glu Ser Arg Thr Ala Pro Ser Pro
    1250              1255              1260

Pro Ser Leu Met Ser Phe Ala Asp Ile Ala Asn Thr Ser Leu Ala
    1265              1270              1275

Ile Thr Trp Lys Gly Pro Pro Asp Trp Thr Asp Tyr Asn Asp Phe
    1280              1285              1290

Glu Leu Gln Trp Leu Pro Arg Asp Ala Leu Thr Val Phe Asn Pro
        1295              1300              1305

Tyr Asn Asn Arg Lys Ser Glu Gly Arg Ile Val Tyr Gly Leu Arg
    1310              1315              1320

Pro Gly Arg Ser Tyr Gln Phe Asn Val Lys Thr Val Ser Gly Asp
        1325              1330              1335

Ser Trp Lys Thr Tyr Ser Lys Pro Ile Phe Gly Ser Val Arg Thr
    1340              1345              1350

Lys Pro Asp Lys Ile Gln Asn Leu His Cys Arg Pro Gln Asn Ser
        1355              1360              1365

Thr Ala Ile Ala Cys Ser Trp Ile Pro Pro Asp Ser Asp Phe Asp
    1370              1375              1380

Gly Tyr Ser Ile Glu Cys Arg Lys Met Asp Thr Gln Glu Val Glu
        1385              1390              1395

Phe Ser Arg Lys Leu Glu Lys Glu Lys Ser Leu Leu Asn Ile Met
    1400              1405              1410

Met Leu Val Pro His Lys Arg Tyr Leu Val Ser Ile Lys Val Gln
        1415              1420              1425

Ser Ala Gly Met Thr Ser Glu Val Val Glu Asp Ser Thr Ile Thr
    1430              1435              1440
```

```
Met Ile Asp Arg Pro Pro Pro Pro Pro His Ile Arg Val Asn
1445                1450                1455

Glu Lys Asp Val Leu Ile Ser Lys Ser Ser Ile Asn Phe Thr Val
1460                1465                1470

Asn Cys Ser Trp Phe Ser Asp Thr Asn Gly Ala Val Lys Tyr Phe
1475                1480                1485

Thr Val Val Val Arg Glu Ala Asp Gly Asn Asp Glu Leu Lys Pro
1490                1495                1500

Glu Gln Gln His Pro Leu Pro Ser Tyr Leu Glu Tyr Arg His Asn
1505                1510                1515

Ala Ser Ile Arg Val Tyr Gln Thr Asn Tyr Phe Ala Ser Lys Cys
1520                1525                1530

Ala Glu Asn Pro Asn Ser Asn Ser Lys Ser Phe Asn Ile Lys Leu
1535                1540                1545

Gly Ala Glu Met Glu Ser Leu Gly Gly Lys Cys Asp Pro Thr Gln
1550                1555                1560

Gln Lys Phe Cys Asp Gly Pro Leu Lys Pro His Thr Ala Tyr Arg
1565                1570                1575

Ile Ser Ile Arg Ala Phe Thr Gln Leu Phe Asp Glu Asp Leu Lys
1580                1585                1590

Glu Phe Thr Lys Pro Leu Tyr Ser Asp Thr Phe Phe Ser Leu Pro
1595                1600                1605

Ile Thr Thr Glu Ser Glu Pro Leu Phe Gly Ala Ile Glu
1610                1615                1620

<210> SEQ ID NO 5
<211> LENGTH: 6199
<212> TYPE: DNA
<213> ORGANISM: Mus musculus

<400> SEQUENCE: 5
ggcacgaggg cggctgccac ggcccttgag catcgccagc ccgagggta gcgcgctgcg      60 cccgcccgca gggcgcgctg agcgctcaac aagtggtacc cagaagtgcc ctggctggcc    120
tcccagcgag atgctgaggc atggagccct aacggccttg tggataacac tgagcgtcgt    180
gcagactgga gtggcagagc aagtgaaatg taacttcaca ctgttggagt ccagggtctc    240
tagcttgtca gcgtctatcc agtggaggac tttcgcgtca ccctgtaact ttagcctcat    300
ctacagcagt gatacctcgg ggcccatgtg gtgccatcct attcggatag acaactttac    360
ctacggatgt aaccccaagg atttacaagc agggaccgtc tataacttca ggattgtttc    420
tctggatgga gaagagagca ctctggtctt acagacagat ccgttgcctc ctgccaggtt    480
tgaagtcaat cgggagaaaa cagcatcaac caccctgcag gtccggtgga ctccctcttc    540
tggaaaagtc tcctggtatg aggtgcaatt atttgatcat acaatcaaa agatacaaga    600 agtccaagtt caagaaagta ccacctggag ccaatatact tttctgaacc tcactgaggg    660
taacagttac aaagttgcca tcacagctgt tcgggagaa aagcgctcct tccggtgta    720 tatcaatggc tctacagtac catctccagt gaaagatctt ggcatttccc ccaatcctaa    780
ttctctccta atttcctggt ctcgtggttc tgggaatgtg aacaataca ggctggtgct    840 aatggataaa ggggccatcg ttcaagacac aaacgtggac aggcgtgata cttcttatgc    900
ttttcacgag ctgaccctg ccacctcta caacctcact attgtcacca tggcctcggg    960
actgcaaaac tccaggtgga aactggtgag gaccgctccc atggaagtct caaatctgaa   1020
```

```
ggtgacaaat gacgggaggt tgacctctct aaatgtgaag tggcagaaac cccctgggga   1080
tgtagattcc tacagcatta ccctgtctca ccaagggacc atcaaagaat ccaaaacatt   1140
agcacctcct gttactgaaa ctcaatttaa ggacttagtc cctggacggc tttaccaagt   1200
gaccatcagc tgcatctctg gtgagctctc tgctgagaag tcagcagcgg ggagaacagt   1260
tccagaaaaa gtgaggaatc tggtttccta aacgagatt tggatgaagt cctttacagt   1320
gaactggacg cccctgctg gagattggga gcattatcgt atcgtgctct tcaatgaatc   1380
cttggtcttg ctcaacacca cagtgggaaa ggaagaaacg cactatgcct tggatggctt   1440
ggagctcata ccaggaagac agtatgagat agaagtcatt gttgagagcg aaatctgcg   1500 gaattccgag cgctgtcaag gcaggacagt accctggct gtcctccagc ttcgcgtcaa   1560
acacgctaac gaaacttcac tgggcatcac gtggcgggcc cctctaggcg aatgggagaa   1620
atacatcatt tcgttgatgg acagagagct cttggtcatc cacaagtcac tctccaaaga   1680
tgccaaagaa ttcactttta cagacctgat gcctggacgg aattacaagg ctactgtcac   1740
tagcatgagt ggagatttaa acagtcatc ttcaatcaaa ggaagaacag tgcctgccca   1800
ggtgactgac ctgcacgtca caaccaagg gatgaccagt agtctgttca ctaactggac   1860
aaaggcactg ggagatgtag agttctacca agttttactg atccatgaaa atgtggttgt   1920
caagaacgag agtgtttcca gtgataccag cagatacagc ttccgcgccc tgaaacccgg   1980
cagcctctac tccgtggtgg tgaccacggt gagtggaggg atctcctccc ggcaggtggt   2040
ggcggaagga agaacagtcc cgtccagcgt gagtggggtg acagtcaaca attctggccg   2100
gaatgactac ctcagcgttt cctggctgcc ggcgcctgga gaagtggatc actacgtggt   2160
gagcctctcc cacgagggca aggtggatca gttcctcatc atcgccaaat ctgtcagcga   2220
gtgttccttc agctccctca cccgggccg cctctacaac gtcactgtaa ccaccaagag   2280
cggcaattat gcaagccact ccttcaccga ggaacggaca gtgccagaca aggtccaggg   2340
aatcagtgtt agcaactctg ccagaagcga ctacttaaag gtgtcctggg tgcatgccac   2400
tggagacttt gaccactatg aagtcaccat caaaaacaga gaaagcttca ttcaaaccaa   2460
aaccatcccc aagtcagaaa atgagtgtga atttattgag ctggttcctg acgcctgta   2520 cagcgtcact gtcagtacaa agagtggaca atatgaagcc agtgaacagg ggacagggag   2580
aacgatccca gagcctgtga aggatctcac ccttctcaac aggagtacgg aggatctcca   2640
tgtgacttgg tcaagagcca atggggatgt tgatcagtac gaggtccagc tgctctcaa   2700 cgacatgaaa gtcttccctc atattcacct tgtgaacaca gcaactgagt ataagttcac   2760
ggcgctcacg ccggggcgcc attacaaaat cctcgtcctg accatcagtg gcgatgtcca   2820
gcagtcagcc ttcattgaag gcctcccagt tcccagcact gtcaaaaaca ttcacatttc   2880
tgccaatgga gccacggata ggctgatggt aacctggagc cctggtggcg gggatgtgga   2940
ctcctatgtg gtgtctgcat tcagacagga cgagaaggtt gactctcaga ccattcccaa   3000
gcatgcctcg gagcacacgt tccacaggct ggaggccgga gccaagtaca ggatcgccat   3060
tgtttctgtc agtgggtccc tgagaaacca gatagatgcg ctcggacaga cagtcccagc   3120
gtctgtccag ggagtcgtcg cagccaatgc atacagcagt aattccttaa cagtaagttg   3180
gcagaaagcc ttggtgtgg cagaaagata cgatatcctg cttctaaacg agaatgggct   3240
tcttttgagc aacgtgtcag agccagctac ggcaagacag cacaaatttg aagatctaac   3300
gccaggcaag aaatacaaga tgcagatcct gactgtcagc ggaggcctct tcagtaaaga   3360
atctcaggct gaaggccgaa cagtcccagc agctgtcacc aatctgagga tcacagagaa   3420
```

```
ctccagtaga tacctgtcct tcggctggac cgcctcggag ggtgaactca gctggtacaa   3480
catcttcctc tacaacccag acaggactct tcaggagcga gctcaagttg acccgctagt   3540
ccagagcttc tctttccaga acttgctaca aggcagaatg tacaagatgg tgattgtcac   3600
tcacagtggg gagctgtcca atgagtcatt tatattcggc agaacagttc ctgctgccgt   3660
gaaccatctc aaaggctccc atcggaacac gacagacagc ctgtggttca gctggagccc   3720
agcctccggg gactttgact tctatgagct gattctttac aatcccaacg gcacgaagaa   3780
ggagaactgg aaagaaaagg acgtgacaga gtggcgtttc caaggtcttg ttcctggaag   3840
gaaatacacc ctgtatgtgg tgactcacag tggggacctc agcaataaag tcacaggga   3900
gggcagaaca gccccaagtc ctccgagtct tttgtcattc gctgatgttg caaacacctc   3960
cttggctatc acctggaagg acccccagag ctggacagat tacaatgact ttgagctgca   4020
gtggttccct ggagatgcac ttaccatctt caacccctac agcagcagaa agtcagaagg   4080
acgcattgtg tacgggcttc acccagggag gtcctatcaa ttcagtgtca agactgtgag   4140
cggggactcc tggaaaacct acagcaaacc aatttctggg tctgtgagga caaagccaga   4200
caagatacaa aacctgcatt gccgccccca gaactccacg gccattgcct gctcttggat   4260
acctcctgac tccgactttg atggctacag cattgagtgc cgaaaaatgg atacccaaga   4320
aatcgagttt tccagaaagc tggagaaaga aaaatcactg ctcaacatca tgatgttagt   4380
acctcataag aggtacctgg tgtccatcaa ggtgcagtcg gccggcatga ccagtgaggt   4440
ggttgaagat agcaccatca ccatgataga ccgcccgcct caaccgcctc cacacatccg   4500
tgtgaatgaa aaggatgtgc taatcagcaa atcttccatc aactttactg tcaactgcag   4560
ctggttcagc gacaccaacg gagcggttaa atactttgct gtggtggtga gagaggccga   4620
cagcatggat gagttgaagc cagaacagca gcaccctctc ccttcctacc tggagtacag   4680
acacaacgcc tccatccgag tctaccgac caattatttt gccagcaaat gtgctgaaag   4740
tcccgacagc agttctaaaa gtttcaacat taagcttgga gcagagatgg acagcctcgg   4800
tggcaaatgt gatcccagtc agcagaaatt ctgtgatgga ccgctgaagc cacacaccgc   4860
ctacagaatc agcatccggg cttttacaca gctatttgac gaggacttga aagagttcac   4920
caaacctctc tactcggata cgttcttctc tatgcccatc accacagagt cagagccctt   4980
gtttggagtt attgaaggtg tgagtgctgg cctgtttcta attggcatgc tggtggccct   5040
tgttgccttc ttcatctgca gacagaaagc tagccacagc agggaaaggc catctgcccg   5100
gctcagcatt cgtagggacc ggcctttgtc tgtccatctg aatctgggcc agaaaggcaa   5160
ccggaaaact tcttgcccca taaagatcaa tcagtttgaa gggcatttca tgaagctgca   5220
ggcagactcc aactaccttc tatccaagga atatgaggac ttaaaagacg tgggtagaag   5280
ccagtcatgt gacattgccc tcttgcctga aatcgaggg aaaaatcgat acaacaacat   5340
attgccttat gatgcctcaa gagtgaagct ctcgaatgtc gatgacgacc cttgctctga   5400
ctacatcaac gccagctaca tccccggtaa caacttcaga cgagaataca tcgccactca   5460
gggaccgctt ccaggcacca aggatgactt ctggaagatg gcgtgggagc agaacgttca   5520
caacatcgtc atggtgaccc agtgtgttga aagggccga gtgaagtgtg accattactg   5580
gccagcagac caggaccccc tctactacgg tgatctcatc ctacagatgg tctcggagtc   5640
cgtgctcccc gagtggacca tcaggagtt taagatatgc agtgaagaac agttggatgc   5700
acacagactc atccgtcact ttcactacac ggtgtggcca gaccatgggg tcccagagac   5760
```

```
cacccagtcc ctgatccaat ttgtgaggac agtcagggac tacatcaaca gaagccccgg    5820
ggctgggccc accgtagtgc actgcagcgc tggtgtgggc agaacaggga cgttcgttgc    5880
cctggaccgg atcctccagc agttggactc taaggactcc gtggacattt atggggcagt    5940
gcatgaccta agactccaca gggttcacat ggtccagacc gagtgtcaat atgtgtatct    6000
gcatcagtgt gtaagagacg tcctcagagc aaagaaactg cggaacgagc aagagaaccc    6060
cctgtttccg atttatgaga atgtgaatcc agagtatcac agagatgcaa tctactcgag    6120
acattaagaa ttcacctgaa gatcccctgg ataaaagcgt tcactgtgt gactttaaaa     6180 aaaaaaaaaa aaaaaaaaa                                                  6199
```

<210> SEQ ID NO 6
<211> LENGTH: 1998
<212> TYPE: PRT
<213> ORGANISM: Mus musculus

<400> SEQUENCE: 6

```
Met Leu Arg His Gly Ala Leu Thr Ala Leu Trp Ile Thr Leu Ser Val
1               5                  10                  15

Val Gln Thr Gly Val Ala Glu Gln Val Lys Cys Asn Phe Thr Leu Leu
            20                  25                  30

Glu Ser Arg Val Ser Ser Leu Ser Ala Ser Ile Gln Trp Arg Thr Phe
        35                  40                  45

Ala Ser Pro Cys Asn Phe Ser Leu Ile Tyr Ser Ser Asp Thr Ser Gly
    50                  55                  60

Pro Met Trp Cys His Pro Ile Arg Ile Asp Asn Phe Thr Tyr Gly Cys
65                  70                  75                  80

Asn Pro Lys Asp Leu Gln Ala Gly Thr Val Tyr Asn Phe Arg Ile Val
                85                  90                  95

Ser Leu Asp Gly Glu Glu Ser Thr Leu Val Leu Gln Thr Asp Pro Leu
            100                 105                 110

Pro Pro Ala Arg Phe Glu Val Asn Arg Glu Lys Thr Ala Ser Thr Thr
        115                 120                 125

Leu Gln Val Arg Trp Thr Pro Ser Ser Gly Lys Val Ser Trp Tyr Glu
    130                 135                 140

Val Gln Leu Phe Asp His Asn Asn Gln Lys Ile Gln Glu Val Gln Val
145                 150                 155                 160

Gln Glu Ser Thr Thr Trp Ser Gln Tyr Thr Phe Leu Asn Leu Thr Glu
                165                 170                 175

Gly Asn Ser Tyr Lys Val Ala Ile Thr Ala Val Ser Gly Glu Lys Arg
            180                 185                 190

Ser Phe Pro Val Tyr Ile Asn Gly Ser Thr Val Pro Ser Pro Val Lys
        195                 200                 205

Asp Leu Gly Ile Ser Pro Asn Pro Asn Ser Leu Leu Ile Ser Trp Ser
    210                 215                 220

Arg Gly Ser Gly Asn Val Glu Gln Tyr Arg Leu Val Leu Met Asp Lys
225                 230                 235                 240

Gly Ala Ile Val Gln Asp Thr Asn Val Asp Arg Arg Asp Thr Ser Tyr
                245                 250                 255

Ala Phe His Glu Leu Thr Pro Gly His Leu Tyr Asn Leu Thr Ile Val
            260                 265                 270

Thr Met Ala Ser Gly Leu Gln Asn Ser Arg Trp Lys Leu Val Arg Thr
        275                 280                 285

Ala Pro Met Glu Val Ser Asn Leu Lys Val Thr Asn Asp Gly Arg Leu
```

-continued

```
             290                 295                 300
Thr Ser Leu Asn Val Lys Trp Gln Lys Pro Gly Asp Val Asp Ser
305                 310                 315                 320

Tyr Ser Ile Thr Leu Ser His Gln Gly Thr Ile Lys Glu Ser Lys Thr
                325                 330                 335

Leu Ala Pro Pro Val Thr Glu Thr Gln Phe Lys Asp Leu Val Pro Gly
                340                 345                 350

Arg Leu Tyr Gln Val Thr Ile Ser Cys Ile Ser Gly Glu Leu Ser Ala
                355                 360                 365

Glu Lys Ser Ala Ala Gly Arg Thr Val Pro Glu Lys Val Arg Asn Leu
        370                 375                 380

Val Ser Tyr Asn Glu Ile Trp Met Lys Ser Phe Thr Val Asn Trp Thr
385                 390                 395                 400

Pro Pro Ala Gly Asp Trp Glu His Tyr Arg Ile Val Leu Phe Asn Glu
                405                 410                 415

Ser Leu Val Leu Leu Asn Thr Thr Val Gly Lys Glu Glu Thr His Tyr
                420                 425                 430

Ala Leu Asp Gly Leu Glu Leu Ile Pro Gly Arg Gln Tyr Glu Ile Glu
                435                 440                 445

Val Ile Val Glu Ser Gly Asn Leu Arg Asn Ser Glu Arg Cys Gln Gly
        450                 455                 460

Arg Thr Val Pro Leu Ala Val Leu Gln Leu Arg Val Lys His Ala Asn
465                 470                 475                 480

Glu Thr Ser Leu Gly Ile Thr Trp Arg Ala Pro Leu Gly Glu Trp Glu
                485                 490                 495

Lys Tyr Ile Ile Ser Leu Met Asp Arg Glu Leu Leu Val Ile His Lys
                500                 505                 510

Ser Leu Ser Lys Asp Ala Lys Glu Phe Thr Phe Thr Asp Leu Met Pro
        515                 520                 525

Gly Arg Asn Tyr Lys Ala Thr Val Thr Ser Met Ser Gly Asp Leu Lys
                530                 535                 540

Gln Ser Ser Ser Ile Lys Gly Arg Thr Val Pro Ala Gln Val Thr Asp
545                 550                 555                 560

Leu His Val Asn Asn Gln Gly Met Thr Ser Ser Leu Phe Thr Asn Trp
                565                 570                 575

Thr Lys Ala Leu Gly Asp Val Glu Phe Tyr Gln Val Leu Leu Ile His
                580                 585                 590

Glu Asn Val Val Lys Asn Glu Ser Val Ser Ser Asp Thr Ser Arg
                595                 600                 605

Tyr Ser Phe Arg Ala Leu Lys Pro Gly Ser Leu Tyr Ser Val Val Val
        610                 615                 620

Thr Thr Val Ser Gly Gly Ile Ser Ser Arg Gln Val Val Ala Glu Gly
625                 630                 635                 640

Arg Thr Val Pro Ser Ser Val Ser Gly Val Thr Val Asn Asn Ser Gly
                645                 650                 655

Arg Asn Asp Tyr Leu Ser Val Ser Trp Leu Pro Ala Pro Gly Glu Val
                660                 665                 670

Asp His Tyr Val Val Ser Leu Ser His Glu Gly Lys Val Asp Gln Phe
                675                 680                 685

Leu Ile Ile Ala Lys Ser Val Ser Glu Cys Ser Phe Ser Ser Leu Thr
        690                 695                 700

Pro Gly Arg Leu Tyr Asn Val Thr Val Thr Thr Lys Ser Gly Asn Tyr
705                 710                 715                 720
```

```
Ala Ser His Ser Phe Thr Glu Glu Arg Thr Val Pro Asp Lys Val Gln
            725                 730                 735

Gly Ile Ser Val Ser Asn Ser Ala Arg Ser Asp Tyr Leu Lys Val Ser
            740                 745                 750

Trp Val His Ala Thr Gly Asp Phe Asp His Tyr Glu Val Thr Ile Lys
            755                 760                 765

Asn Arg Glu Ser Phe Ile Gln Thr Lys Thr Ile Pro Lys Ser Glu Asn
            770                 775                 780

Glu Cys Glu Phe Ile Glu Leu Val Pro Gly Arg Leu Tyr Ser Val Thr
785                 790                 795                 800

Val Ser Thr Lys Ser Gly Gln Tyr Glu Ala Ser Glu Gln Gly Thr Gly
            805                 810                 815

Arg Thr Ile Pro Glu Pro Val Lys Asp Leu Thr Leu Leu Asn Arg Ser
            820                 825                 830

Thr Glu Asp Leu His Val Thr Trp Ser Arg Ala Asn Gly Asp Val Asp
            835                 840                 845

Gln Tyr Glu Val Gln Leu Leu Phe Asn Asp Met Lys Val Phe Pro His
            850                 855                 860

Ile His Leu Val Asn Thr Ala Thr Glu Tyr Lys Phe Thr Ala Leu Thr
865                 870                 875                 880

Pro Gly Arg His Tyr Lys Ile Leu Val Leu Thr Ile Ser Gly Asp Val
            885                 890                 895

Gln Gln Ser Ala Phe Ile Glu Gly Leu Pro Val Pro Ser Thr Val Lys
            900                 905                 910

Asn Ile His Ile Ser Ala Asn Gly Ala Thr Asp Arg Leu Met Val Thr
            915                 920                 925

Trp Ser Pro Gly Gly Gly Asp Val Asp Ser Tyr Val Val Ser Ala Phe
            930                 935                 940

Arg Gln Asp Glu Lys Val Asp Ser Gln Thr Ile Pro Lys His Ala Ser
945                 950                 955                 960

Glu His Thr Phe His Arg Leu Glu Ala Gly Ala Lys Tyr Arg Ile Ala
            965                 970                 975

Ile Val Ser Val Ser Gly Ser Leu Arg Asn Gln Ile Asp Ala Leu Gly
            980                 985                 990

Gln Thr Val Pro Ala Ser Val Gln Gly Val Val Ala Ala Asn Ala Tyr
            995                1000                1005

Ser Ser Asn Ser Leu Thr Val Ser Trp Gln Lys Ala Leu Gly Val
            1010                1015                1020

Ala Glu Arg Tyr Asp Ile Leu Leu Leu Asn Glu Asn Gly Leu Leu
            1025                1030                1035

Leu Ser Asn Val Ser Glu Pro Ala Thr Ala Arg Gln His Lys Phe
            1040                1045                1050

Glu Asp Leu Thr Pro Gly Lys Lys Tyr Lys Met Gln Ile Leu Thr
            1055                1060                1065

Val Ser Gly Gly Leu Phe Ser Lys Glu Ser Gln Ala Glu Gly Arg
            1070                1075                1080

Thr Val Pro Ala Ala Val Thr Asn Leu Arg Ile Thr Glu Asn Ser
            1085                1090                1095

Ser Arg Tyr Leu Ser Phe Gly Trp Thr Ala Ser Glu Gly Glu Leu
            1100                1105                1110

Ser Trp Tyr Asn Ile Phe Leu Tyr Asn Pro Asp Arg Thr Leu Gln
            1115                1120                1125
```

```
Glu Arg Ala Gln Val Asp Pro Leu Val Gln Ser Phe Ser Phe Gln
1130             1135             1140

Asn Leu Leu Gln Gly Arg Met Tyr Lys Met Val Ile Val Thr His
1145             1150             1155

Ser Gly Glu Leu Ser Asn Glu Ser Phe Ile Phe Gly Arg Thr Val
1160             1165             1170

Pro Ala Ala Val Asn His Leu Lys Gly Ser His Arg Asn Thr Thr
1175             1180             1185

Asp Ser Leu Trp Phe Ser Trp Ser Pro Ala Ser Gly Asp Phe Asp
1190             1195             1200

Phe Tyr Glu Leu Ile Leu Tyr Asn Pro Asn Gly Thr Lys Lys Glu
1205             1210             1215

Asn Trp Lys Glu Lys Asp Val Thr Glu Trp Arg Phe Gln Gly Leu
1220             1225             1230

Val Pro Gly Arg Lys Tyr Thr Leu Tyr Val Val Thr His Ser Gly
1235             1240             1245

Asp Leu Ser Asn Lys Val Thr Gly Glu Gly Arg Thr Ala Pro Ser
1250             1255             1260

Pro Pro Ser Leu Leu Ser Phe Ala Asp Val Ala Asn Thr Ser Leu
1265             1270             1275

Ala Ile Thr Trp Lys Gly Pro Pro Asp Trp Thr Asp Tyr Asn Asp
1280             1285             1290

Phe Glu Leu Gln Trp Phe Pro Gly Asp Ala Leu Thr Ile Phe Asn
1295             1300             1305

Pro Tyr Ser Ser Arg Lys Ser Glu Gly Arg Ile Val Tyr Gly Leu
1310             1315             1320

His Pro Gly Arg Ser Tyr Gln Phe Ser Val Lys Thr Val Ser Gly
1325             1330             1335

Asp Ser Trp Lys Thr Tyr Ser Lys Pro Ile Ser Gly Ser Val Arg
1340             1345             1350

Thr Lys Pro Asp Lys Ile Gln Asn Leu His Cys Arg Pro Gln Asn
1355             1360             1365

Ser Thr Ala Ile Ala Cys Ser Trp Ile Pro Pro Asp Ser Asp Phe
1370             1375             1380

Asp Gly Tyr Ser Ile Glu Cys Arg Lys Met Asp Thr Gln Glu Ile
1385             1390             1395

Glu Phe Ser Arg Lys Leu Glu Lys Glu Lys Ser Leu Leu Asn Ile
1400             1405             1410

Met Met Leu Val Pro His Lys Arg Tyr Leu Val Ser Ile Lys Val
1415             1420             1425

Gln Ser Ala Gly Met Thr Ser Glu Val Val Glu Asp Ser Thr Ile
1430             1435             1440

Thr Met Ile Asp Arg Pro Pro Gln Pro Pro Pro His Ile Arg Val
1445             1450             1455

Asn Glu Lys Asp Val Leu Ile Ser Lys Ser Ser Ile Asn Phe Thr
1460             1465             1470

Val Asn Cys Ser Trp Phe Ser Asp Thr Asn Gly Ala Val Lys Tyr
1475             1480             1485

Phe Ala Val Val Val Arg Glu Ala Asp Ser Met Asp Glu Leu Lys
1490             1495             1500

Pro Glu Gln Gln His Pro Leu Pro Ser Tyr Leu Glu Tyr Arg His
1505             1510             1515

Asn Ala Ser Ile Arg Val Tyr Gln Thr Asn Tyr Phe Ala Ser Lys
```

-continued

```
            1520                1525                1530

Cys Ala Glu Ser Pro Asp Ser Ser Lys Ser Phe Asn Ile Lys
        1535                1540                1545

Leu Gly Ala Glu Met Asp Ser Leu Gly Gly Lys Cys Asp Pro Ser
1550                1555                1560

Gln Gln Lys Phe Cys Asp Gly Pro Leu Lys Pro His Thr Ala Tyr
1565                1570                1575

Arg Ile Ser Ile Arg Ala Phe Thr Gln Leu Phe Asp Glu Asp Leu
1580                1585                1590

Lys Glu Phe Thr Lys Pro Leu Tyr Ser Asp Thr Phe Phe Ser Met
1595                1600                1605

Pro Ile Thr Thr Glu Ser Glu Pro Leu Phe Gly Val Ile Glu Gly
1610                1615                1620

Val Ser Ala Gly Leu Phe Leu Ile Gly Met Leu Val Ala Leu Val
1625                1630                1635

Ala Phe Phe Ile Cys Arg Gln Lys Ala Ser His Ser Arg Glu Arg
1640                1645                1650

Pro Ser Ala Arg Leu Ser Ile Arg Arg Asp Arg Pro Leu Ser Val
1655                1660                1665

His Leu Asn Leu Gly Gln Lys Gly Asn Arg Lys Thr Ser Cys Pro
1670                1675                1680

Ile Lys Ile Asn Gln Phe Glu Gly His Phe Met Lys Leu Gln Ala
1685                1690                1695

Asp Ser Asn Tyr Leu Leu Ser Lys Glu Tyr Glu Asp Leu Lys Asp
1700                1705                1710

Val Gly Arg Ser Gln Ser Cys Asp Ile Ala Leu Leu Pro Glu Asn
1715                1720                1725

Arg Gly Lys Asn Arg Tyr Asn Asn Ile Leu Pro Tyr Asp Ala Ser
1730                1735                1740

Arg Val Lys Leu Ser Asn Val Asp Asp Asp Pro Cys Ser Asp Tyr
1745                1750                1755

Ile Asn Ala Ser Tyr Ile Pro Gly Asn Asn Phe Arg Arg Glu Tyr
1760                1765                1770

Ile Ala Thr Gln Gly Pro Leu Pro Gly Thr Lys Asp Asp Phe Trp
1775                1780                1785

Lys Met Ala Trp Glu Gln Asn Val His Asn Ile Val Met Val Thr
1790                1795                1800

Gln Cys Val Glu Lys Gly Arg Val Lys Cys Asp His Tyr Trp Pro
1805                1810                1815

Ala Asp Gln Asp Pro Leu Tyr Tyr Gly Asp Leu Ile Leu Gln Met
1820                1825                1830

Val Ser Glu Ser Val Leu Pro Glu Trp Thr Ile Arg Glu Phe Lys
1835                1840                1845

Ile Cys Ser Glu Glu Gln Leu Asp Ala His Arg Leu Ile Arg His
1850                1855                1860

Phe His Tyr Thr Val Trp Pro Asp His Gly Val Pro Glu Thr Thr
1865                1870                1875

Gln Ser Leu Ile Gln Phe Val Arg Thr Val Arg Asp Tyr Ile Asn
1880                1885                1890

Arg Ser Pro Gly Ala Gly Pro Thr Val Val His Cys Ser Ala Gly
1895                1900                1905

Val Gly Arg Thr Gly Thr Phe Val Ala Leu Asp Arg Ile Leu Gln
1910                1915                1920
```

-continued

Gln Leu Asp Ser Lys Asp Ser Val Asp Ile Tyr Gly Ala Val His
    1925            1930                1935

Asp Leu Arg Leu His Arg Val His Met Val Gln Thr Glu Cys Gln
    1940            1945                1950

Tyr Val Tyr Leu His Gln Cys Val Arg Asp Val Leu Arg Ala Lys
    1955            1960                1965

Lys Leu Arg Asn Glu Gln Glu Asn Pro Leu Phe Pro Ile Tyr Glu
    1970            1975                1980

Asn Val Asn Pro Glu Tyr His Arg Asp Ala Ile Tyr Ser Arg His
    1985            1990                1995

<210> SEQ ID NO 7
<211> LENGTH: 1619
<212> TYPE: PRT
<213> ORGANISM: Mus musculus

<400> SEQUENCE: 7

Met Leu Arg His Gly Ala Leu Thr Ala Leu Trp Ile Thr Leu Ser Val
1               5                   10                  15

Val Gln Thr Gly Val Ala Glu Gln Val Lys Cys Asn Phe Thr Leu Leu
                20                  25                  30

Glu Ser Arg Val Ser Ser Leu Ser Ala Ser Ile Gln Trp Arg Thr Phe
            35                  40                  45

Ala Ser Pro Cys Asn Phe Ser Leu Ile Tyr Ser Ser Asp Thr Ser Gly
        50                  55                  60

Pro Met Trp Cys His Pro Ile Arg Ile Asp Asn Phe Thr Tyr Gly Cys
65              70                  75                  80

Asn Pro Lys Asp Leu Gln Ala Gly Thr Val Tyr Asn Phe Arg Ile Val
                85                  90                  95

Ser Leu Asp Gly Glu Glu Ser Thr Leu Val Leu Gln Thr Asp Pro Leu
            100                 105                 110

Pro Pro Ala Arg Phe Glu Val Asn Arg Glu Lys Thr Ala Ser Thr Thr
        115                 120                 125

Leu Gln Val Arg Trp Thr Pro Ser Ser Gly Lys Val Ser Trp Tyr Glu
    130                 135                 140

Val Gln Leu Phe Asp His Asn Asn Gln Lys Ile Gln Glu Val Gln Val
145                 150                 155                 160

Gln Glu Ser Thr Thr Trp Ser Gln Tyr Thr Phe Leu Asn Leu Thr Glu
                165                 170                 175

Gly Asn Ser Tyr Lys Val Ala Ile Thr Ala Val Ser Gly Glu Lys Arg
            180                 185                 190

Ser Phe Pro Val Tyr Ile Asn Gly Ser Thr Val Pro Ser Pro Val Lys
        195                 200                 205

Asp Leu Gly Ile Ser Pro Asn Pro Asn Ser Leu Leu Ile Ser Trp Ser
    210                 215                 220

Arg Gly Ser Gly Asn Val Glu Gln Tyr Arg Leu Val Leu Met Asp Lys
225                 230                 235                 240

Gly Ala Ile Val Gln Asp Thr Asn Val Asp Arg Arg Asp Thr Ser Tyr
                245                 250                 255

Ala Phe His Glu Leu Thr Pro Gly His Leu Tyr Asn Leu Thr Ile Val
            260                 265                 270

Thr Met Ala Ser Gly Leu Gln Asn Ser Arg Trp Lys Leu Val Arg Thr
        275                 280                 285

Ala Pro Met Glu Val Ser Asn Leu Lys Val Thr Asn Asp Gly Arg Leu

```
                290                 295                 300
Thr Ser Leu Asn Val Lys Trp Gln Lys Pro Gly Asp Val Asp Ser
305                 310                 315                 320

Tyr Ser Ile Thr Leu Ser His Gln Gly Thr Ile Lys Glu Ser Lys Thr
                325                 330                 335

Leu Ala Pro Pro Val Thr Glu Thr Gln Phe Lys Asp Leu Val Pro Gly
                340                 345                 350

Arg Leu Tyr Gln Val Thr Ile Ser Cys Ile Ser Gly Glu Leu Ser Ala
                355                 360                 365

Glu Lys Ser Ala Ala Gly Arg Thr Val Pro Glu Lys Val Arg Asn Leu
        370                 375                 380

Val Ser Tyr Asn Glu Ile Trp Met Lys Ser Phe Thr Val Asn Trp Thr
385                 390                 395                 400

Pro Pro Ala Gly Asp Trp Glu His Tyr Arg Ile Val Leu Phe Asn Glu
                405                 410                 415

Ser Leu Val Leu Leu Asn Thr Thr Val Gly Lys Glu Glu Thr His Tyr
                420                 425                 430

Ala Leu Asp Gly Leu Glu Leu Ile Pro Gly Arg Gln Tyr Glu Ile Glu
                435                 440                 445

Val Ile Val Glu Ser Gly Asn Leu Arg Asn Ser Glu Arg Cys Gln Gly
        450                 455                 460

Arg Thr Val Pro Leu Ala Val Leu Gln Leu Arg Val Lys His Ala Asn
465                 470                 475                 480

Glu Thr Ser Leu Gly Ile Thr Trp Arg Ala Pro Leu Gly Glu Trp Glu
                485                 490                 495

Lys Tyr Ile Ile Ser Leu Met Asp Arg Glu Leu Leu Val Ile His Lys
                500                 505                 510

Ser Leu Ser Lys Asp Ala Lys Glu Phe Thr Phe Thr Asp Leu Met Pro
        515                 520                 525

Gly Arg Asn Tyr Lys Ala Thr Val Thr Ser Met Ser Gly Asp Leu Lys
                530                 535                 540

Gln Ser Ser Ser Ile Lys Gly Arg Thr Val Pro Ala Gln Val Thr Asp
545                 550                 555                 560

Leu His Val Asn Asn Gln Gly Met Thr Ser Ser Leu Phe Thr Asn Trp
                565                 570                 575

Thr Lys Ala Leu Gly Asp Val Glu Phe Tyr Gln Val Leu Leu Ile His
                580                 585                 590

Glu Asn Val Val Lys Asn Glu Ser Val Ser Ser Asp Thr Ser Arg
        595                 600                 605

Tyr Ser Phe Arg Ala Leu Lys Pro Gly Ser Leu Tyr Ser Val Val Val
                610                 615                 620

Thr Thr Val Ser Gly Gly Ile Ser Ser Arg Gln Val Val Ala Glu Gly
625                 630                 635                 640

Arg Thr Val Pro Ser Ser Val Ser Gly Val Thr Val Asn Asn Ser Gly
                645                 650                 655

Arg Asn Asp Tyr Leu Ser Val Ser Trp Leu Pro Ala Pro Gly Glu Val
                660                 665                 670

Asp His Tyr Val Val Ser Leu Ser His Glu Gly Lys Val Asp Gln Phe
                675                 680                 685

Leu Ile Ile Ala Lys Ser Val Ser Glu Cys Ser Phe Ser Ser Leu Thr
        690                 695                 700

Pro Gly Arg Leu Tyr Asn Val Thr Val Thr Thr Lys Ser Gly Asn Tyr
705                 710                 715                 720
```

```
Ala Ser His Ser Phe Thr Glu Glu Arg Thr Val Pro Asp Lys Val Gln
            725                 730                 735

Gly Ile Ser Val Ser Asn Ser Ala Arg Ser Asp Tyr Leu Lys Val Ser
            740                 745                 750

Trp Val His Ala Thr Gly Asp Phe Asp His Tyr Glu Val Thr Ile Lys
            755                 760                 765

Asn Arg Glu Ser Phe Ile Gln Thr Lys Thr Ile Pro Lys Ser Glu Asn
            770                 775             780

Glu Cys Glu Phe Ile Glu Leu Val Pro Gly Arg Leu Tyr Ser Val Thr
785             790                 795                 800

Val Ser Thr Lys Ser Gly Gln Tyr Glu Ala Ser Glu Gln Gly Thr Gly
                805                 810                 815

Arg Thr Ile Pro Glu Pro Val Lys Asp Leu Thr Leu Leu Asn Arg Ser
            820                 825                 830

Thr Glu Asp Leu His Val Thr Trp Ser Arg Ala Asn Gly Asp Val Asp
            835                 840                 845

Gln Tyr Glu Val Gln Leu Leu Phe Asn Asp Met Lys Val Phe Pro His
    850                 855                 860

Ile His Leu Val Asn Thr Ala Thr Glu Tyr Lys Phe Thr Ala Leu Thr
865                 870                 875                 880

Pro Gly Arg His Tyr Lys Ile Leu Val Leu Thr Ile Ser Gly Asp Val
                885                 890                 895

Gln Gln Ser Ala Phe Ile Glu Gly Leu Pro Val Pro Ser Thr Val Lys
                900                 905                 910

Asn Ile His Ile Ser Ala Asn Gly Ala Thr Asp Arg Leu Met Val Thr
            915                 920                 925

Trp Ser Pro Gly Gly Gly Asp Val Asp Ser Tyr Val Val Ser Ala Phe
    930                 935                 940

Arg Gln Asp Glu Lys Val Asp Ser Gln Thr Ile Pro Lys His Ala Ser
945                 950                 955                 960

Glu His Thr Phe His Arg Leu Glu Ala Gly Ala Lys Tyr Arg Ile Ala
                965                 970                 975

Ile Val Ser Val Ser Gly Ser Leu Arg Asn Gln Ile Asp Ala Leu Gly
            980                 985                 990

Gln Thr Val Pro Ala Ser Val Gln Gly Val Val Ala Ala Asn Ala Tyr
    995                 1000                1005

Ser Ser Asn Ser Leu Thr Val Ser Trp Gln Lys Ala Leu Gly Val
    1010                1015                1020

Ala Glu Arg Tyr Asp Ile Leu Leu Leu Asn Glu Asn Gly Leu Leu
    1025                1030                1035

Leu Ser Asn Val Ser Glu Pro Ala Thr Ala Arg Gln His Lys Phe
    1040                1045                1050

Glu Asp Leu Thr Pro Gly Lys Lys Tyr Lys Met Gln Ile Leu Thr
    1055                1060                1065

Val Ser Gly Gly Leu Phe Ser Lys Glu Ser Gln Ala Glu Gly Arg
    1070                1075                1080

Thr Val Pro Ala Ala Val Thr Asn Leu Arg Ile Thr Glu Asn Ser
    1085                1090                1095

Ser Arg Tyr Leu Ser Phe Gly Trp Thr Ala Ser Glu Gly Glu Leu
    1100                1105                1110

Ser Trp Tyr Asn Ile Phe Leu Tyr Asn Pro Asp Arg Thr Leu Gln
    1115                1120                1125
```

```
Glu Arg Ala Gln Val Asp Pro Leu Val Gln Ser Phe Ser Phe Gln
1130                1135                1140

Asn Leu Leu Gln Gly Arg Met Tyr Lys Met Val Ile Val Thr His
1145                1150                1155

Ser Gly Glu Leu Ser Asn Glu Ser Phe Ile Phe Gly Arg Thr Val
1160                1165                1170

Pro Ala Ala Val Asn His Leu Lys Gly Ser His Arg Asn Thr Thr
1175                1180                1185

Asp Ser Leu Trp Phe Ser Trp Ser Pro Ala Ser Gly Asp Phe Asp
1190                1195                1200

Phe Tyr Glu Leu Ile Leu Tyr Asn Pro Asn Gly Thr Lys Lys Glu
1205                1210                1215

Asn Trp Lys Glu Lys Asp Val Thr Glu Trp Arg Phe Gln Gly Leu
1220                1225                1230

Val Pro Gly Arg Lys Tyr Thr Leu Tyr Val Val Thr His Ser Gly
1235                1240                1245

Asp Leu Ser Asn Lys Val Thr Gly Glu Gly Arg Thr Ala Pro Ser
1250                1255                1260

Pro Pro Ser Leu Leu Ser Phe Ala Asp Val Ala Asn Thr Ser Leu
1265                1270                1275

Ala Ile Thr Trp Lys Gly Pro Pro Asp Trp Thr Asp Tyr Asn Asp
1280                1285                1290

Phe Glu Leu Gln Trp Phe Pro Gly Asp Ala Leu Thr Ile Phe Asn
1295                1300                1305

Pro Tyr Ser Ser Arg Lys Ser Glu Gly Arg Ile Val Tyr Gly Leu
1310                1315                1320

His Pro Gly Arg Ser Tyr Gln Phe Ser Val Lys Thr Val Ser Gly
1325                1330                1335

Asp Ser Trp Lys Thr Tyr Ser Lys Pro Ile Ser Gly Ser Val Arg
1340                1345                1350

Thr Lys Pro Asp Lys Ile Gln Asn Leu His Cys Arg Pro Gln Asn
1355                1360                1365

Ser Thr Ala Ile Ala Cys Ser Trp Ile Pro Pro Asp Ser Asp Phe
1370                1375                1380

Asp Gly Tyr Ser Ile Glu Cys Arg Lys Met Asp Thr Gln Glu Ile
1385                1390                1395

Glu Phe Ser Arg Lys Leu Glu Lys Glu Lys Ser Leu Leu Asn Ile
1400                1405                1410

Met Met Leu Val Pro His Lys Arg Tyr Leu Val Ser Ile Lys Val
1415                1420                1425

Gln Ser Ala Gly Met Thr Ser Glu Val Val Glu Asp Ser Thr Ile
1430                1435                1440

Thr Met Ile Asp Arg Pro Pro Gln Pro Pro His Ile Arg Val
1445                1450                1455

Asn Glu Lys Asp Val Leu Ile Ser Lys Ser Ser Ile Asn Phe Thr
1460                1465                1470

Val Asn Cys Ser Trp Phe Ser Asp Thr Asn Gly Ala Val Lys Tyr
1475                1480                1485

Phe Ala Val Val Val Arg Glu Ala Asp Ser Met Asp Glu Leu Lys
1490                1495                1500

Pro Glu Gln Gln His Pro Leu Pro Ser Tyr Leu Glu Tyr Arg His
1505                1510                1515

Asn Ala Ser Ile Arg Val Tyr Gln Thr Asn Tyr Phe Ala Ser Lys
```

-continued

```
            1520                1525                1530
Cys Ala Glu Ser Pro Asp Ser Ser Ser Lys Ser Phe Asn Ile Lys
        1535                1540                1545

Leu Gly Ala Glu Met Asp Ser Leu Gly Gly Lys Cys Asp Pro Ser
        1550                1555                1560

Gln Gln Lys Phe Cys Asp Gly Pro Leu Lys Pro His Thr Ala Tyr
        1565                1570                1575

Arg Ile Ser Ile Arg Ala Phe Thr Gln Leu Phe Asp Glu Asp Leu
        1580                1585                1590

Lys Glu Phe Thr Lys Pro Leu Tyr Ser Asp Thr Phe Phe Ser Met
        1595                1600                1605

Pro Ile Thr Thr Glu Ser Glu Pro Leu Phe Gly
        1610                1615
```

TREATMENT OF OCULAR DISEASE

CROSS-REFERENCE TO RELATED APPLICATION

This application is a Continuation of U.S. application Ser. No. 14/627,463 filed Feb. 20, 2015, now abandoned, which is a Continuation of U.S. application Ser. No. 13/652,154 filed Oct. 15, 2012, now U.S. Pat. No. 8,999,325 issued Apr. 7, 2015, which claims priority to U.S. Provisional Application Ser. No. 61/546,708 filed Oct. 13, 2011, the entirety of each of which is incorporated herein by reference.

INCORPORATION BY REFERENCE OF MATERIAL SUBMITTED ELECTRONICALLY

Incorporated by reference in its entirety is a computer-readable sequence listing submitted concurrently herewith and identified as follows: One 91.7 KB ASCII (Text) file named 45725710302 SL created on Mar. 17, 2017.

FIELD

Methods for treating eye diseases or conditions characterized by vascular instability, vascular leakage, and neovacularization such as ocular edema, ocular neovascularization, diabetic macular edema, age-related macular degeneration, choroidal neovascularization, diabetic retinopathy, retinal vein occlusion (central or branch), ocular ischemia, ocular trauma, surgery induced edema, and uveitis.

BACKGROUND

The eye comprises several structurally and functionally distinct vascular beds, which supply ocular components critical to the maintenance of vision. These include the retinal and choroidal vasculatures, which supply the inner and outer portions of the retina, respectively, and the limbal vasculature located at the periphery of the cornea. Injuries and diseases that impair the normal structure or function of these vascular beds are among the leading causes of visual impairment and blindness. For example, diabetic retinopathy is the most common disease affecting the retinal vasculature, and is the leading cause of vision loss among the working age population in the United States. Vascularization of the cornea secondary to injury or disease is yet another category of ocular vascular disease that can lead to severe impairment of vision.

"Macular degeneration" is a general medical term that applies to any of several disease syndromes, which involve a gradual loss or impairment of eyesight due to cell and tissue degeneration of the yellow macular region in the center of the retina. Macular degeneration is often characterized as one of two types, non-exudative (dry form) or exudative (wet form). Although both types are bilateral and progressive, each type may reflect different pathological processes. The wet form of age-related macular degeneration (AMD) is the most common form of choroidal neovascularization and a leading cause of blindness in the elderly. AMD affects millions of Americans over the age of 60, and is the leading cause of new blindness among the elderly.

Choroidal neovascular membrane (CNVM) is a problem that is related to a wide variety of retinal diseases, but is most commonly linked to age-related macular degeneration. With CNVM, abnormal blood vessels stemming from the choroid (the blood vessel-rich tissue layer just beneath the retina) grow up through the retinal layers. These new vessels are very fragile and break easily, causing blood and fluid to pool within the layers of the retina.

Diabetes (diabetes mellitus) is a metabolic disease caused by the inability of the pancreas to produce insulin or to use the insulin that is produced. The most common types of diabetes are type 1 diabetes (often referred to as Juvenile Onset Diabetes Mellitus) and type 2 diabetes (often referred to as Adult Onset Diabetes Mellitus). Type 1 diabetes results from the body's failure to produce insulin due to loss of insulin producing cells, and presently requires the person to inject insulin. Type 2 diabetes generally results from insulin resistance, a condition in which cells fail to use insulin properly. Type 2 diabetes may have a component of insulin deficiency as well.

Diabetes is directly responsible for a large number of disease conditions, including conditions or diseases of the eye including diabetic retinopathy (DR) and diabetic macular edema (DME) which are leading causes of vision loss and blindness in most developed countries. The increasing number of individuals with diabetes worldwide suggests that DR and DME will continue to be major contributors to vision loss and associated functional impairment for years to come.

Diabetic retinopathy is a complication of diabetes that results from damage to the blood vessels of the light-sensitive tissue at the back of the eye (retina). At first, diabetic retinopathy may cause no symptoms or only mild vision problems. Eventually, however, diabetic retinopathy can result in blindness. Diabetic retinopathy can develop in anyone who has type 1 diabetes or type 2 diabetes.

At its earliest stage, non-proliferative retinopathy, microaneurysms occur in the retina's tiny blood vessels. As the disease progresses, more of these blood vessels become damaged or blocked and these areas of the retina send signals into the regional tissue to grow new blood vessels for nourishment. This stage is called proliferative retinopathy. The new blood vessels grow along the retina and along the surface of the clear, vitreous gel that fills the inside of the eye.

By themselves, these blood vessels do not cause symptoms or vision loss. However, they have thin, fragile walls and without timely treatment, these new blood vessels can leak blood (whole blood or a constituent thereof) which can result in severe vision loss and even blindness.

Also, fluid can leak into the center of the macula, the part of the eye where sharp, straight-ahead vision occurs. The fluid and the associated protein begin to deposit on or under the macula causing the patient's central vision to become distorted. This condition is called macular edema. It can occur at any stage of diabetic retinopathy, although it is more likely to occur as the disease progresses. About half of the people with proliferative retinopathy also have macular edema.

Uveitis is a condition in which the uvea becomes inflamed. The eye is shaped much like a tennis ball, hollow on the inside with three different layers of tissue surrounding a central cavity. The outermost is the sclera (white coat of the eye) and the innermost is the retina. The middle layer between the sclera and the retina is called the uvea. The uvea contains many of the blood vessels that nourish the eye. Complications of uveitis include glaucoma, cataracts or new blood vessel formation (neovascularization).

The currently available interventions for exudative (wet form) macular degeneration, diabetic retinopathy, diabetic macular edema, choroidal neovascular membrane, complications from uveitis or ocular trauma, include laser photocoagulation therapy, low dose radiation (teletherapy) and surgical removal of neovascular membranes (vitrectomy). Laser therapy has had limited success and selected choroidal neovascular membranes which initially respond to laser therapy have high disease recurrence rates. There is also a potential loss of vision resulting from laser therapy. Low dose radiation has been applied ineffectively to induce regression of choroidal neovascularization. Recently, vascular endothelial growth factor (VEGF) antagonists, ranibizumab and aflibercept, have been approved for use in age-related macular degeneration, diabetic macular edema and retinal vein occlusion (RVO).

(RVO) is the most common retinal vascular disease after diabetic retinopathy. Depending on the area of retinal venous drainage effectively occluded, it is broadly classified as either central retinal vein occlusion (CRVO), hemispheric retinal vein occlusion (HRVO), or branch retinal vein occlusion (BRVO). It has been observed that each of these has two subtypes. Presentation of RVO in general is with variable painless visual loss with any combination of fundal findings consisting of retinal vascular tortuosity, retinal hemorrhages (blot and flame shaped), cotton wool spots, optic disc swelling and macular edema. In a CRVO, retinal hemorrhages will be found in all four quadrants of the fundus, while these are restricted to either the superior or inferior fundal hemisphere in a HRVO. In a BRVO, hemorrhages are largely localized to the area drained by the occluded in the retinal vein.

There is therefore a long felt and substantial need for methods of treating diseases of the eye which are characterized by vascular instability, vascular leakage and neovascularization.

SUMMARY

Disclosed are agents that bind to the extracellular portion and inhibit human protein tyrosine phosphatase beta (HPTPβ). Also disclosed are methods for treating eye diseases or conditions characterized by vascular instability, vascular leakage, and neovacularization such as ocular edema, ocular neovascularization, diabetic macular edema, age-related macular degeneration, choroidal neovascularization, diabetic retinopathy, retinal vein occlusion (central or branch), ocular ischemia, ocular trauma, surgery induced edema, and uveitis.

DETAILED DESCRIPTION

General Definitions

Figure 1:
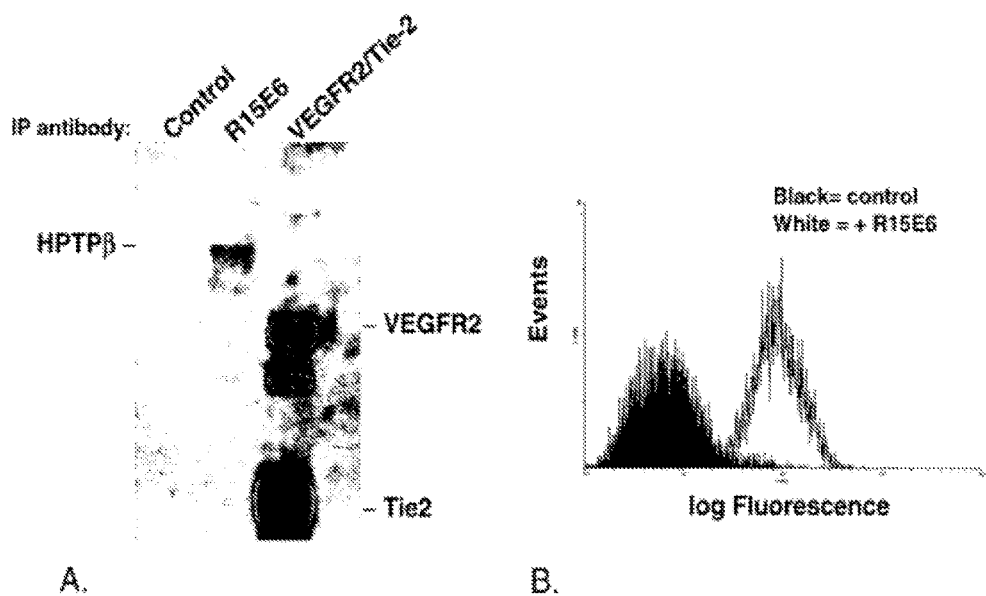
FIG. 1. The monoclonal antibody R15E6 recognizes Endogenous HPTPβ on endothelial cells. (Panel A) Endothelial cell lysates are immunoprecipitated with a control antibody (Lane 1), with R15E6 (Lane 2) or with a mixture of anti-Tie2 and anti-VEGFR2 antibodies (Lane 3). Immunoprecipitates are resolved by SDS-PAGE, transferred to a PVDF membrane and probed by western blot with a mixture of R15E6, anti-Tie2 and anti-VEGFR2 antibodies. A single major high molecular weight band consistent with HPTPβ is seen with R15E6 (Lane 2) and not with the control antibody (Lane 1) or the mixture of anti-Tie2 and anti-VEGFR2 (Lane 3). (Panel B) Endothelial cells are subjected to FACS analysis with R15E6 (white peak) or a control with no primary antibody (black peak). The robust shift in fluorescence indicates that R15E6 binds to HPTPβ on the surface of intact endothelial cells.

In this specification and in the claims that follow, reference will be made to a number of terms, which shall be defined to have the following meanings:

The term "HPTPβ-ECD binding agent" and "specific binding agent" are used interchangeably herein and refer to a molecule that specifically binds to the extracellular portion of HPTPβ, and variants and derivatives thereof, as defined herein, that inhibits the Tie2 dephosphorylase activity of HPTPβ.

"Agent" as used herein refers to a "HPTPβ binding agent" unless otherwise noted.

"Specifically binds HPTPβ-ECD" refers to the ability of a specific binding agent of the present invention to recognize and bind to an epitope of the extracellular domain of HPTPβ with higher affinity than to other related and/or unrelated molecules. Specific binding agents preferentially bind to HPTPβ in a complex mixture of proteins and/or macromolecules. The specific binding agent is preferably selective for HPTPβ. "Selective" means that the agent has significantly greater activity toward HPTPβ compared with other related and/or unrelated molecules, not that it is completely inactive with regard to other molecules. For example, a selective agent may show 10-fold, 100-fold, or 1000-fold selectivity toward HPTPβ than to other related or unrelated molecules.

The term "anti-HPTPβ-ECD antibodies" refers to antibodies or antibody fragments that bind to the extracellular domain of HPTPβ. Anti-HPTPβ-ECD antibodies are a type of HPTPβ-ECD binding agent as defined herein.

The term "VE-PTP" refers to the mouse ortholog of HPTPβ.

All percentages, ratios and proportions herein are by weight, unless otherwise specified. All temperatures are in degrees Celsius (° C.) unless otherwise specified.

Ranges may be expressed herein as from one particular value to another particular value, the endpoints are included in the range. For example for the range from "1 mg to 50 mg" includes the specific values 1 mg and 50 mg. The antecedent "about" indicates that the values are approximate. For example for the range from "about 1 mg to about 50 mg" indicates that the values are approximate values. Additionally, when such a range is expressed, the range includes the range "from 1 mg to 50 mg." It will be further understood that the endpoints of each of the ranges are significant both in relation to the other endpoint, and independently of the other endpoint. For example the range "from 1 mg to 50 mg", includes the range "from 30 mg to 40 mg."

"Effective amount" means an amount of an active agent or combination of agents effective to ameliorate or prevent the symptoms, or prolong the survival of the patient being treated. An effective amount may vary according to factors known in the art, such as the disease state, age, sex and weight of the human or animal being treated. Although particular dosage regimes may be described in examples herein, a person skilled in the art would appreciate that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount. Determination of a therapeutically effective amount is well within the capabilities of those skilled in the art, especially in light of the detailed disclosure provided herein.

As used herein the term "inhibit" or "inhibiting" refers to a statistically significant and measurable reduction in activity, preferably a reduction of at least about 10% versus control, more preferably a reduction of about 50% or more, still more preferably a reduction of about 80% or more.

As used herein the term "increase" or "increasing" refers to a statistically significant and measurable increase in activity, preferably an increase of at least about 10% versus control, more preferably an increase of about 50% or more, still more preferably an increase of about 80% or more.

"HPTP beta" or "HPTPβ" are used interchangeably herein and are abbreviations for human protein tyrosine phosphatase beta.

As used herein, "subject" means an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.) and birds. "Subject" can also include a mammal, such as a primate or a human. "Subject" and "patient" are used interchangeably herein. Preferably the subject is a human.

By "reduce" or other forms of the word, such as "reducing" or "reduction," is meant lowering of an event or characteristic (e.g., vascular leakage). It is understood that this is typically in relation to some standard or expected value, in other words it is relative, but that it is not always necessary for the standard or relative value to be referred to.

The terms "treatment", "treating", "treat" and the like, refer to obtaining a desired pharmacologic and/or physiologic effect such as mitigating a disease or a disorder in a host and/or reducing, inhibiting, or eliminating a particular characteristic or event associated with a disorder (e.g., ocular edema). Thus, the term "treatment" includes, preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state is completely avoided.

Unless otherwise specified, diabetic retinopathy includes all stages of non-proliferative retinopathy and proliferative retinopathy.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a", "an" and "the" include plural referents unless the context clearly dictates otherwise. Thus, for example, reference to "a composition" includes one composition or mixtures of two or more such compositions.

Optional" or "optionally" means that the subsequently described event or circumstance can or cannot occur, and that the description includes instances where the event or circumstance occurs and instances where it does not.

"Specifically binds HPTPβ" refers to the ability of an agent of the present invention to recognize and bind to an epitope of the extracellular domain of HPTPβ with higher affinity than to the other related and/or unrelated molecules. The agent is preferably selective for HPTPβ. "Specific" means that the agent has significantly greater activity toward HPTPβ compared with other related and/or unrelated molecules, not that it is completely inactive with regard to other molecules. For example, a selective agent may show 10-fold, 100-fold, or 1000-fold selectivity toward HPTPβ than to other related or unrelated molecule.

The term "epitope" refers to any portion of any molecule capable of being recognized by and bound by a agent at one or more of the agent's antigen binding regions. Epitopes usually consist of distinct, recognizable surface groupings such as amino acids, sugars, lipids, phosphoryl, or sulfonyl, and, in certain embodiments, may have specific three dimensional structural characteristics, and/or specific charge characteristics. Epitopes as used herein may be conformational or linear.

"Peptibody" is a molecule comprising an antibody Fc domain attached to at least one peptide. The production of peptibodies is generally described in WO2002/24782.

"Fragment" refers to a portion of an agent. A fragment may retain the desired biological activity of the agent and may be considered to be an agent itself. For example a truncated protein in which the amino terminus and/or carboxy terminus and/or an internal amino acid residue is deleted is a fragment of the protein and an Fab of an immunoglobulin molecule is a fragment of the immunoglobulin. Such fragments may also be connected to a another molecule by way of a direct connection (e.g. a peptide or disulfide bond) or by way of a linker.

"Protein" is used herein interchangeably with peptide and polypeptide.

Peptides of the present invention include, but are not limited to amino acid sequences having from about 3 to about 75 amino acids, or from about 5 to about 50 amino acids, or from about 10 to about 25 amino acids. Peptides may be naturally occurring or artificial amino acid sequences.

A protein of the invention may be obtained by methods well known in the art, for example, using standard direct peptide synthesizing techniques such as via solid-phase synthesis. If the gene sequence is known or can be deduced then the protein may be produced by standard recombinant methods. The proteins may be isolated or purified in a variety of ways known to one skilled in the art. Standard purification methods include precipitation with salts, electrophoretic, chromatographic techniques and the like.

Agents may be covalently or non-covalently conjugated to a vehicle. The term "vehicle" refers to a molecule that prevents degradation and/or increase half-life, reduces toxicity, reduces immunogenicity, or increases biological activity of the agent. Exemplary vehicles include, but are not limited, Fc domains of immunoglobulins and polymers, for example: polyethylene glycol (PEG), polylysine, dextran, a lipid, a cholesterol group (such as a steroid); a carbohydrate or oligosaccharide; or any natural or synthetic protein, or peptide that binds to a salvage receptor.

"Derivatives" include those binding agents that have been chemically modified in some manner distinct from insertion, deletion, or substitution variants. For example, wherein the binding agent is a protein, the carboxyl terminus may be capped with an amino group, such as $NH_2$.

In some embodiments one or more molecules are linked together to form the agent. For example antibody fragments may be connected by a linker. In general, the chemical structure of the linker is not critical as it serves primarily as a space. In one embodiment, the linker is made of amino acids linked together by way of peptide bonds. In another embodiment, the linker is a non-peptide linker such as a non-sterically hindering $C_1$-$C_6$ alkyl group. In another embodiment, the linker is a PEG linker. It will further be appreciated that the linker can be inserted in a number of locations on the molecule.

Variants of an agent are included within the scope of the present invention. "Variant" or "Variants" as used herein means an agent having a protein or nucleotide sequence which is substantially similar to the protein or nucleotide sequence of the non-variant agent and which shares a similar activity of the non-variant agent. A protein or nucleotide sequence may be altered in various ways to yield a variant encompassed by the present invention, including substitutions, deletions, truncations, insertions and other modifications. Methods for such manipulations are well known in the art. See, for example, Current Protocols in Molecular Biology (and updates) Ausubel et al., Eds (1996), John Wiley and Sons, New York: Methods in Molecular Biology, Vol. 182, In vitro Mutagenesis Protocols, $2^{nd}$ Edition, Barman Ed. (2002), Humana Press, and the references cited therein. For example, variants include peptides and polypeptides wherein amino acid residues are inserted into, deleted from and/or substituted into the known amino acid sequence for the binding agent. In one embodiment, the substitution of the amino acid is conservative in that it minimally alters the biochemical properties of the variant. In other embodiments, the variant may be an active fragment of a full-length protein, a chemically modified protein, a protein modified by addition of affinity or epitope tags, or fluorescent or other labeling moieties, whether accomplished by in vivo or in vitro enzymatic treatment of the protein, by chemical modification, or by the synthesis of the protein using modified amino acids.

Fusions proteins are also contemplated herein. Using known methods, one of skill in the art would be able to make fusion proteins of the proteins of the invention; that, while different from native form, may be useful. For example, the fusion partner may be a signal (or leader) polypeptide sequence that co-translationally or post-translationally directs transfer of the protein from its site of synthesis to another site (e.g., the yeast alpha-factor leader). Alternatively, it may be added to facilitate purification or identification of the protein of the invention (e.g., poly-His, Flag peptide, or fluorescent proteins).

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The techniques and procedures are generally performed according to conventional methods known in the art and as described in various general and more specific references that are cited and discussed throughout the present specification. Unless specific definitions are provided, the nomenclature utilized in connection with, and the laboratory procedures and techniques of, analytical chemistry, synthetic organic chemistry, and medicinal and pharmaceutical chemistry described herein are those known and commonly used in the art. Standard techniques may be used for chemical syntheses, chemical analyses, pharmaceutical preparation, formulation, delivery and treatment of patients.

Sequence Listing

TABLE 1

| | |
|---|---|
| SEQ ID NO: 1 | Full length Human HPTPβ nucleotide sequence (X54131) |
| SEQ ID NO: 2 | Full length Human HPTPβ amino acid sequence (P23467) |
| SEQ ID NO: 3 | Extracellular Portion of Human HPTPβ with (His)$_6$Gly Tag |
| SEQ ID NO: 4 | Extracellular Portion of Human HPTPβ |
| SEQ ID NO: 5 | Full length mouse VE-PTP nucleotide sequence |
| SEQ ID NO: 6 | Full length mouse VE-PTP amino acid sequence |
| SEQ ID NO: 7 | Extracellular portion of mouse VE-PTP amino acid sequence |

HPTPβ-ECD Binding Agents

Agents useful in the present invention include, but are not limited to, antibodies, proteins, darpins, peptides, aptamers, adnectins, peptibodies, or nucleic acids that bind specifically to the extracellular portion of HPTPβ and inhibit at least one phosphatase activity of HPTPβ. As used herein, "phosphatase activity" includes enzymatic activity and biologic activity where biological activity is measured by assessing Tie2 phosphorylation.

Agents useful in the present invention further include: antibodies, or antigen binding fragments thereof which bind to the extracellular portion of HPTPβ wherein the antibody or antigen-binding fragment inhibits at least one phosphatase activity of HPTPβ. These agents include monoclonal and polyclonal antibodies. An agent may be a fragment of an antibody, wherein the fragment comprises the heavy and light chain variable regions, or the fragment is an F(ab')$_2$, or the fragment is a dimer or trimer of an Fab, Fv, scFv, or a dia-, tria-, or tetrabody derived from the antibody.

For example, the agent may be, without limitation, an antibody or antibody fragment that binds the extracellular portion of HPTPβ; or in particular an antibody that binds an FN3 repeat of HPTPβ, or more specifically an antibody that binds the first FN3 repeat of HPTPβ.

Agents further include: the monoclonal antibody R15E6 which is described in U.S. Pat. No. 7,973,142, which is hereby incorporated in its entirety. (The mouse hybridoma, Balbc spleen cells (B cells) which may be used to produce the antibody are deposited with American Type Culture Collection (ATCC), P.O. Box 1549, Manassas, Va. 20108 USA on 4 May 2006, assigned ATCC No. PTA-7580) (Referred to herein as R15E6)), antibodies having the same or substantially the same biological characteristics of R15E6; antibody fragments of R15E6, wherein the fragment comprises the heavy and light chain variable regions; an F(ab')2 of R15E6; dimers or trimers of an Fab, Fv, scFv; and dia-, tria-, or tetrabodies derived from R15E6.

In particular, an agent suitable for use in the present invention is an antibody, antibody fragment, variant or derivatives thereof, either alone or in combination with other amino acid sequences, provided by known techniques. Such techniques include, but are not limited to enzymatic cleavage, chemical cleavage, peptide synthesis or recombinant techniques. The invention further embraces derivative agents, e.g. peptibodies.

Thus, one embodiment of an HPTPβ-ECD binding agent is an antibody, another embodiment is a protein, yet another embodiment is a peptide, and another embodiment is a darpin, another embodiment is an aptamer, another embodiment is a peptibody, still another embodiment is an adnectin, another embodiment is a nucleic acid. In some embodiments the HPTPβ-ECD binding agent is a monoclonal antibody, or is a polyclonal antibody. In particular embodiments, the HPTPβ-ECD binding agent is an antibody fragment that is capable of binding to HPTPβ-ECD. Preferably the HPTPβ-ECD binding agent is an antibody, or an antibody fragment, including but not limited to, an F(ab')$_2$, an Fab, a dimer of an Fab, an Fv, a dimer of an Fv, a scFv, a dimer of a scFv, a dimer an Fab, an Fv, a dimer of an Fv, a scFv, a dimer of a scFv, a trimer of an Fab, a trimer of an Fv, a trimer of a scFv, minibodies, a diabody , a triabody, a tetrabody, a linear antibody, a protein, a peptide, an aptamer, a peptibody, an adnectin, or a nucleic acid, that binds to the extracellular portion of HPTPβ. In certain embodiments the HPTPβ-ECD binding agent is and F(ab')$_2$ of a monoclonal antibody. In some embodiments the HPTPβ-ECD binding agent comprises a plurality of HPTPβ-ECD binding sites, for example where the HPTPβ-ECD binding agent is an intact antibody or an F(ab')$_2$, or a dimer of an Fab, or a trimer of an Fab. For example, in some embodiments an HPTPβ-ECD binding agent is able to bind to two HPTPβ molecules simultaneously at the same or different epitope, thereby bringing the two HPTPβ molecules into close proximity with one and other. In other embodiments the HPTPβ-ECD binding agent is able to bind to three HPTPβ molecules simultaneously at the same or different epitope, thereby bringing the three HPTPβ molecules into close proximity with one and other. In another embodiment, the HPTPβ-ECD binding agent is the monoclonal antibody produced by hybridoma cell line ATCC No. PTA-7580. In yet another embodiment, the HPTPβ-ECD binding agent is an antigen binding fragment of the monoclonal antibody produced by hybridoma cell line ATCC No. PTA-7580. In still another embodiment, the HPTPβ-ECD binding agent is an antibody having the same or substantially the same biological characteristics the monoclonal antibody produced by hybridoma cell line ATCC No. PTA-7580 or an antigen binding fragment thereof.

Any of the embodiments of HPTPβ-ECD binding agents disclosed in the present application, may be covalently or non-covalently conjugated to a vehicle. The term "vehicle" refers to a molecule that affects a biological property of an agent. For example, a vehicle may prevent degradation, and/or increase half-life, absorption, reduce toxicity, reduce immunogenicity, or increase biological activity of the agent. Exemplary vehicles include, but are not limited to, Fc domains of immunoglobulins; polymers, for example: polyethylene glycol (PEG), polylysine, dextran; lipids; cholesterol groups (such as a steroid); carbohydrates, dendrimers, oligosaccharides, or peptides that binds to a salvage receptor. In some embodiments the vehicle is polyethylene glycol (PEG), in other embodiments the vehicle is polylysine, in yet other embodiments the vehicle is dextran, in still other embodiments the vehicle is a lipid Water soluble polymer attachments, such as polyethylene glycol, polyoxyethylene glycol, or polypropylene glycol, as described U.S. Pat. Nos. 4,640,835; 4,496,689; 4,301,144; 4,670,417; 4,791,192; and 4,179,337, which are incorporated herein in their entirety. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers. Particularly preferred are peptibodies covalently modified with polyethylene glycol (PEG) subunits. Water soluble polymers may be bonded at specific positions, for example at the amino terminus of the peptibodies, or randomly attached to one or more side chains of the polypeptide. The use of PEG for improving the therapeutic capacity for agents, e.g. peptibodies, and for humanized antibodies in particular, is described in U.S. Pat. No. 6,133,426. The invention also contemplates derivatizing the peptide and/or vehicle portion of the agents. Such derivatives may improve the solubility, absorption, biological half-life, and the like of the agents. The moieties may alternatively eliminate or attenuate any undesirable side-effect of the agents and the like.

The term "antibody" (Ab) as used herein includes monoclonal antibodies, polyclonal antibodies, multi-specific antibodies (e.g. bispecific antibodies), single chain antibodies, e.g., antibodies from llama and camel, antibody fragments, e.g., variable regions and/or constant region fragments, so long as they exhibit a desired biological activity, e.g., antigen-binding activity. The term "immunoglobulin" (Ig) is used interchangeably with "antibody" herein.

An "antigen binding fragment" as used herein is a fragment of an agent that binds to a portion of HPTPβ and inhibits the activity of HPTPβ.

An "isolated antibody" is an antibody which has been identified, and/or separated, and/or recovered from its natural environment.

The basic four-chain antibody unit is a heterotetrameric glycoprotein composed of two identical light (L) chains and two identical heavy (H) chains (an IgM antibody consists of 5 of the basic heterotetramer units along with an additional polypeptide called J chain, and therefore contain 10 antigen binding sites, while secreted IgA antibodies may polymerize to form polyvalent assemblages comprising 2-5 of the basic 4-chain units along with J chain). In the case of IgGs, the four-chain unit is generally about 150 kilo Daltons (kDa). Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the alpha and gamma chains and four $C_H$ domains for mu and epsilon isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, 1994, page 71 and Chapter 6.

The L chain from any vertebrate species may be assigned to one of two clearly distinct types, called kappa and lambda, based on the amino acid sequences of their constant domains. Depending on the amino acid sequence of the constant domain of their heavy chains ($C_H$), immunoglobulins may be assigned to different classes or isotypes. There are five classes of immunoglobulins: IgA, IgD, IgE, IgG, and IgM, having heavy chains designated alpha, delta, epsilon, gamma and mu, respectively. The gamma and alpha classes are further divided into subclasses on the basis of relatively minor differences in $C_H$ sequence and function, e.g., humans express the following subclasses: IgG1, IgG2, IgG3, IgG4, IgA1 and IgA2.

Members of the Camelidae family, e.g., llama, camel and dromedaries, contain a unique type of antibody, that are devoid of light chains, and further lack the $C_{H1}$ domain (Muyldermans, S., Rev. Mol. Biotechnol., Vol. 74, pp. 277-302 (2001)). The variable region of these heavy chain antibodies are termed $V_{HH}$ or VHH, and constitute the smallest available intact antigen-binding fragment (15 kDa) derived from a functional immunoglobulin.

The term "variable" refers to the fact that certain segments of the variable domains differ extensively in sequence among antibodies. The V domain mediates antigen binding and defines specificity of a particular antibody for its antigen. However, the variability is not evenly distributed across the 110-amino acid span of the variable domains. Instead, the V regions consist of relatively invariant stretches called framework regions (FR) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies. The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 1-35 (H1), 50-65 (H2) and 95-102 (H3) in the $V_H$; Kabat et al., Sequences of Proteins of Immunological Interest, 5th Ed. Public Health Service, National Institutes of Health, Bethesda, Md. (1991)) and/or those residues from a "hypervariable loop".

The term "monoclonal antibody" as used herein refers to an antibody obtained from a population of substantially homogeneous antibodies, i.e., the individual antibodies comprising the population are identical except for possible naturally occurring mutations that may be present in minor amounts. In contrast to polyclonal antibody preparations which include different antibodies directed against different epitopes, each monoclonal antibody is directed against a single epitope, i.e., a single antigenic determinant. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology or may be made using recombinant DNA methods in bacterial, eukaryotic animal or plant cells (see, e.g., U.S. Pat. No. 4,816,567). The "monoclonal antibodies" may also be isolated from phage antibody libraries, using the available techniques, e.g., Clackson et al., Nature, Vol. 352, pp. 624-628 (1991).

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, Vol. 81, pp. 6851-6855 (1984)).

An "antibody fragment" comprises a portion of a multimeric antibody, preferably the antigen binding or variable region of the intact antibody. Examples of antibody fragments include Fab, Fab', F(ab')$_2$, dimers and trimers of Fab conjugates, Fv, scFv, minibodies; dia-, tria- and tetrabodies; linear antibodies (See Hudson et al., Nature Med. Vol. 9, pp. 129-134 (2003)).

"Fv" is the minimum antibody fragment which contains a complete antigen binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, and are therefore included in the definition of Fv.

A single-chain variable fragment (scFv) is a fusion protein of the variable regions of the heavy ($V_H$) and light chains ($V_L$) of immunoglobulins, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker.

Divalent (or bivalent) single-chain variable fragments (di-scFvs, bi-scFvs) can be engineered by linking two scFvs. This can be done by producing a single peptide chain with two $V_H$ and two $V_L$ regions, yielding tandem scFvs. Another possibility is the creation of scFvs with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Consequently, diabody drugs could be dosed much lower than other therapeutic antibodies and are capable of highly specific targeting of tumors in vivo. Still shorter linkers (one or two amino acids) lead to the formation of trimers, so-called triabodies or tribodies. Tetrabodies are known and have been shown to exhibit an even higher affinity to their targets than diabodies.

The term "humanized antibody" or "human antibody" refers to antibodies which comprise heavy and light chain variable region sequences from a non-human species (e.g., a mouse) but in which at least a portion of the $V_H$ and/or $V_L$ sequence has been altered to be more "human-like", i.e., more similar to human germline variable sequences. One type of humanized antibody is a CDR-grafted antibody, in which human CDR sequences are introduced into non-human $V_H$ and $V_L$ sequences to replace the corresponding nonhuman CDR sequences. Means for making chimeric, CDR-grafted and humanized antibodies are known to those of ordinary skill in the art (see, e.g., U.S. Pat. Nos. 4,816,567 and 5,225,539). One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals may be made using XenoMouse® technology or by using a "minilocus" approach. Methods for making XenoMice® are described in U.S. Pat. Nos. 6,162,963, 6,150,584, 6,114,598 and 6,075,181. Methods for making transgenic animals using the "minilocus" approach are described in U.S. Pat. Nos. 5,545,807, 5,545,806, 5,625,825, and WO 93/12227.

Humanization of a non-human antibody has become routine in recent years, and is now within the knowledge of one skilled in the art. Several companies provide services to make a humanized antibody, e.g., Xoma, Aries, Medarex, PDL and Cambridge Antibody Technologies. Humanization protocols are extensively described in technical literature, e.g., Kipriyanov and Le Gall, Molecular Biotechnol, Vol. 26, pp 39-60 (2004), Humana Press, Totowa, N.J.; Lo, Methods Mol. Biol., Vol. 248, pp 135-159 (2004), Humana Press, Totowa, N.J.; Wu et al., J. Mol. Biol. Vol. 294, pp. 151-162 (1999).

In certain embodiments, antibodies useful in the present invention may be expressed in cell lines other than hybridoma cell lines. Sequences encoding particular antibodies may be used for transformation of a suitable mammalian host cell by known methods for introducing polynucleotides into a host cell, including, for example packaging the polynucleotide in a virus (or into a viral vector) and transducing a host cell with the virus (or vector), or by transfection procedures known in the art, as exemplified by U.S. Pat. Nos. 4,399,216, 4,912,040, 4,740,461 and 4,959,455. The transformation procedure used may depend upon the host to be transformed. Methods for introduction of heterologous polynucleotides into mammalian cells are known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

A nucleic acid molecule encoding the amino acid sequence of a heavy chain constant region, a heavy chain variable region, a light chain constant region, or a light chain variable region of an antibody, or a fragment thereof in a suitable combination if desired, is/are inserted into an appropriate expression vector using standard ligation techniques. The antibody heavy chain or light chain constant region may be appended to the C-terminus of the appropriate variable region and is ligated into an expression vector. The vector is typically selected to be functional in the particular host cell employed (i.e., the vector is compatible with the host cell machinery such that amplification of the gene and/or expression of the gene may occur). For a review of expression vectors, see Methods Enzymol., Vol. 185, (Goeddel, ed.), 1990, Academic Press.

Identification of Specific Binding Agents

Suitable HPTPβ-ECD binding agents may be identified using a variety of techniques known in the art. For example, candidate agents can be screened for binding to HPTPβ, and screened for activity. Generally, the candidate agents will first be screened for binding and those that show selective binding will then be screened to determine ability to inhibit the HPTPβ-mediated dephosphorylation of Tie2. In some cases however the candidate agents may be first screened in vivo for activity.

Determination of Binding Activity

The selection of a suitable assay for use in identification of a specific binding agent depends on the nature of the candidate agent to be screened. One of skill in the art would be able to choose the appropriate assays for the particular candidate agent.

For example, where the candidates are antibodies or peptibodies, which comprises an Fc moeity, FACS analysis as described in Example 3B allows the candidate agent to be selected based on its ability to bind to cells, which express HPTPβ. The cell may endogenously express HPTPβ or may be genetically engineered to express HPTPβ.

For other candidate agents such as aptamers, other techniques are known in the art. For example, aptamers which specifically bind to HPTPβ can be selected using a technique known as SELEX (systematic evolution of ligands by exponential enrichment) which selects specific aptamers through repeated rounds of in vitro selection.

Determination of Inhibitor Activity by Western Blot

As exemplified in Example 4, in one suitable assay HUVECs are cultured in serum free media in the presence or absence of various concentrations of candidate agent and lysates of the cells are prepared, immunoprecipitated with a Tie2 antibody, resolved by polyacrylamide gel electrophoresis and transferred to a PVDF membrane. Membrane-bound immunoprecipitated proteins are then serially western blotted with an antiphosphotyrosine antibody to quantify Tie2 phosphorylation followed by a Tie2 antibody to quantify total Tie2. Tie2 phosphorylation is expressed as the ratio of the anti-phosphotyrosine signal over the total Tie2 signal. Greater levels of the anti-phosphotyrosine signal indicate greater HPTPβ inhibition by the candidate agent.

Candidate agents that can be screened include, but are not limited to, libraries of known agents, including natural products, such as plant or animal extracts, biologically active molecules including proteins, peptides including but not limited to members of random peptide libraries and combinatorial chemistry derived molecular library made of D- or L-configuration amino acids, antibodies including, but not limited to, polyclonal, monoclonal, chimeric, human, single chain antibodies, Fab, F(ab)₂ and Fab expression library fragments and eptiope-binding fragments thereof.

As used herein "antibody fragments" include, but are not limited, to a F(ab')$_2$, a dimer or trimer of an Fab, Fv, scFv, or a dia-, tria-, or tetrabody derived from an antibody.

Methods

Disclosed are methods for the treatment of diseases or conditions of the eye, especially retinopathies, ocular edema and ocular neovascularization. Non-limiting examples of these diseases or conditions include diabetic macular edema, age-related macular degeneration (wet form), choroidal neovascularization, diabetic retinopathy, ocular ischemia, uveitis, retinal vein occlusion (central or branch), ocular trauma, surgery induced edema, surgery induced neovascularization, cystoid macular edema, ocular ischemia, uveitis, and the like. These diseases or conditions are characterized by changes in the ocular vasculature whether progressive or non-progressive, whether a result of an acute disease or condition, or a chronic disease or condition.

One aspect of the disclosed methods relates to diseases that are a direct or indirect result of diabetes, inter alia, diabetic macular edema and diabetic retinopathy. The ocular vasculature of the diabetic becomes unstable over time leading to conditions such as non-proliferative retinopathy, macular edema, and proliferative retinopathy. As fluid leaks into the center of the macula, the part of the eye where sharp, straight-ahead vision occurs, the buildup of fluid and the associated protein begin to deposit on or under the macula. This results in swelling that disturbs the subject's central vision. This condition is referred to as "macular edema." Another condition that may occur is non-proliferative retinopathy in which vascular changes, such as microaneurysms, may occur outside the macular region of the eye.

These conditions may or may not progress to diabetic proliferative retinopathy which is characterized by neovascularization. These new blood vessels are fragile and are susceptible to bleeding. The result is scaring of the retina, as well as occlusion or total blockage of the light pathway through the eye due to the over formation of new blood vessels. Typically, subjects having diabetic macular edema are suffering from the non-proliferative stage of diabetic retinopathy; however, it is not uncommon for subjects to only begin manifesting macular edema at the onset of the proliferative stage.

Diabetic retinopathy, if left untreated, can lead ultimately to blindness. Indeed, diabetic retinopathy is the leading cause of blindness in working-age populations.

Therefore, the disclosed methods relate to preventing, treating, controlling, abating, and/or otherwise minimizing ocular neovascularization in a subject having diabetes or a subject diagnosed with diabetes. In addition, subjects having or subjects diagnosed with diabetes can be alerted to or can be made aware of the risks of developing diabetes-related blindness, therefore the present methods can be used to prevent or delay the onset of non-proliferative retinopathy in subjects known to be at risk Likewise, the present methods can be used for treating subjects having or being diagnosed with non-proliferative diabetic retinopathy to prevent progression of the condition.

The disclosed methods relate to preventing or controlling ocular neovascularization or treating a disease or condition that is related to the onset of ocular neovascularization by administering to a subject an effective amount of an HPTPβ-ECD binding agent or a pharmaceutically acceptable salt thereof.

One aspect of this method relates to treating or preventing ocular neovascularization by administering to a subject an effective amount of an HPTPβ-ECD binding agent or pharmaceutically acceptable salt thereof. One embodiment of this aspect relates to a method for treating ocular neovascularization comprising administering to a subject a composition comprising an effective amount of an HPTPβ-ECD binding agent or a pharmaceutically acceptable salt thereof, and one or more carrier or compatible excipient.

Thus, one embodiment of the present disclosure is a method of treating or preventing ocular neovascularization in a subject, comprising administering an effective amount of an HPTPβ-ECD binding agent or a pharmaceutically acceptable salt thereof. Another embodiment of the present disclosure is a method of treating or preventing ocular neovascularization in a subject, comprising administering an effective amount of a composition comprising an HPTPβ-ECD binding agent or a pharmaceutically acceptable salt thereof, and one or more carrier or compatible excipient. Yet another embodiment of the present disclosure is the use of an HPTPβ-ECD binding agent in the treatment of ocular neovascularization.

The disclosed methods also relate to preventing or controlling ocular edema or treating a disease or condition that is related to the onset of ocular edema by administering to a subject an HPTPβ-ECD binding agent.

One aspect of this method relates to treating or preventing ocular edema by administering to a subject an effective amount of an HPTPβ-ECD binding agent or a pharmaceutically acceptable salt thereof. One embodiment of this aspect relates to a method for treating ocular edema comprising administering to a subject a composition comprising:
  a. an effective amount of an HPTPβ-ECD binding agent or a pharmaceutically acceptable salt thereof; and
  b. one or more carriers or compatible excipients.

Thus, one embodiment of the present disclosure is a method of treating or preventing ocular edema in a subject, comprising administering an effective amount of an HPTPβ-ECD binding agent or a pharmaceutically acceptable salt thereof. Another embodiment of the present disclosure is a method of treating or preventing ocular edema in a subject, comprising administering an effective amount of a composition comprising HPTPβ-ECD binding agent or a pharmaceutically acceptable salt thereof, and one or more carriers or compatible excipients. An embodiment of the present disclosure is the use of an HPTPβ-ECD binding agent in the treatment of ocular edema.

Another disclosed method relates to preventing or controlling retinal edema or retinal neovascularization, or treating a disease or condition that is related to the onset of retinal edema or retinal neovascularization, by administering to a subject an HPTPβ-ECD binding agent. One aspect of this method relates to treating or preventing retinal edema or retinal neovascularization by administering to a subject an effective amount of an HPTPβ-ECD binding agent or pharmaceutically acceptable salt thereof. One embodiment of this aspect relates to a method for treating retinal edema or retinal neovascularization comprising administering to a subject a composition comprising an effective amount of an HPTPβ-ECD binding agent or pharmaceutically acceptable salt thereof, and one or more carriers or compatible excipients.

Thus, one embodiment of the present disclosure is a method of treating or preventing retinal edema in a subject, comprising administering an effective amount of an HPTPβ-ECD binding agent or a pharmaceutically acceptable salt thereof. Another embodiment is a method of treating or preventing retinal neovascularization comprising administering an effective amount of an HPTPβ-ECD binding agent or a pharmaceutically acceptable salt thereof. One embodiment of the present disclosure is a method of treating or preventing retinal edema in a subject, by administering a composition comprising an effective amount of an HPTPβ-ECD binding agent or a pharmaceutically acceptable salt thereof, and one or more carriers or compatible excipients. Another embodiment is a method of treating or preventing retinal neovascularization by administering an effective amount of an HPTPβ-ECD binding agent or a pharmaceutically acceptable salt thereof, and one or more carriers or compatible excipients. Another embodiment is the use of an HPTPβ-ECD binding agent in the treatment of retinal edema. A further embodiment is the use of an HPTPβ-ECD binding agent in the treatment of retinal neovascularization.

A further disclosed method relates to treating, preventing or controlling diabetic retinopathy, or treating a disease or condition that is related to the onset of diabetic retinopathy by administering to a subject an HPTPβ-ECD binding agent.

One aspect of this method relates to treating or preventing diabetic retinopathy by administering to a subject an effective amount of an HPTPβ-ECD binding agent or pharmaceutically acceptable salt thereof. One embodiment of this aspect relates to a method for treating diabetic retinopathy comprising administering to a subject a composition comprising an effective amount of an HPTPβ-ECD binding agent or a pharmaceutically acceptable salt thereof, and one or more carrier or compatible excipient.

Thus, one embodiment of the present disclosure is a method of treating or preventing diabetic retinopathy in a subject, comprising administering an effective amount of an HPTPβ-ECD binding agent or a pharmaceutically acceptable salt thereof. Another embodiment of the present disclosure is a method of treating or preventing diabetic retinopathy in a subject, by administering a composition comprising an effective amount of an HPTPβ-ECD binding agent or a pharmaceutically acceptable salt thereof, and one or more carriers or compatible excipients. Yet another embodiment of the present disclosure is the use of an HPTPβ-ECD binding agent in the treatment of diabetic retinopathy.

A further disclosed method relates to a method for treating or preventing non-proliferative retinopathy comprising administering to a subject an effective amount of an HPTPβ-ECD binding agent or pharmaceutically acceptable salt thereof.

Another embodiment of this aspect relates to a method for treating or preventing non-proliferative retinopathy comprising administering to a subject a composition comprising an effective amount of an HPTPβ-ECD binding agent or pharmaceutically acceptable salt thereof; and one or more carrier or compatible excipient.

Thus, one embodiment of the present disclosure is a method of treating or preventing non-proliferative retinopathy in a subject, comprising administering an effective amount of an HPTPβ-ECD binding agent or a pharmaceutically acceptable salt thereof. Another embodiment of the present disclosure is a method of treating or preventing non-proliferative retinopathy in a subject, by administering a composition comprising an effective amount of an HPTPβ-ECD binding agent or a pharmaceutically acceptable salt thereof, and one or more carriers or compatible excipients. Yet another embodiment of the present disclosure is the use of an HPTPβ-ECD binding agent in the treatment of non-proliferative retinopathy.

Yet a further disclosed method relates to preventing or controlling diabetic macular edema, or treating a disease or condition that is related to the onset of diabetic macular edema by administering to a subject an HPTPβ-ECD binding agent.

One aspect of this method relates to treating or preventing diabetic macular edema by administering to a subject an effective amount of an HPTPβ-ECD binding agent or pharmaceutically acceptable salt thereof. One embodiment of this aspect relates to a method for treating diabetic macular edema comprising administering to a subject a composition comprising: a) an effective amount of one or more of an HPTPβ-ECD binding agent or a pharmaceutically acceptable salt thereof; and b) one or more carriers or compatible excipients.

Thus, one embodiment of the present disclosure is a method of treating or preventing diabetic macular edema in a subject, comprising administering an effective amount of an HPTPβ-ECD binding agent or a pharmaceutically acceptable salt thereof. Another embodiment of the present disclosure is a method of treating or preventing diabetic macular edema in a subject, by administering a composition comprising an effective amount of an HPTPβ-ECD binding agent or a pharmaceutically acceptable salt thereof, and one or more carriers or compatible excipients. Yet another embodiment of the present disclosure is the use of an HPTPβ-ECD binding agent in the treatment of diabetic macular edema.

Another embodiment of the present disclosure is a method for treating, or preventing age-related wet form macular degeneration edema in a subject, comprising administering an effective amount of an HPTPβ-ECD binding agent or a pharmaceutically acceptable salt thereof. Another embodiment of the present disclosure is a method of treating or preventing age-related wet form macular degeneration edema in a subject, by administering a composition comprising an effective amount of an HPTPβ-ECD binding agent or a pharmaceutically acceptable salt thereof, and one or more carriers or compatible excipients. Yet another embodiment of the present disclosure is the use of an HPTPβ-ECD binding agent in the treatment of age-related wet form macular degeneration edema.

A further embodiment is a method for treating, preventing or controlling choroidal neovascularization, central retinal vein occlusion, branch retinal vein occlusion, ocular trauma, surgery induced edema, surgery induced neovascularization, cystoid macular edema, ocular ischemia, or uveitis, by administering to a subject an effective amount of an HPTPβ-ECD binding agent or a pharmaceutically acceptable salt thereof. Another embodiment is a method for treating, preventing or controlling choroidal neovascularization, central retinal vein occlusion, branch retinal vein occlusion, ocular trauma, surgery induced edema, surgery induced neovascularization, cystoid macular edema, ocular ischemia, retinal angiomatous proliferation, macular telangiectasia, or uveitis, by administering to a subject a composition comprising an effective amount of an HPTPβ-ECD binding agent or a pharmaceutically acceptable salt thereof, and one or more carriers or compatible excipients. Yet another embodiment of the present disclosure is the use of an HPTPβ-ECD binding agent in the treatment of choroidal neovascularization, central retinal vein occlusion, branch retinal vein occlusion, ocular trauma, surgery induced edema, surgery induced neovascularization, cystoid macular edema, ocular ischemia, retinal angiomatous proliferation, macular telangiectasia or uveitis.

Another embodiment is a composition for treating or preventing an ocular disorder, comprising an HPTPβ-ECD binding agent or pharmaceutically acceptable salt thereof, and one or more pharmaceutically acceptable carrier. Yet another embodiment is a composition for treating or preventing an ocular disorder, comprising an HPTPβ-ECD binding agent or pharmaceutically acceptable salt thereof, and one or more pharmaceutically acceptable carrier composition wherein the ocular disorder is ocular neovascularization, ocular edema, retinal neovascularization, diabetic retinopathy, diabetic macular edema, age-related macular degeneration, choroidal neovascularization, central retinal vein occlusion, branch retinal vein occlusion, ocular trauma, surgery induced edema, surgery induced neovascularization, cystoid macular edema, ocular ischemia, non-proliferative retinopathy, retinal angiomatous proliferation, macular telangiectasia, or uveitis.

In some embodiments, the HPTPβ-ECD binding agent or pharmaceutically acceptable salt thereof is used for treating an ocular disorder. In some embodiments, the HPTPβ-ECD binding agent or pharmaceutically acceptable salt thereof is used for treating an ocular disorder, wherein the ocular disorder is ocular neovascularization, ocular edema, retinal neovascularization, diabetic retinopathy, diabetic macular edema, age-related macular degeneration, choroidal neovascularization, central retinal vein occlusion, branch retinal vein occlusion, ocular trauma, surgery induced edema, surgery induced neovascularization, cystoid macular edema, ocular ischemia, non-proliferative retinopathy, retinal angiomatous proliferation, macular telangiectasia or uveitis.

In still other embodiments, the HPTPβ-ECD binding agent or pharmaceutically acceptable salt thereof is used for the manufacture of a medicament for treating an ocular disorder. In some embodiments the ocular disorder is ocular neovascularization, ocular edema, retinal neovascularization, diabetic retinopathy, diabetic macular edema, age-related macular degeneration, choroidal neovascularization, central retinal vein occlusion, branch retinal vein occlusion, ocular trauma, surgery induced edema, surgery induced neovascularization, cystoid macular edema, ocular ischemia, non-proliferative retinopathy, retinal angiomatous proliferation, macular telangiectasia or uveitis.

Dosing

Effective dosages and schedules for administering the HPTPβ-ECD binding agent may be determined empirically, and making such determinations is within the skill in the art. Those skilled in the art will understand that the dosage of the agent that must be administered will vary depending on, for example, the subject which will receive the agent, the route of administration, the particular type of agent used and other drugs being administered to the subject. For example, guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical dose of the agent used alone might range from about 0.01 mg/kg to up to 500 mg/kg of body weight or more per day, or from about 0.01 mg/kg to about 50 mg/kg, or from 0.1 mg/kg to about 50 mg/kg, or from about 0.1 mg/kg to up to about 10 mg/kg, or from about 0.2 mg/kg to about 1 mg/kg, depending on the factors mentioned above.

One embodiment relates to a method for treating ocular edema and/or neovascularization comprising administering to a subject from about 0.01 mg/kg to about 50 mg/kg of an HPTPβ-ECD binding agent or pharmaceutically acceptable salt thereof. Another iteration of this embodiment relates to administering to a subject from about 0.1 mg/kg to about 10 mg/kg by weight of the subject being treated, an HPTPβ-ECD binding agent or pharmaceutically acceptable salt thereof. A further iteration of this embodiment relates to a method for treating or preventing diseases or conditions related to ocular edema and/or neovascularization comprising administering to a subject from about 1 mg/kg to about 10 mg/kg by weight of the subject an HPTPβ-ECD binding agent or pharmaceutically acceptable salt thereof. Yet another iteration of this embodiment relates to a method for treating or preventing diseases or conditions related to ocular edema and/or neovascularization comprising administering to a subject from about 5 mg/kg to about 10 mg/kg by weight of the subject an HPTPβ-ECD binding agent or pharmaceutically acceptable salt thereof. In a further iteration of this embodiment relates to a method for treating or preventing diseases or conditions related to ocular edema and/or neovascularization comprising administering to a subject from about 1 mg/kg to about 5 mg/kg by weight of the subject an HPTPβ-ECD binding agent or pharmaceutically acceptable salt thereof. In a yet further iteration of this embodiment relates to a method for treating or preventing diseases or conditions related to ocular edema and/or neovascularization comprising administering to a subject from about 3 mg/kg to about 7 mg/kg by weight of the subject an HPTPβ-ECD binding agent or pharmaceutically acceptable salt thereof.

The dosing schedules for administration of an HPTPβ-ECD binding agent include, but are not limited to, once daily, three-times weekly, twice weekly, once weekly, three times, twice monthly, once monthly and once every other month.

Further disclosed are methods of treating or preventing one or more of the diseases or conditions described herein above related to ocular edema and/or neovascularization that are the result of administration of another pharmaceutically active agent. As such, this aspect relates to a method comprising administering to a subject a composition comprising: a) an effective amount of an HPTPβ-ECD binding agent or pharmaceutically acceptable salt thereof; b) one or more additional pharmaceutically active agents; and c) one or more carriers or compatible excipients.

The methods of the present invention may be combined with the standard of care, including, but not limited to, laser treatment.

Non-limiting examples of pharmaceutically active agents suitable for combination with an HPTPβ-ECD binding agent include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, ophthalmic preparations and the like.

The disclosed method also relates to the administration of the disclosed agents and compositions. Administration can be systemic via subcutaneous or i.v. administration; or the HPTP-β inhibitor will be administered directly to the eye, e.g., local. Local methods of administration include, for example, by eye drops, subconjunctival injections or implants, intravitreal injections or implants, sub-Tenon's injections or implants, incorporation in surgical irrigating solutions, etc.

The disclosed methods relate to administering an HPTPβ-ECD binding agent as part of a pharmaceutical composition. Compositions suitable for local administration are known to the art (see, for example, U.S. Pat. Publ. 2005/0059639). In various embodiments, compositions of the invention can comprise a liquid comprising an active agent in solution, in suspension, or both. As used herein, liquid compositions include gels. In one embodiment, the liquid composition is aqueous. Alternatively, the composition can take form of an ointment. In another embodiment, the composition is an in situ gellable aqueous composition. Such a composition can comprise a gelling agent in a concentration effective to promote gelling upon contact with the eye or lacrimal fluid in the exterior of the eye. Aqueous compositions of the invention have ophthalmically compatible pH and osmolality. The composition can comprise an ophthalmic depot formulation comprising an active agent for subconjunctival administration. The microparticles comprising active agent can be embedded in a biocompatible pharmaceutically acceptable polymer or a lipid encapsulating agent. The depot formulations may be adapted to release all or substantially all the active material over an extended period of time. The polymer or lipid matrix, if present, may be adapted to degrade sufficiently to be transported from the site of administration after release of all or substantially all the active agent. The depot formulation can be a liquid formulation, comprising a pharmaceutical acceptable polymer and a dissolved or dispersed active agent. Upon injection, the polymer forms a depot at the injections site, e.g., by gelifying or precipitating. The composition can comprise a solid article that can be inserted in a suitable location in the eye, such as between the eye and eyelid or in the conjuctival sac, where the article releases the active agent. Solid articles suitable for implantation in the eye in such fashion generally comprise polymers and can be bioerodible or non-bioerodible.

In one embodiment of the disclosed methods, a human subject with at least one visually impaired eye is treated with 2-4000 µg of an HPTPβ-ECD binding agent via intravitreal injection. Improvement of clinical symptoms are monitored by one or more methods known to the art, for example, indirect ophthalmoscopy, fundus photography, fluorescein angiopathy, electroretinography, external eye examination, slit lamp biomicroscopy, applanation tonometry, pachymetry, optical coherence tomography and autorefaction. Subsequent doses can be administered weekly or monthly, e.g., with a frequency of 2-8 weeks or 1-12 months apart.

The disclosed methods include administration of the disclosed agents in combination with a pharmaceutically acceptable carrier. "Pharmaceutically acceptable" means a material that is not biologically or otherwise undesirable, i.e., the material may be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art. In another aspect, many of the disclosed agents can be used prophylactically, i.e., as a preventive agent, either neat or with a pharmaceutically acceptable carrier. The ionic liquid compositions disclosed herein can be conveniently formulated into pharmaceutical compositions composed of neat ionic liquid or in association with a pharmaceutically acceptable carrier. See Remington's Pharmaceutical Sciences, 18th ed., Gennaro, AR. Ed., Mack Publishing, Easton Pa. (1990), which discloses typical carriers and conventional methods of preparing pharmaceutical compositions that can be used in conjunction with the preparation of formulations of the agents described herein and which is incorporated by reference herein. Such pharmaceutical carriers, most typically, would be standard carriers for administration of compositions to humans and non-humans, including solutions such as sterile water, saline and buffered solutions at physiological pH. Other agents can be administered according to standard procedures used by those skilled in the art. For example, pharmaceutical compositions can also include one or more additional active ingredients such as antimicrobial agents, anti-inflammatory agents, anesthetics and the like.

Examples of pharmaceutically-acceptable carriers include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the disclosed agents, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other agents can be administered according to standard procedures used by those skilled in the art.

Pharmaceutical formulations can include additional carriers, as well as thickeners, diluents, buffers, preservatives, surface active agents and the like in addition to the agents disclosed herein. Pharmaceutical formulations can also include one or more additional active ingredients such as antimicrobial agents, anti-inflammatory agents, anesthetics and the like.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system. The formulator can also take advantage of the fact the agents of the present invention have improved cellular potency, pharmacokinetic properties.

The disclosed agents can also be present in liquids, emulsions, or suspensions for delivery of active therapeutic agents. Liquid pharmaceutically administrable compositions can, for example, be prepared by dissolving, dispersing, etc., an active agent as described herein and optional pharmaceutical adjuvants in an excipient, such as, for example, water, saline aqueous dextrose, glycerol, ethanol and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art, for example see Remington's Pharmaceutical Sciences, referenced above.

Kits

Also disclosed are kits comprising the agents and compositions to be delivered into a human, mammal, or cell. The kits can comprise one or more packaged unit doses of a composition comprising one or more agents to be delivered into a human, mammal, or cell. The unit dosage ampoules or multi-dose containers, in which the agents to be delivered are packaged prior to use, can comprise a hermetically sealed container enclosing unit dose of the composition, or multiples unit doses. The agents can be packaged as a sterile formulation, and the hermetically sealed container is designed to preserve sterility of the formulation until use.

EXAMPLES

Example 1

Production of HPTPβ Extracellular Domain Protein

Full length HPTPβ cDNA (SEQ ID NO:1) is cloned from a human placental library according to the manufacturer's (Origene) instructions. A cDNA encoding the entire soluble extracellular domain (ECD) of HPTPβ is cloned by PCR from the full length cDNA coding for amino acids 1-1621 with an added c-terminal His-His-His-His-His-His-Gly (6His-Gly) (SEQ ID NO:3). The resulting cDNA is cloned into mammalian expression vectors for transient (pShuttle-CMV) or stable (pcDNA3.1(−)) expression in HEK293 cells. To obtain purified HPTPβ ECD (βED), HEK293 cells transfected with a βECD expression vector are incubated in OptiMEM-serum free (Gibco) for 24 hours under normal growth conditions. The conditioned media is then recovered, centrifuged to remove debris, and 1 mL of washed Ni-NTA agarose (Qiagen) (500 µL, packed material) is added to each 10 µL of cleared media and allowed to rock overnight at 4° C. On the following day, the mixture is loaded into a column and washed with 20 bed volumes of 50 mM $NaH_2PO_4$, 300 mM NaCl, 20 mM imidazole, pH 8. The purified HPTPβ extracellular domain protein (SEQ ID NO:4) is then eluted with 200 µL/elution in 50 mM $NaH_2PO_4$, 300 mM NaCl, 250 mM Imidazole, pH 8. Fractions are analyzed for protein content using reducing-denaturing SDS-polyacrylimide gel electrophoresis and detected by silver stain (Invitrogen) and confirmed by mass spectrometry.

Example 2

Generation of Monoclonal Antibodies to HPTPβ Extracellular Domain

Purified HPTPβ extracellular domain protein is produced, for example by the procedure described in Example 1. For production of the HPTPβ extracellular domain immunogen, the purified HPTPβ extracellular domain-6-His protein is conjugated to porcine thyroglobulin (Sigma) using EDC coupling chemistry (Hockfield, S. et al., (1993) Cold Spring Habor Laboratory Press. Vol. 1 pp. 111-201, Immunocytochemistry). The resulting HPTPβ extracellular domain-thyroglobulin conjugate is dialyzed against PBS, pH 7.4. Adult Balb/c mice are then immunized subcutaneously with the conjugate (100-200 µg) and complete Freund's adjuvant in a 1:1 mixture. After 2-3 weeks, the mice are injected intraperitoneally or subcutaneously with incomplete Freund's adjuvant and the conjugate in a 1:1 mixture. The injection is repeated at 4-6 weeks. Sera are collected from mice 7 days post-third-injection and assayed for immunoreactivity to HPTPβ extracellular domain antigen by ELISA and western blotting. Mice that display a good response to the antigen are boosted by a single intra-spleen injection with 50 µl of purified HPTPβ extracellular domain protein mixed 1:1 with Alum hydroxide using a 31 gauge extra long needle (Goding, J. W., (1996) Monoclonal Antibodies: Principles and Practices. Third Edition, Academic Press Limited. p. 145). Briefly, mice are anesthetized with 2.5% avertin, and a 1 centimeter incision is created on the skin and left oblique body wall. The antigen mixture is administered by inserting the needle from the posterior portion to the anterior portion of the spleen in a longitudinal injection. The body wall is sutured and the skin is sealed with two small metal clips. Mice are monitored for safe recovery. Four days after surgery the mouse spleen is removed and single cell suspensions are made for fusion with mouse myeloma cells for the creation of hybridoma cell lines (Spitz, M., (1986) Methods In Enzymology, Vol. 121. Eds. John J, Lagone and Helen Van Vunakis. pp. 33-41 (Academic Press, New York, N.Y.)). Resulting hybridomas are cultured in Dulbeccos modified media (Gibco) supplemented with 15% fetal calf serum (Hyclone) and hypoxathine, aminopterin and thymidine.

Screening for positive hybridomas begins 8 days after the fusion and continues for 15 days. Hybridomas producing anti-HPTPβ extracellular domain antibodies are identified by ELISA on two sets of 96-well plates: one coated with the histidine tagged-HPTPβ extracellular domain and another one coated with a histidine-tagged bacterial MurA protein as a negative control. The secondary antibody is a donkey anti-mouse IgG labeled with horseradish peroxidase (HRP) (Jackson Immunoresearch). Immunoreactivity is monitored in wells using color development initiated by ABTS tablets dissolved in TBS buffer, pH 7.5. The individual HRP reaction mixtures are terminated by adding 100 microliters of 1% SDS and reading absorbance at 405 nm with a spectrophotometer. Hybridomas producing antibodies that interact with HPTPβ extracellular domain-6His, and not with the murA-6His protein are used for further analysis. Limiting dilutions (0.8 cells per well) are performed twice on positive clones in 96 well plates, with clonality defined as having greater than 99% of the wells with positive reactivity. Isotypes of antibodies are determined using the iso-strip technology (Roche). To obtain purified antibody for further evaluation, tissue culture supernatants are affinity purified using a protein A or protein G columns.

Six monoclonal antibodies immunoreactive to HPTPβ-ECD protein were isolated and given the following nomenclature, R15E6, R12A7, R3A2, R11C3, R15G2 and R5A8. Based on its reaction with the HPTPβ-ECD protein in ELISA and in western blots, R15E6 was selected for further study.

Example 3

The Monoclonal Antibody R15E6

The monoclonal antibody R15E6 was identified and characterized as described in Example 2 of the present application and in U.S. Pat. No., 7,973,142; the procedure and results are summarized below.

A. R15E6 Binds Endogenous HPTPβ as Demonstrated by Demonstrated by Immunoprecipitation.

Materials: Human umbilical vein endothelial cells (HU-VECs), EGM media, and trypsin neutralizing solution from Cambrex; OPTIMEM I (Gibco), bovine serum albumin (BSA; Santa Cruz), phosphate buffered saline (PBS; Gibco), Growth Factors including Angiopoietin 1 (Ang1), vascular endothelial growth factor (VEGF) and fibroblast growth factor (FGF) (R&D Systems), Tie2 monoclonal antibody (Duke University/P&GP), VEGF receptor 2 (VEGFR2)

polyclonal antibody (Whitaker et. al), protein A/G agarose (Santa Cruz), Tris-Glycine pre-cast gel electrophoresis/transfer system (6-8%) (Invitrogen), PVDF membranes (Invitrogen), lysis buffer (20 mm Tris-HCl, 137 mm NaCl, 10% glycerol, 1% triton-X-100, 2 mM EDTA, 1 mM NaOH, 1 mM NaF, 1 mM PMSF, 1 µg/ml leupeptin, 1 µg/ml pepstatin).

Method: HUVECs were pre-treated for 30 min with antibody (in OPTIMEM) or OPTIMEM I alone. After removal of pre-treatment, cells were treated with Ang1 (100 ng/ml) for 6 minutes in PBS+0.2% BSA and lysed in lysis buffer. Lysates were run directly on a Tris-Glycine gel or immunoprecipitated with 2-5 µg/ml Tie-2 antibody or 10 µg/ml R15E6 antibody and protein A/G agarose. Immunoprecipitated samples were rinsed once with lysis buffer and boiled for 5 min in 1× times sample buffer. Samples were resolved on a Tris-Glycine gel, transferred to a PVDF membrane, and detected by western blot using the indicated antibodies (pTYR Ab (PY99, Santa Cruz), Tie-2, VEGFR2 and/or R15E6).

Results: By IP/western blotting, R15E6 recognizes a major, high molecular weight band consistent with the size of HPTPβ (FIG. 1, Panel A, Lane 2). The less intense, lower molecular weight bands likely represent less glycosylated precursor forms of HPTPβ. An immunoprecipitation (IP) with control, non-immune IgG shows no bands in the molecular weight range of HPTPβ (FIG. 1, Panel A, Lane 1), and a combined Tie2/VEGFR2 IP shows bands of the expected molecular weight (FIG. 1, Panel A, Lane 3). This result demonstrates that R15E6 recognizes and is specific for HPTPβ.

B. R15E6 Binds Endogenous HPTPβ as Demonstrated by FACS Analysis

Materials: HUVECs, EGM media, and trypsin neutralizing solution from Cambrex; Secondary Alexfluor 488-tagged antibody from Molecular Probes; Hanks balanced salt solution (Gibco); FACSCAN flow cytometer and CellQuest software from Becton Dickenson.

Method: HUVECs are trypsinized, treated with trypsin neutralizing solution and rinsed with HBSS. R15E6 antibody (0.6 µg) is added to 250,000 cells in 50 µg of HBSS and incubated on ice for 20 minutes. Cells were rinsed with 1 ml HBSS followed by adding 2 µg of fluorescent-conjugated secondary antibody for 20 minutes on ice. Cells were rinsed and resuspended in 1 ml HBSS then analyzed on the FACSCAN flow cytometer with CellQuest software. Control cells were treated with fluorescent-conjugated secondary antibody only.

Results: By FACS analysis, intact HUVECs, R15E6 causes a robust shift (>90% of cells) in the fluorescence signal compared to the secondary antibody alone (FIG. 1, Panel B). This result indicates that R15E6 binds to endogenous HPTPβ presented on the surface of intact endothelial cells.

Example 4

R15E6 Enhances Tie2 Activation

R15E6 enhances Tie2 phosphorylation in the absence and presence of the angiopoietin 1 (Ang1), the Tie2 ligand.

Methods: HUVECs are cultured in serum free media as described above in the presence or absence of various concentrations of R15E6 and with or without added Ang1. Lysates are prepared, immunoprecipitated with a Tie2 antibody, resolved by polyacrylamide gel electrophoresis and transferred to a PVDF membrane. Membrane-bound immunoprecipitated proteins are then serially western blotted with an antiphosphotyrosine antibody to quantify Tie2 phosphorylation followed by a Tie2 antibody to quantify total Tie2. Tie2 phosphorylation is expressed as the ratio of the antiphosphotyrosine signal over the total Tie2 signal.

Figure 2:
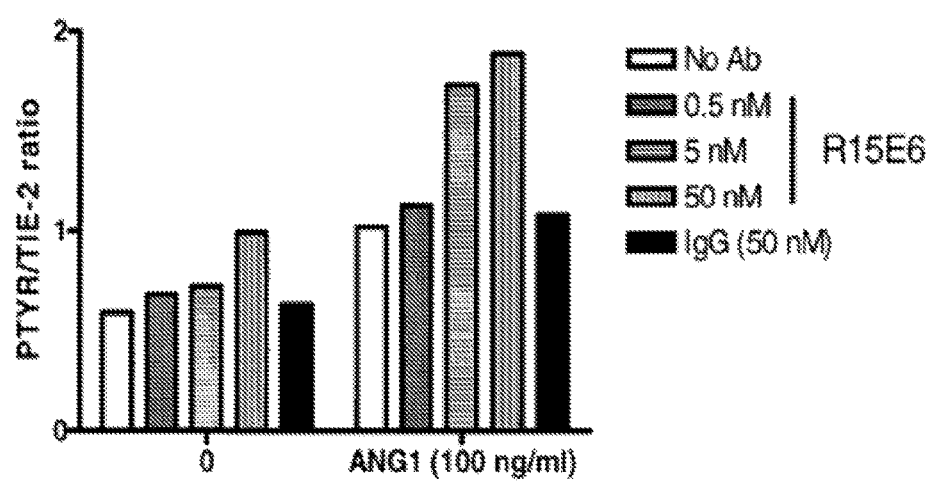
FIG. 2. The monoclonal antibody R15E6 enhances Tie2 Receptor Activation in HUVECs. Tie2 activation is measured in human endothelial cells as described in Example 4. R15E6 dose dependently enhances both basal and Ang1-induced Tie2 activation.

Results: R15E6 enhances Tie2 phosphorylation both in the absence and presence of Ang1 (FIG. 2). This result indicates that binding of R15E6 to HPTPβ on the surface of endothelial cells modulates its biological function resulting in enhanced activation of Tie2 in the absence or presence of ligand.

Example 5

Generation of Anti-VE-PTP Extracellular Domain Antibodies

A. Production of Mouse VE-PTP Extracellular Domain Protein (VE-PTP-ECD)

VE-PTP-ECD may be produced by any suitable method. Such methods are well known in the art. For example, VE-PTP-ECD can be produced using a method similar to Example 1 of the present disclosure where VE-PTP-ECD cDNA is used in place of cDNA encoding HPTPβ-ECD. SEQ ID NO:5 provides a nucleotide sequence that encodes VE-PTP-ECD. SEQ ID NO: 7 provides the amino acid sequence of VE-PTP-ECD.

B. Generation of Antibodies to VE-PTP ECD

Anti-VE-PTP antibodies are readily generated by methods that are well known in the art. For example, anti VE-PTP antibodies can be generated using the method of Example 2 of the present disclosure by substituting VE-PTP-ECD for the HPTPβ extracellular domain and immunizing rats with the resulting protein. The rat anti-mouse VE-PTP antibody used in the present studies was kindly provided by Dr. D. Vestweber (mAb 109). The antibody was generated as described in Baumer S. et al., Blood, 2006; 107: 4754-4762. Briefly, the antibody was generated by immunizing rats with a VE-PTP-Fc fusion protein. Immunization, hybridoma-fusion, and screening were conducted as described in Gotsch U., et al., J Cell Sci. 1997, Vol. 110, pp. 583-588 and Bosse R. and Vestweber D., Eur J Immunol. 1994, Vol. 24, pp. 3019-3024.

The fusion protein was constructed such that the first 8 fibronectin type III-like repeats ending with the amino acid proline at position 732 of VE-PTP were fused in frame with the Fc part of human IgG1 (starting with amino acid proline at position 239). This construct cloned into pcDNA3 (Invitrogen) was stably transfected into CHO cells, and the fusion protein was purified by protein A Sepharose affinity purification.

Example 6

Intravitreal Injections of an Anti-VE-PTP ECD Antibody

Figure 3:
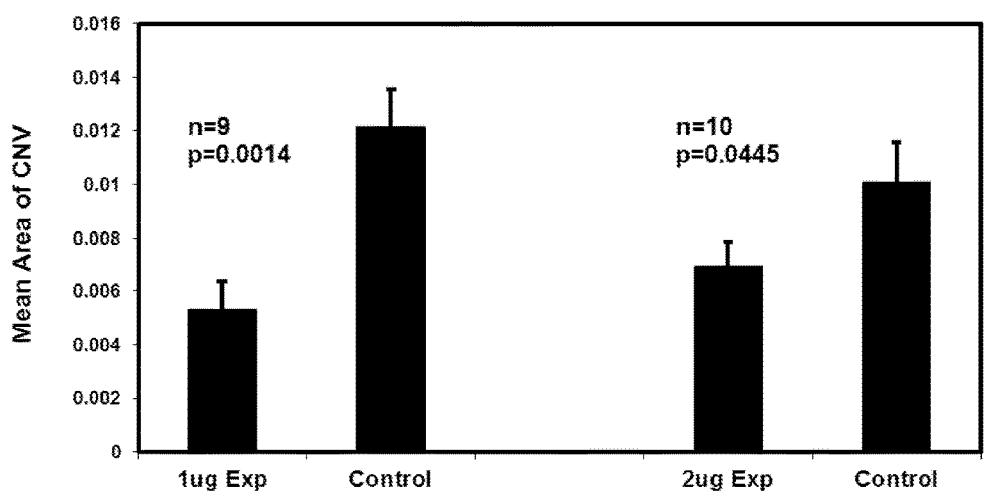
FIG. 3. Is a graphical representation of the mean area of choroidal neovascularization in C57BL/6 mice 14 days post laser injury in eyes treated with intravitreal injection of 1 μg or 2 μg of an anti-VE-PTP extracellular domain antibody in one eye versus similar treatment of the fellow eye with control.

Laser-induced Choroidal Neovascularization Model: The choroidal neovascularization model is considered to represent a model of neovascular age-related macular degeneration. Choroidal NV was generated as previously described. See Tobe T, et al., Am. J. Pathol. 1998, Vol. 153, pp. 1641-1646. Adult C57BL/6 mice had laser-induced rupture of Bruch's membrane in three locations in each eye and were then given 1 µL intravitreal injections of 1 or 2 µg of a VE-PTP-ECD antibody (IgG2a), in one eye and vehicle (5% dextrose) in the fellow eye. These treatments were repeated on day 7. Fourteen days after laser, the mice were perfused with fluorescein-labeled dextran (2×10⁶ average MW, Sigma, St. Louis, Mo.) and the extent of neovascularization was assessed in choroidal flat mounts by fluorescence microscopy. The area of CNV at each Bruch's membrane rupture site was measured by image analysis by an observer masked with respect to treatment group. The area of CNV is the average of the three rupture sites in one eye. As shown in FIG. 3, treatment with the VE-PTP-ECD antibody significantly reduced choroidal neovascularization at both 1 and 2 μg doses versus treatment with vehicle control.

Example 7

Oxygen-Induced Ischemic Retinopathy

The oxygen-induced ischemic retinopathy model is considered to represent a model of proliferative diabetic retinopathy. Ischemic retinopathy was produced in C57BL/6 mice by a method described by Smith, L. E. H., et al. Oxygen-induced retinopathy in the mouse. Invest. Ophthalmol. Vis. Sci. 35, 101-111 (1994).

Figure 4:
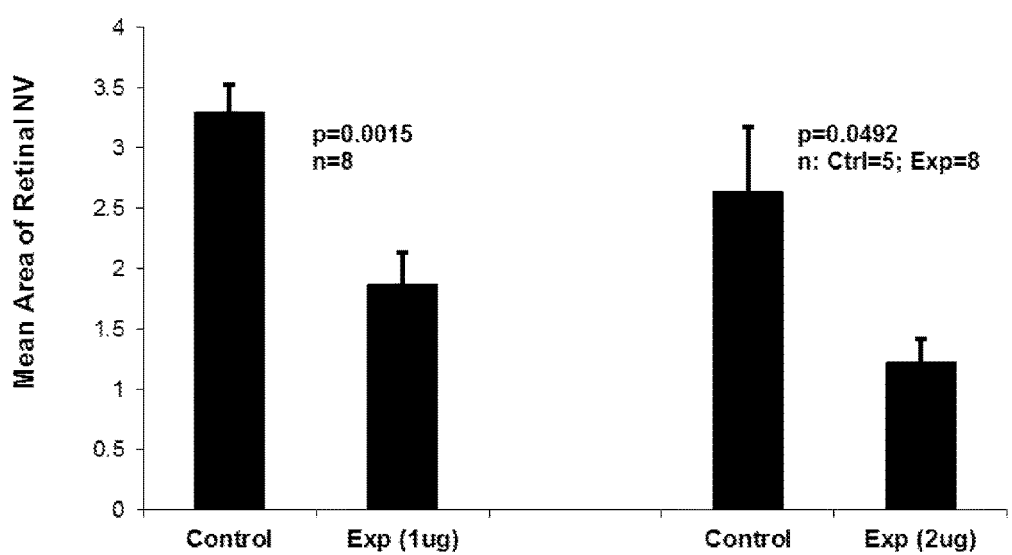
FIG. 4. Shows the mean area ($mm^2$) of retinal neovascularization in C57BL/6 mice on day P17 after containment in a 75% oxygen atmosphere from P5 to P12 and intravitreal injection of an anti-VE-PTP extracellular domain antibody at P12 when the mice were returned to room air.
Figure 5:
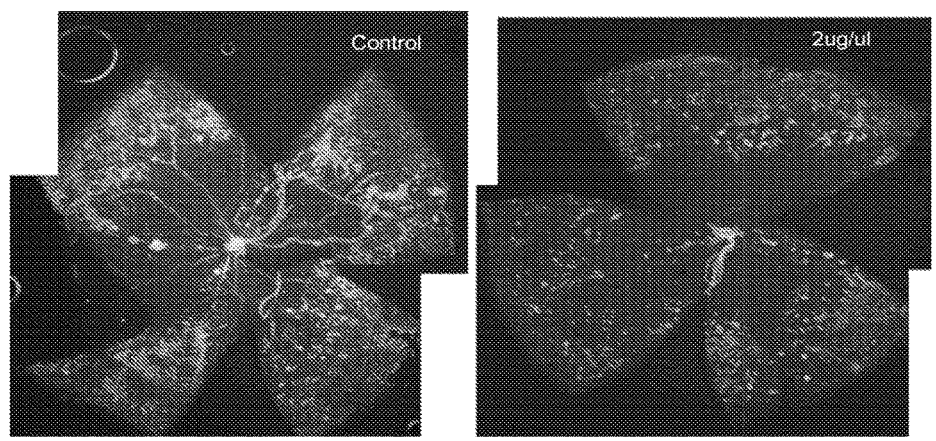
FIG. 5. Shows representative fluorescent micrographs of mouse retinas in the oxygen-induced retinopathy model after intravitreal injection of vehicle or 2 μg of an anti-VE-PTP extracellular domain antibody.

C57BL/6 mice at postnatal day 7 (P7) and their mothers were placed in an airtight chamber and exposed to hyperoxia (75±3% oxygen) for five days. Oxygen was continuously monitored with a PROOX model 110 oxygen controller (Reming Bioinstruments Co., Redfield, N.Y.). On P12, mice were returned to room air and under a dissecting microscope, a Harvard Pump Microinjection System and pulled glass pipettes were used to deliver a 1 μl intravitreal injection of 1 or 2 μg of a VE-PTP-ECD antibody was made in one eye and vehicle was injected in the fellow eye. At P17, the area of NV on the surface of the retina was measured at P17 as previously described. See Shen J, et al., Invest. Ophthalmol. Vis. Sci. 2007, Vol. 48, pp. 4335-4341. Briefly, mice were given an intraocular injection of 1 μl containing 0.5 μg rat anti-mouse PECAM antibody (Pharmingen, San Jose, Calif.). Twelve hours later, the mice were euthanized, the eyes fixed in 10% formalin. The retinas were dissected, incubated for 40 minutes in 1:500 goat anti-rat IgG conjugated with Alexa488 (Invitrogen, Carlsbad, Calif.), washed, and whole mounted. An observer masked with respect to treatment group examined the slides with a Nikon Fluorescence microscope and measured the area of NV per retina by computerized image analysis using ImagePro Plus software (Media Cybernetics, Silver Spring, Md.). FIG. 4 shows that treatment with the VE-PTP-ECD antibody significantly reduced retinal neovascularization at both 1 and 2 μg doses versus treatment with vehicle control. FIG. 5 shows representative retinal whole mounts from a mouse treated with vehicle versus a mouse treated with 2 μg of the VE-PTP-ECD antibody.

Example 8

Subcutaneous Injection of a VE-PTP-ECD Antibody

Figure 6:
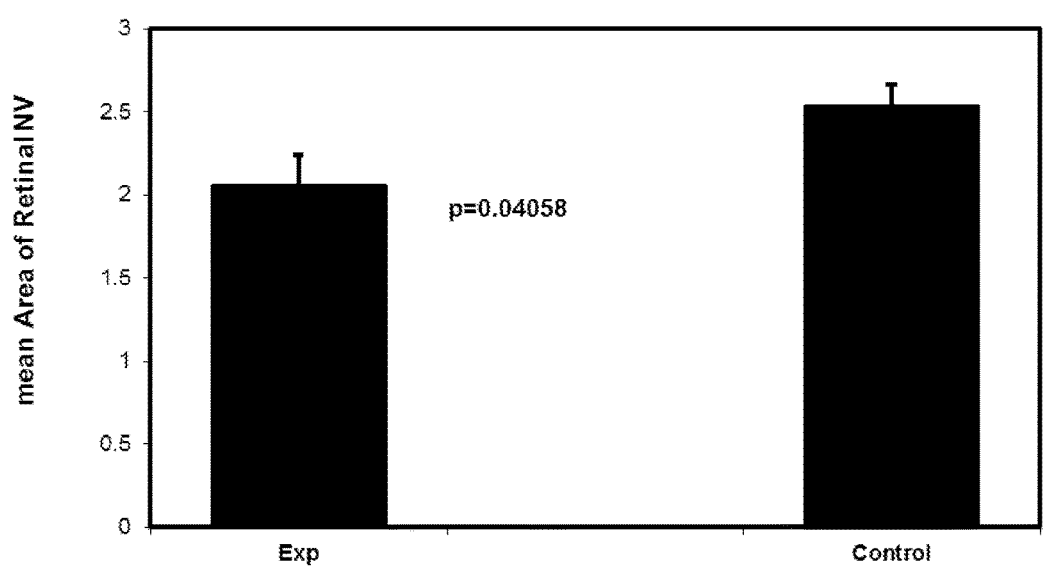
FIG. 6. Shows the mean area ($mm^2$) of retinal neovascularization in C57BL/6 mice on day P17 after containment in a 75% oxygen atmosphere from P5 to P12 followed by return to room air on P12 with subcutaneous administration of 1 mg/kg of an anti-VE-PTP extracellular domain antibody on days P12, 14 and 16.

The oxygen-induced ischemic retinopathy model was conducted as described in Example 7 (containment in a 75% oxygen atmosphere from P5 to P12) for intravitreal dosing except that the VE-PTP-ECD antibody (1 mg/kg) was dosed subcutaneously at P12 when the mice were returned to room air and again on days P14 and P16 (three total doses). Neovascularization was assessed as described above on day (P17). FIG. 6 shows that subcutaneous dosing of the VE-PTP-ECD antibody reduces the area of retinal neovascularization.

Example 9

Figure 7:
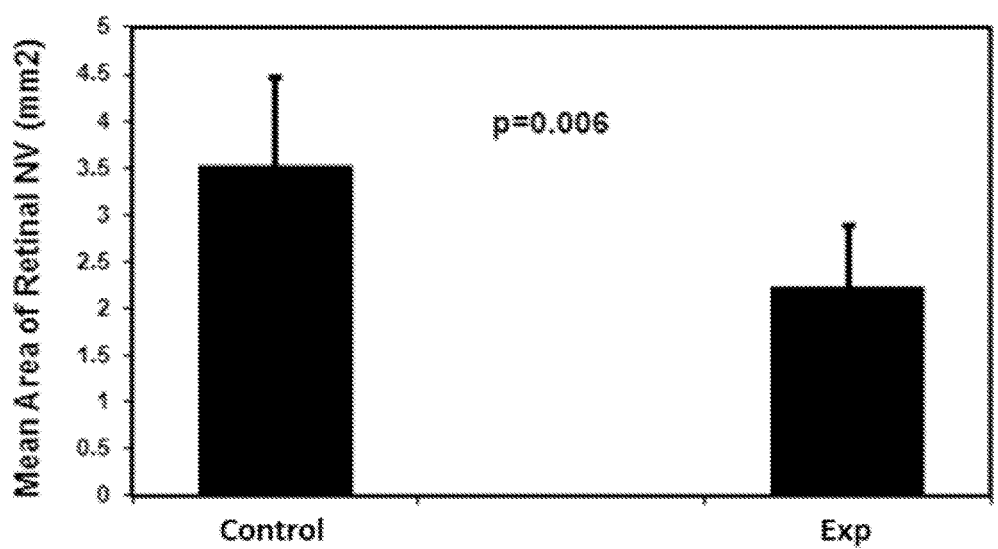
FIG. 7. Shows the mean area ($mm^2$) of retinal neovascularization in C57BL/6 mice on day P17 after containment in a 75% oxygen atmosphere from P5 to P12 followed by return to room air on P12 with subcutaneous administration of 2 mg/kg of an anti-VE-PTP extracellular domain antibody on days P12, 14 and 16.

The experiment described in Example 8 was repeated at a subcutaneous dose of 2 mg/kg. (FIG. 7)

While a number of embodiments of this disclosure are described, it is apparent that the basic examples may be altered to provide other embodiments that utilize or encompass the HPTPβ-ECD binding agent, methods and processes of this invention. The embodiments and examples are for illustrative purposes and are not to be interpreted as limiting the disclosure, but rather, the appended claims define the scope of this invention.

The invention claimed is:

1. A method for reducing retinal neovascularization in a human in need thereof, the method comprising administering to the human a therapeutically-effective amount of an intact monoclonal antibody, wherein the intact monoclonal antibody is R15E6 or a humanized form thereof, wherein the human has diabetic macular edema, wherein the antibody R15E6 is produced by a hybridoma deposited under the accession number ATCC PTA-7580.

2. The method of claim 1, wherein the intact monoclonal antibody inhibits a tyrosine phosphatase.

3. The method of claim 1, wherein the intact monoclonal antibody inhibits human protein tyrosine phosphatase beta (HPTP-β).

4. The method of claim 1, wherein the intact monoclonal antibody is administered by intraocular injection.

5. The method of claim 1, wherein the intact monoclonal antibody is administered by subcutaneous injection.

6. The method of claim 1, wherein the intact monoclonal antibody is administered by intravenous injection.

7. The method of claim 1, wherein the therapeutically-effective amount is from about 0.01 mg/kg to about 10 mg/kg by weight of the human.

8. The method of claim 1, wherein the intact monoclonal antibody binds an FN3 repeat of HPTP-β.

9. The method of claim 1, wherein the intact monoclonal antibody binds a first FN3 repeat of HPTP-β.

10. The method of claim 1, wherein the intact monoclonal antibody binds to SEQ ID NO: 4.

11. The method of claim 1, wherein the intact monoclonal antibody enhances Tie2 receptor activation.

* * * * *